(12) United States Patent
Shaw et al.

(10) Patent No.: US 9,573,972 B2
(45) Date of Patent: Feb. 21, 2017

(54) NUROTOXIC STEROL GLYCOSIDES

(75) Inventors: Christopher Ariel Shaw, North Vancouver (CA); Denis George Kay, Stratford (CA)

(73) Assignee: NEURODYN, INC. (CA)

(*) Notice: Subject to any disclaimer, the term of this patent is extended or adjusted under 35 U.S.C. 154(b) by 0 days.

(21) Appl. No.: 13/126,704

(22) PCT Filed: Oct. 30, 2009

(86) PCT No.: PCT/CA2009/001543
§ 371 (c)(1),
(2), (4) Date: Apr. 28, 2011

(87) PCT Pub. No.: WO2010/048710
PCT Pub. Date: May 6, 2010

(65) Prior Publication Data
US 2011/0280805 A1    Nov. 17, 2011

Related U.S. Application Data

(60) Provisional application No. 61/110,389, filed on Oct. 31, 2008, provisional application No. 61/174,707, filed on May 1, 2009.

(51) Int. Cl.
C07J 17/00        (2006.01)
G01N 33/50        (2006.01)
G01N 33/68        (2006.01)

(52) U.S. Cl.
CPC .......... C07J 17/00 (2013.01); G01N 33/5088 (2013.01); G01N 33/6896 (2013.01); *A01K 2267/035* (2013.01)

(58) Field of Classification Search
CPC .. G01N 33/6896; G01N 33/5088; C07J 17/00; A61K 2267/035
USPC . 554/180; 435/6, 71; 514/26; 424/9.1; 800/9
See application file for complete search history.

(56) References Cited

U.S. PATENT DOCUMENTS

| | | | |
|---|---|---|---|
| 4,188,379 A * | 2/1980 | Pegel | C07J 17/005 514/26 |
| 4,235,992 A | 11/1980 | Ueno | |
| 4,254,111 A | 3/1981 | Pegel et al. | |
| 4,260,603 A | 4/1981 | Pegel et al. | |
| 4,713,249 A | 12/1987 | Schroeder | |
| 5,128,324 A | 7/1992 | Walker et al. | |
| 5,266,333 A | 11/1993 | Cady et al. | |
| 5,270,041 A | 12/1993 | Eugster et al. | |
| 5,417,982 A | 5/1995 | Modi | |
| 5,486,510 A | 1/1996 | Bouic et al. | |
| 5,753,260 A | 5/1998 | Alving et al. | |
| 6,333,194 B1 | 12/2001 | Levy et al. | |
| 7,105,342 B2 | 9/2006 | Weiss et al. | |
| 7,112,668 B2 | 9/2006 | Rastelli et al. | |
| 8,012,456 B2 * | 9/2011 | Brown | A01K 67/0271 424/9.1 |
| 8,148,336 B2 * | 4/2012 | Shaw | A01K 67/027 435/7.1 |
| 8,497,123 B2 * | 7/2013 | Shaw | A01K 67/027 435/375 |
| 2003/0158172 A1 | 8/2003 | Koppel et al. | |
| 2004/0048810 A1 * | 3/2004 | Shaw | A01K 67/027 514/26 |
| 2004/0110938 A1 | 6/2004 | Parekh et al. | |
| 2006/0252705 A1 * | 11/2006 | Shaw et al. | 514/26 |
| 2008/0038198 A1 * | 2/2008 | Mori | G01N 33/5085 424/9.2 |
| 2010/0189647 A1 * | 7/2010 | Takayama | A01K 67/027 424/9.1 |

FOREIGN PATENT DOCUMENTS

| | | |
|---|---|---|
| CA | 2325087 | 5/2002 |
| EP | 0 858 806 | 8/1998 |
| WO | 0237122 | 5/2002 |
| WO | 2007146046 | 12/2007 |
| WO | 2008/019187 | 2/2008 |
| WO | 2009/010045 | 1/2009 |

OTHER PUBLICATIONS

Marler et al. (AN 2006:904632, HCAPLUS, DN 147:48, abstract of Functional Plant Biology, Steryl glucoside concentration declines with Cycas micronesica seed age, (2006), 33(9), 857-862).*
Khabazian et al. (AN 2002:623019, HCAPLUS, DN 137:364672), abstract of Journal of Neurochemistry (2002), 82(3), 516-528), Isolation of various forms of b-D-glucoside from the seed of Cycas circinal: neurotoxicity and implications for ALS-parkinsonism dementia complex).*
Marler, Thomas E et al. (Functional Plant Biology (2006), 33(9), 857-862).*
Khabazian et al. (Journal of Neurochemistry, 2002, 82, 516-528).*
R.C. Tabata et al. (Neuromolecular Med, 2008; 10(1):24).*
Wilson et al. (Neuromolecular Med. 2002;1(3):207-21).*
Khabazian et al. (Journal of Neurochemistry vol. 82, Issue 3, pp. 516-528, Aug. 2002).*
International Search Report/Written Opinion for PCT/CA2009/001543, completed Feb. 3, 2010.
Wilson, James, M. B., et al., "Behavioral and Neurological Correlates of ALS-Parkinsonism Dementia Complex in Adult Mice Fed Washed Cycad Flour", 2002, NeuroMolecular Medicine, vol. 1, pp. 207-221.

(Continued)

*Primary Examiner* — Sabiha N Qazi
(74) *Attorney, Agent, or Firm* — Barnes & Thornburg LLP

(57) ABSTRACT

The invention relates to compositions for use in animal models of neurodegenerative disease and methods therefor. More particularly, the invention relates to the use of neurotoxic sterol glycosides or neurotoxic glycolipids, or combinations thereof, in animal models of neurodegenerative disease. Neurotoxicity-modulating chromenols can also be used in these animal models in combination with the neurotoxic sterol glycosides or neurotoxic glycolipids, or combinations thereof.

8 Claims, 41 Drawing Sheets

(56) References Cited

OTHER PUBLICATIONS

Khabazian, I., et al., "Isolation of Various Forms of Sterol β-D-Glucoside From the Seed of Cycas Circinalis: Neurotoxicity and Implications for ALS-Parkinsonism Dementia complex", 2002 Journal of Neurochemistry, No. 82, pp. 516-528.

Ly, P.T.T., et al., "Novel Environmental Toxins: Steryl Glycosides as a Potential Etiological Factor for Age-Related Neurodegenerative Diseases", 2007, Journal of Neuroscience Research, No. 85, pp. 231-237.

European Commission, Employment, Social Affairs and Inclusion, Recommendation from the Scientific Committee on Occupational Exposure Limits for Pyridine, SCOEL/SUM/106, Nov. 2004.

Wilson, J. M. B., and C. A. Shaw. "Late appearance of glutamate transporter defects in a murine model of ALS-parkinsonism dementia complex." Neurochemistry international 50.7 (2007): 1067-1077.

Schulz, J. D., E. L. Hawkes, and C. A. Shaw. "Cycad toxins, Helicobacter pylori and parkinsonism: cholesterol glucosides as the common denomenator." Medical hypotheses 66.6 (2006): 1222-1226.

Batta, Ashok K., et al. "Stigmasterol reduces plasma cholesterol levels and inhibits hepatic synthesis and intestinal absorption in the rat." Metabolism55.3 (2006): 292-299.

Kulkarni, S. K., and Ashish Dhir. "Withania somnifera: an Indian ginseng." Progress in neuro-psychopharmacology and biological psychiatry 32.5 (2008): 1093-1105.

Misra, Laxminarain, et al. "Withanolides from Withania somnifera roots." Phytochemistry 69.4 (2008): 1000-1004.

Sahgal Arjun. Behavioral Neuroscience, 1993, vol. 1, A Practical Approach Appendix A.

Nilson, J. and Shaw, C. A. (2006), Commentary on: Return of the cycad hypothesis—does the amyotrophic lateral sclerosis/parkinsonism dementia complex (ALS/PDC) of Guam have new implications for global health?. Neuropathology and Applied Neurobiology, 32: 341-343 (abstract unavailable) doi:10.1111/0365-29902006.00718.x.

Bains, J.S. and Shaw, C.A., "Neurodegenerative disorders in humans: the role of glutathione in oxidative stress-mediated neuronal death," Brain Res. Rev., 1997, 25: 335-358.

Bindokas, V.P., Lee, C.C., Colmers, W.F., and Miller, R.J., "Changes in mitochondrial function resulting from synaptic activity in rat hippocampal slice," J. Neurosci., 1998, 18: 4570-4587.

Bouic and Lamprecht, "Plant Sterols and Sterolins: A Review of Their Immune-Modulating Properties", Altern. Med. Rev., Jun. 1999, 4(3): 170-7.

Bouic et al., "Beta-Sitosterol and Beta-Sitosterol Glucoside Stimulate Human Peripheral Blood Lynphocyte Proliferation: Implications for Their Use as an Immunomodulatory Vitamin Combination", Int. J. Immnopharmacol, Dec. 18, 1996, 18(12): 693-700.

Bouic et al., "The Effects of B-Sitosterol (BSS) and B-Sitosterol Glucoside (BSSG) Mixture on Seleted Immnue Parameters of Maratho Runners: Inhibition of Post Marathon Immune Suppression and Inflammation", Int. J. Sports Med, May 1999, 20(4): 258-262.

Campbell, P.N., Work T.S., and Mellanby, E., "Isolation of crystalline toxic factor from agenized wheat flour," Nature, 1950, 165: 345-346.

Choi, D.W., "Calcium: still center-stage in hypoxic-ischemic neuronal death," Trends Neurosci., 1995, 18: 58-60.

Cooper, A.J.L., "Role of astrocytes in maintaining cerebral glutathione homeostasis and in protecting the brain against xenobiotics and oxidative stress. In: Glutathione in the Nervous System," Shaw, C.A. (ed.), Taylor and Francis Pub., Washington, 1998, pp. 91-116.

Earnshaw, W.C., "Apoptosis: lessons from in vitro systems," Trends Cell Biol., 1995, 5: 217-220.

Ellis R.E., Yuan, J., and Horvitz, H.R., "Mechanisms and functions of cell death," Ann. Rev. Cell Biol., 1991, 7: 663-698.

Evans, P.H., "Free radicals in brain metabolism and pathology," Br. Med. Bull., 1993, 49: 577-587.

Gavreili, Y., Sherman, Y., and Ben-Sasson, S.A., "Identification of programmed cell death via specific labeling of nuclear DNA fragmentation," J. Cell Biol., 1992, 119:493-501.

Gobe, G., "Apoptosis in brain and gut tissue of mice fed a seed preparation of the cycad Lepidozamia peroffskyana", Biochemical and Biophysical Research Communications, vol. 205, No. 1, 1994, 327-333, XP002199312.

Goding, "Monoclonal Antibodies: Principles and Practice," 1983, New York Academic Press, pp. 98-118.

Haque, M. et al., "Steryl Glycosides: a Characteristic Feature of the *Helicobacter* spp.," J. Bacteriol., 1995, 177: 5334-5337.

Haque, M. et al. "Lipid Profile of *Helicobacter* ssp: Presence of Cholesteryl Glucoside as a Characteristic Feature", J. Bacteriol., Apr. 1996, 178(7): 2065-2070.

Higuchi, Y. and Matsukawa, S., "Glutathione depletion induces giant DNA and high molecular weight DNA fragmentation associated with apoptosis through lipid peroxidation and protein kinase C activation in C6 glioma cells," Arch. Biochem. Biophys., 1999, 363: 33-42.

Hockenbery, D., Oltvai, Z.N., Yin, X.-M., Millian C.L., and Korsmeyer, S.J., "Bcl-2 functions in an antioxidant pathway to prevent apoptosis," Cell, 1993, 75: 241-251.

Janaky, R., Ogita, K., Pasqualotto, B.A., Bains, J.S., Oja, S.S., Yoneda, Y., and Shaw, C.A., "Glutathione and signal transduction in the mammalian CNS," J. Neurochem., 1999, 73: 889-902.

Kalinowska and Wojciechowski, "Purification and Some Properties of Steryl [Beta}-D-Glucoside Hydrolase From Sinapis Alba Seedlings," Phytochemistry, 1978, 17: 1533-1537.

Kastelic-Suhadolc, T., "Cholesteryl Glucoside in Candida Bogoriensis", Biochim Biophys Acta, Nov. 7, 1980, 620(2): 322-325.

Katayama, R., Cheun, M.K., Gorman, L., Tamura, T., and Becker, D.P., "Increase in extracellular glutamate and associated massive ionic fluxes following concussive brain injury," Soc. Neurosci. Abstr., 1998, 14: 1154.

Khabazian I. et al., 2000, "Mechanisms of action of sitosterol glucoside in mammalian CNS", Society for Neroscience Abstracts, vol. 26: 2074, Abstract No. 771.13, XP001070132.

Kohler and Milstein, "Continuous cultures of fused cell secreting antibody of predifined specificity", Nature, 1975, 256: 495-497.

Kohler and Milstein, "Derivation of specific antibody-producing tissue culture and tumor lines by cell fusion," Eur. J. Immunol., 1976, 6: 511-519.

Kunimoto, S. et al., "Expression of cholesteryl glucoside by heat shock in human fibroblasts," Cell Stress Chaperones, Jan. 2000, 5(1): 3-7.

Kurland, "Amyotrophic lateral Sclerosis and Parkinson's disease complex on Guam linked to an environmental toxin," Trends Neurosci., 1988, 11(2): 51-54.

Lepage, M., "Isolation and characterization of an esterified form of steryl glucoside", J Lipid Res, 1964, 5: 587-592.

Mayberry, W. R. et al., "Structures and Properties of Acyl Diglucosylcholesterol and Galactofuranosyl Diacyglycerol from Acholeplasma Axanthum", Biochim Biophys Acta, 1983, 752: 434-443.

Meister, A. and Tate, S.S., "Glutathione and related gamma glutamyl compounds: biosynthesis and utilization," Annu. Rev. Biochem., 1976, 45: 559-604.

Meldrum, B. and Garthwaite, J., "Excitatory amino acid neurotoxicity and neurodegenerative disease," Trends Pharmacol. Sci., 1990, 11: 379-386.

Nagata, S., "Apoptosis by death factor," Cell, 1997, 88: 355-365.

Newell, G. W., Erickson, T.C., Gilson, W.E., Gerschoff, S.N., and Elvehjem, C.A., "Role of "agenized" flour in the production of running fits," J. Am Med Assoc., 1947, 135: 760-763.

Nicole, A., Santiard-Baron, D., Cellballos-Picot, I., "Direct evidence for GSH as mediator of apoptosis in normal cell death," Biomed. Pharmacother., 1998, 52: 349-355.

Palmer, A.M., "The activity of pentose phosphate pathway is increased in response to oxidative stress in Alzheimer's disease," J. Neural Trans., 1999, 106: 317-328.

(56) References Cited

OTHER PUBLICATIONS

Parry et al., "Biochemical characterization and mechanism of action in a thermostable [Beta]-glucosidase purified from Thermoascus aurantiacus", Biochem J, Jan. 1, 2001, 353(Pt 1): 117-127.
Peri, T.M., Bedard, L., Kosatsky, T., Hockin, J.C., Todd, E.C.D., and Remis, R.S. An outbreak of toxic encephalopathy caused by eating muscles contaminated with domoic acid. N. Eng. J. Med. 1990, 322: 1775-1780.
Peterson, G.L., "Review of the Folin phenol protein quantification method of Lowry, Rosebrough, Farr and Randall." Anal. Biochem., 1979, 83: 201-220.
Pow, D.V., Barnett, N.L., and Penfold, P., "Are neuronal glutamate transporters relevant in retinal glutamate homeostatis?" Neurochem. Intl., 2000, 37: 191-198.
Rechcigl, M. and Laqueur, G.L., "Carcinogen-mediated alteration of the rate of enzyme synthesis and degradation," Enzym. Biol. Clin. ,1968, 9: 276-286.
Rechcigl, M., "Rates and kinetics of catalase synthesis and destruction in rats fed cycad and cycasin in vivo," Fed. Proc., 1964, 23: 1376-1377.
Rothstein, J.D., Tsai, G., and Kuncl, R.W., Clawson, L., Cornblath, D.R., Drachman, D.B., Pestronk. A., Staunch, B.L., and Coyle, J.T., "Abnormal excitatory amino acid metabolism in amyotrophic lateral sclerosis," Ann. Neurol., 1990, 28: 18-25.
Rothstein, J.D., Martin, L.J., Kuncl, R.W., "Decreased glutamate transport by the brain and spinal cord in amyotrophic lateral sclerosis," N. Eng. J. Med., 1992, 326: 1464-1468.
Rothstein, J.D., Van Kammen, M., Levey, A., Martin, L.J., and Kuncl, R.W. "Selective loss of glial glutamate transporter GLT-1 in amyotrophic later sclerosis," Ann. Neurol., 1995, 38: 73-84.
Russel, R.L., Siedelak, S.L., Raian, A.K., Bautista, J.M., Smith, M.A., and Perry, G., "Increased neuronal glucose-6-phosphate dehydrogenase and sulfhydryl levels indicate reductive compensation to oxidative stress in Alzheimer's disease," Arch. Biochem. Biophys., 1999, 370: 236-239.
Shaw, C. A., et al., "Did consumption of flour treated by the agene process contribute to the incidence of neurological disease?", Med. Hyp., 1998, 51: 477-481.
Shaw, C. et al., "Identification of a novel excitotoxin from cycad seed: Implications for neuronal disorders," Society for Neuroscience Abstracts, vol. 25, No. 1-2, 1999, 1304, XP001070136.
Shaw, C.A., Bains, J.S., Pasqualoto, B.A., Curry, K., "Methionine sulfoximine shows excitotoxic actions in rat cortical slices," Can. J. Physiol. Pharmacol., 1999a, 77: 871-877.
Shaw, C.A., Pasqualotto, B.A., and Curry, K., "Glutathione-induced sodium currents in neocortex," Neuroreport., 1996, 7: 1149-1152.
Shaw, C.A. (ed.), Glutathione in the Nervous System, Taylor and Francis Pub., Washington, 1998, pp. 117-136.
Shaw, P. J. et al., "Glutamate, excitotoxicity and amyotrophic lateral sclerosis", J. Neurol. 1997, 244 (Suppl. 2): S3-S14.
Sies, H. (Ed.), "Oxidative stress: Oxidants and Antioxidants," Academic Press, New York, 1991, xv-xxii.
Simonian, N.A. and Coyle, J.T., "Oxidative stress in neurodegenerative diseases," Ann. Rev. Pharmacol. Toxicol., 1996, 36: 83-106.
Simpson et al, "Apoptotic and non-apoptotic cell death following MSO and cycad treatments," Soc. Neurosci. Abstr., 2000, 26:261.
Sugawara et al., "Separation and Determination of Glycolipids from Edible Plant Sources by High Performance Liquid Chromatography and Evaporative Light-Scattering Detection", Lipids, 1999, 34: 1231-1237.
Triosh et al, "Cellular and mitochondrial changes in glutamate-induced HT4 neuronal cell death," Neurosci., 2000, 97: 537-541.
Van Huizen et al, "Characterization of muscarinic acetylcholine receptors in rat cerebral cortex slices with concomitant morphological and physiological assessment of tissue viability," Mol. Brain Res., 1989, 5: 59-69.
Venarucci et al, "Free radicals: important cause of pathologies refer to aging," Panmineva Medica., 1999, 41: 335-339.

Watanabe, M., "Developmental regulation of ionotropic glutamate receptor gene expression and functional correlations. In: Receptor Dynamics in Neural Development," Shaw, C.A. (e.d.), CRC Press, Boca Raton, 1996, pp. 73-89.
Wullner et al, "Glutathione depletion and neuronal cell death the role of reactive oxygen intermediates and mitochondrial function," Brain Res., 1999, 826: 52-63.
Zaman and Ratan, "Glutathione and the regulation of apoptosis in the nervous system," Glutathion in the Nervous System, Shaw, C.A. (ed.), Taylor and Francis Pub., Washington, 1998, pp. 117-136.
Zeevalk and Nicklaus, "Mechanisms underlying initiation of excitotoxicity associated with metabolic inhibition," J. Pharm. Exp. Ther., 1990, 257: 870-878.
Osborne R. et al., "The magical and medicinal usage of Stangeria eriopus in South Africa", Journal of Ethnopharmacology, vol. 43, 1994, 67-72, XP001069718.
Hodgson, et al., "A YAC mouse model for Huntington's Disease with full-length mutant huntingtin, cytoplasmic toxicity, and selective striatal neurodegeneration," Neuron, 1999, 23: 181-192.
Joo et al., "Prevention of inflammation-mediated neurotoxicity by Rg3 and its role in microglial activation," *Biol. Pharm. Bull.*, 2008; 31:1392-1396.
Atkinson, "The market outlook for neurodegenerative diseases," *Business Insights*, 2010.
Bove et al., "Toxin-induced models of Parkinson's Disease," *NeuroRx: The Journal of the American Society for Experimental Neuro Therapeutics*, 2005; 2:484-494.
National Center for Biotechnology Information, "Alzheimer's Disease," accessed 2010.
National Center for Biotechnology Information, "Parkinson's Disease," accessed 2010.
National Center for Biotechnology Information, "ALS," accessed 2010.
Rockenstein et al., "Transgenic animal models of neurodegenerative diseases and their application to treatment development," *Advanced Drug Delivery Reviews*, 2007; 59:1093-1102.
Marler et al, 2006, Steryl Igucoside con entration delcines with Cycas micronesica seed age, Functional Plant biology, 33(9): 857-862.
Tabata et al, 2008, Chronic exposure to dietary sterol glucosides is neurotoxic to motor neurons and induces an ALS-PDC phenotype, Neuromolecular Med, 2008, 10(1): 24-39.
Ly et al, 2007, Novel Environmental Toxins: Steryl Glycosides as a Potential Etiological Factor for Age-Related Neurodegenerative Diseases, Journal of Neuroscience Research, 85: 231-237.
International Serach Report/Written Opinion for PCT/CA2009/001543, completed Feb. 3, 2010.
Altschul et al., "Basic local alignment search tool," J. Mol. Biol., 1990; 215:403-10.
Shaw et al., "Analysis of neurological disease in four dimensions: insight from ALS-PDC epidemiology and animal models," Neurosciences and Biobehavioral Reviews, 2003; 27(6):493-505.
Barneoud et al., "Beneficial effects of lysine acetylsalicylate, a soluble salt of aspirin, on motor performance in a transgenic model of amyotrophic lateral sclerosis," *Experimental Neurology*, 1999; 255:243-251.
Karl et al., "Behavioral effects of neuropeptide Y in F344 rat substrains with a reduced dipeptidyl-peptidase IV activity," Pharmacology Biochemistry and Behavior, 2003; 75(4):869-879.
Nasevicius et al., "Effective targeted gene 'knockdown' in zebrafish," Nat Genet., 2000; 26(2):216-20.
Cashman et al., "Neuroblastoma x spinal cord (NSC) hybrid cell lines resemble developing motor neurons," Dev Dyn 1992, 194(3):209-221.
Roy et al., "Glutamate potentiates the toxicity of mutant Cu/Zn-superoxide dismutase in motor neurons by postsynaptic calcium-dependent mechanisms," J. Neurosci., 1998; 18:9673-9684.
Zheng et al., "A novel method for culturing neural stem cells," In Vitro Cell Dev. Biol. Anim., 2007; 43(5-6):155-158.
Tolkatchev D. et al., "Structure dissection of human progranulin identifies well-folded granulin/epithelin modules with unique functional activities," Protein Sci., 2008; 17:711-724.

(56) References Cited

OTHER PUBLICATIONS

Wilson et al, "Decrease in glial glutamate transporter variants and excitatory amino acid receptor down-regulation in a murine model of ALS-PDC," Neuromolecular Medicine, 2003; 3:105-118.
Wilson et al., "Quantitative measurement of neurodegeneration in an ALS-PDC model using MR microscopy," Neuroimage, 2004; 23: 336-343.
Van Damme et al., "Progranulin functions as a neurotrophic factor to regulate neurite outgrowth and enhance survival," J. Cell Biol. Apr. 7, 2008, 181(1):37-41.
Sleegers, K. et al., "Progranulin modifies onset age and survival in Amyotrophic Lateral Sclerosis," Neurology, Mar. 20, 2007, vol. 68, No. 12, Suppl. 1, p. A202, 59$^{th}$ Annual Meeting of the American Academy of Neurology, Boston, MA, USA, Apr. 28-May 5, 2007.
Cruts, M. et al., "Progranulin mutations in Ubiquitin-positive frontotemporal dementia linked to Chromosome 17q21," Current Alzheimer Res. 2006, vol. 3, No. 5, pp. 485-491.
Zhang, Y-J. et al., "Progranulin mediates caspase-dependent cleavage of TAR DNE Binding Protein-43," J. Neuroscience, Sep. 26, 2007, vol. 27, No. 39, pp. 10530-10534.
Rademakers, R. et al., "Granulin precursor," National Center for Biotechnology Information [retrieved Jun. 23, 2009 from Internet: http://www.ncbi.nlm.nih.gov/sviewer/viewer.fcgi?4504151:NCBI:19728484>, GenPept Accession No. NP_002078.
Sambrook et al., "Molecular Cloning: A Laboratory Manual", 3rd Edition, Cold Spring Harbor Laboratory Press, (2001).
Written Opinion of the International Searching Authority for PCT/CA2009/000074, dated Jul. 7, 2009.
He et al., "Progranulin is a mediator of the wound response," *Nature Medicine*, 2003; 9(2):225-229.

\* cited by examiner

NUROTOXIC STEROL GLYCOSIDES

CROSS-REFERENCE TO RELATED APPLICATIONS

This application is a U.S. national application under 37 C.F.R. § 371(b) of International Application Ser. No. PCT/CA2009/001543 filed Oct. 30, 2009, which claims priority under 35 U.S.C. § 119(e) to U.S. Provisional Application Ser. No. 61/110,389, filed Oct. 31, 2008, and U.S. Provisional Application Ser. No. 61/174,707 filed May 1, 2009, the disclosures of which are incorporated herein by reference.

TECHNICAL FIELD

The invention relates to compositions for use in animal models of neurodegenerative disease and methods therefor. More particularly, the invention relates to the use of neurotoxic sterol glycosides or neurotoxic glycolipids, or combinations thereof, in animal models of neurodegenerative disease. Neurotoxicity-modulating chromenols can also be used in these animal models in combination with the neurotoxic sterol glycosides or neurotoxic glycolipids, or combinations thereof.

BACKGROUND AND SUMMARY

The neurodegenerative diseases, Alzheimer's disease (AD), Parkinson's disease (PD), amyotrophic lateral sclerosis (ALS), and amyotrophic lateral sclerosis-parkinsonism dementia complex (ALS-PDC) are typically diagnosed only after behavioral deficits can be detected clinically (Arasaki and Tamaki, 1998; Leenders et al., 1990; Whitehouse et al., 1982). In Alzheimer's disease, neurons are lost from various regions of the cerebral cortex and hippocampus and manifest as the loss of cognitive functions (Odle, 2003). Parkinson's disease involves the degeneration of select portions of the nigral striatal system (Schapira and Olanow, 2003). Initially, terminal projections of dopamine-containing neurons are lost. Eventually, the cell bodies of the dopaminergic neurons are lost from the substantia nigra (SN). This outcome results in disturbance of motor control and induces tremor, hypokinesia and rigidity (Dauer and Przedborski, 2003). Amyotrophic lateral sclerosis at endstage is characterized by the progressive loss of spinal and cortical motor neurons controlling motor function, particularly the diaphragm (Rowland and Shneider, 2001), resulting in paralysis and death.

In each of the aforementioned diseases, relatively specific neuronal populations degenerate and result in particular behavioral outcomes. It is believed that AD, PD, and ALS are distinct diseases, arising from distinct etiologies and resulting in mutually exclusive behavioral and neuropathological outcomes. This view is based on differential primary symptoms and pathological findings. However, more recent work has pointed to considerable cross-over between the neurodegenerative diseases (see Caine and Eisen, 1989; Muchowski and Wacker, 2005). For example, both PD and ALS patients can exhibit a decline in cognitive function which is conventionally an AD attribute (Aarsland et al., 2003; Vaphiades et al., 2002). Also, AD patients can experience tremors, which is a feature primarily associated with PD (Yokoyama et al., 2002). Another overlap between AD and PD is that the gait disturbances experienced by some PD patients are a predictor for developing AD-like dementia (Verghese et al., 2002). ALS and PD have been shown to overlap significantly, and ALS cases with dementia and/or parkinsonism features are accordingly called ALS-plus (Zoccolella et al., 2002).

Assessments of post-mortem AD, PD, and ALS tissue have also uncovered many similarities between these disease states. In particular, the similarities in the molecular mechanisms associated with protein folding and aggregation have been gaining increasing attention (Muchowski and Wacker, 2005). Although the specific proteins that aggregate in particular neurodegenerative diseases are often unrelated in primary amino acid sequence, the characteristic lesions of AD, PD, and ALS typically contain fibrillar, amyloid-like structures with similar biochemical features (Dobson, 2003). However, instances of proteinacious inclusions possessing a common primary amino acid sequence have been observed across disease classifications. For example, neurofibrillary tangles (NFT) which are primarily associated with AD have been identified in some ALS (Kokubo et al., 2000) and PD (Arima et al., 1999) patients. On the same note, α-synuclein, first identified in the amyloid plaques of AD patients, has also been identified in PD Lewy bodies and Lewy neurites (Lucking and Brice, 2000).

Although the age-related diseases, AD, PD and ALS have similarities, the similarities are limited. In contrast, the neurological disease, amyotrophic lateral sclerosis-parkinsonism dementia complex (ALS-PDC) is characterized by a wide range of behavioral and neuropathological attributes shared with each of the age-related diseases and many other neurological diseases. ALS-PDC can express as the classical form of ALS or as a form of parkinsonism with AD features. Moreover, some ALS-PDC patients of Guam or Rota have been observed to present with a combination of these symptoms (Steele and Guzman, 1987). Accordingly, it is believed that understanding ALS-PDC will result in a better understanding of neurological diseases as a whole.

In order to better understand the underlying neurological mechanisms of these disease states at both a cellular level and at the biochemical level, as well as, at the level of the whole animal, animal models of neurodegenerative diseases are needed. Ideally, the animals should display symptoms that approximate the symptoms displayed by humans suffering from these neurodegenerative diseases. The inventors have discovered such animal models and methods for monitoring neurodegenerative diseases in animals using neurotoxic sterol glycosides or neurotoxic glycolipids, or combinations thereof. These neurotoxic sterol glycosides or neurotoxic glycolipids, or combinations thereof, can also be used in combination with neurotoxicity-modulating chromenols.

A non-limiting list of illustrative neurodegenerative diseases that can be modeled using the compositions, methods and models described herein includes amyotrophic lateral sclerosis, early onset Parkinson's disease, late onset Parkinson's disease, Alzheimer's disease, and the like.

In one embodiment, described herein an animal model of a neurodegenerative disease is provided. The animal model comprises a non-human animal in contact with a neurotoxic compound of formula

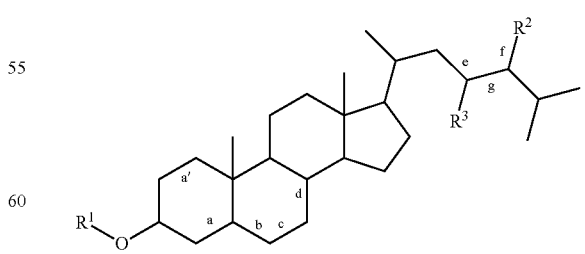

wherein
$R^1$ is optionally substituted glycosyl;
$R^2$ is hydrogen, alkyl, alkenyl, alkynyl, heteroalkyl, haloalkyl, or $OR^4$;

R³ is hydrogen, alkyl, alkenyl, heteroalkyl, haloalkyl, or OR⁴;

R⁴ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; and wherein the neurotoxic compound is not a compound selected from the group consisting of β-sitosterol-β-D-glucoside and cholesterol glucoside.

In another embodiment, described herein an animal model of a neurodegenerative disease is provided. The animal model comprises a non-human animal in contact with a neurotoxic compound of formula

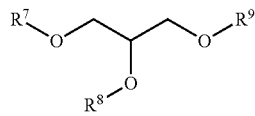

wherein R⁷ and R⁸ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; and R⁹ is glycosyl.

In another embodiment, described herein an animal model of a neurodegenerative disease is provided. The animal model comprises a non-human animal in contact with a neurotoxic compound of formula

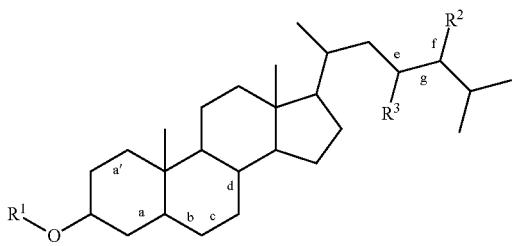

and a neurotoxicity modulating compound of formula

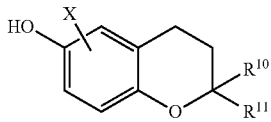

wherein
R¹ is optionally substituted glycosyl;
R² is hydrogen, alkyl, alkenyl, alkynyl, heteroalkyl, haloalkyl, or OR⁴;
R³ is hydrogen, alkyl, alkenyl, heteroalkyl, haloalkyl, or OR⁴;
R⁴ is in each instance independently selected from the group consisting of hydrogen, alkyl, heteroalkyl, haloalkyl, alkenyl, alkynyl, and acyl;
the bonds labeled a, a', b, c, d, e, f, and g are each independently selected from the group consisting of a single bond and a double bond, with the proviso that for the bonds labeled b, c, and d, adjacent bonds are not both double bonds;

R¹⁰ and R¹¹ are each independently selected from the group consisting of alkyl and alkenyl, each of which is optionally substituted;

X is from 0 to 3 substituents selected from the group consisting of halogen, alkyl, and alkoxyl; and wherein the neurotoxic compound is not a compound selected from the group consisting of β-sitosterol-β-D-glucoside and cholesterol glucoside.

In another embodiment, an animal model of a neurodegenerative disease is provided. The animal model comprises a non-human animal in contact with a neurotoxic compound of formula

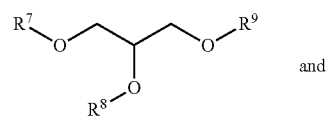

and a neurotoxicity modulating compound of formula

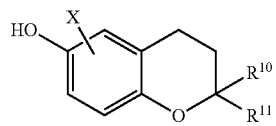

wherein R⁷ and R⁸ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; R⁹ is glycosyl; R¹⁰ and R¹¹ are each independently selected from the group consisting of alkyl and alkenyl, each of which is optionally substituted; and X is from 0 to 3 substituents selected from the group consisting of halogen, alkyl, and alkoxyl is described.

In another embodiment, a method of monitoring a neurodegenerative disease in a non-human animal is provided. The method comprises the steps of administering to the non-human animal a composition comprising a neurotoxic compound of formula

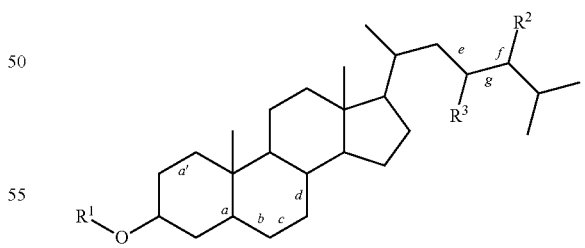

wherein
R¹ is optionally substituted glycosyl;
R² is hydrogen, alkyl, alkenyl, alkynyl, heteroalkyl, haloalkyl, or OR⁴;
R³ is hydrogen, alkyl, alkenyl, heteroalkyl, haloalkyl, or OR⁴;
R⁴ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; and wherein the compound is not a compound selected from the group consisting of β-sitosterol-β-D-glucoside and cholesterol glucoside; and monitoring the neurodegenerative disease in the non-human animal.

In another embodiment, a method of monitoring a neurodegenerative disease in a non-human animal is provided. The method comprises the steps of administering to the non-human animal a composition comprising a neurotoxic compound of formula

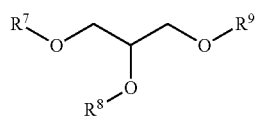

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; $R^9$ is glycosyl; and monitoring the neurodegenerative disease in the non-human animal.

In another embodiment, the method of any one of the preceding embodiments wherein the composition further comprises a neurotoxicity modulating compound is provided. The neurotoxicity modulating compound is of formula

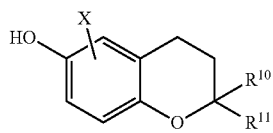

wherein $R^{10}$ and $R^{11}$ are each independently selected from the group consisting of alkyl and alkenyl, each of which is optionally substituted; and X is from 0 to 3 substituents selected from the group consisting of halogen, alkyl, and alkoxyl.

In another embodiment, a neurotoxic composition for use in a model of a neurodegenerative disease is provided. The neurotoxic composition comprises a compound of formula

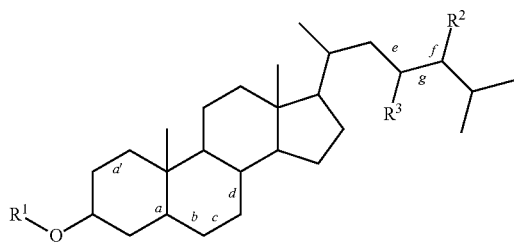

wherein $R^1$ is optionally substituted glycosyl;
$R^2$ is hydrogen, alkyl, alkenyl, alkynyl, heteroalkyl, haloalkyl, or $OR^4$;

$R^3$ is hydrogen, alkyl, alkenyl, heteroalkyl, haloalkyl, or $OR^4$;

$R^4$ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; and wherein the compound is not a compound selected from the group consisting of β-sitosterol-β-D-glucoside and cholesterol glucoside; and a pharmaceutically acceptable carrier therefore.

In another embodiment, a neurotoxic composition for use in a model of a neurodegenerative disease is provided. The neurotoxic composition comprises a compound of formula

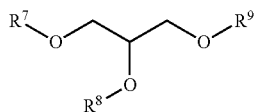

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxy, keto, methoxy, or alkoxyl; $R^9$ is glycosyl; and a pharmaceutically acceptable carrier therefore.

In another embodiment, the neurotoxic composition of any one of the preceding embodiments further comprising a neurotoxicity modulating compound is provided. The neurotoxicity modulating compound is of formula

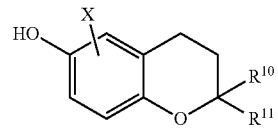

wherein $R^{10}$ and $R^{11}$ are each independently selected from the group consisting of alkyl and alkenyl, each of which is optionally substituted; and X is from 0 to 3 substituents selected from the group consisting of halogen, alkyl, and alkoxyl.

In another embodiment, a compound for use in a model of a neurodegenerative disease is provided. The compound has the formula

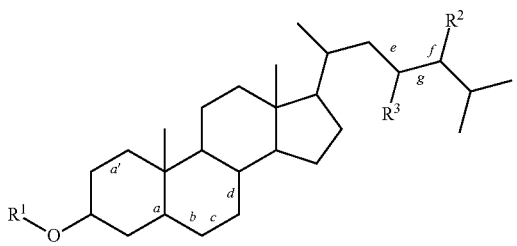

wherein $R^1$ is optionally substituted glycosyl;
$R^2$ is hydrogen, alkyl, alkenyl, alkynyl, heteroalkyl, haloalkyl, or $OR^4$;

$R^3$ is hydrogen, alkyl, alkenyl, heteroalkyl, haloalkyl, or $OR^4$;

$R^4$ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; and wherein the compound is not a compound selected from the group consisting of β-sitosterol-β-D-glucoside and cholesterol glucoside.

In another embodiment, a method for examining neurodegeneration in a non-human animal is provided. The method comprises the step of administering a synthetic neurotoxic sterol glycoside to the animal, wherein the neurotoxic sterol glycoside causes the neurodegeneration in the animal, and wherein the neurodegeneration in the animal is examined by observing behavioral abnormalities in the animal or is examined post-mortem in a central nervous system tissue of the animal. Illustratively, the sterol glycoside can be any of the above-described sterol glycoside neurotoxic compounds, or combination thereof, or any of these compounds in combination with any of the neurotoxicity modulating compounds described above, and the compounds can be isolated (e.g., greater than 90%, 95%, 96%, 97%, 98%, 98.5%, 99%, 99.5%, or 99.7% pure). In all of the above-described embodiments, the neurological degeneration can be identified by a behavioral test selected from the group consisting of a leg extension test, a gait length test, a rotarod test, a wire hang test, a water maze test, a radial arm maze test, a Digigate system test, an Ethovision test, an anxiety test, a depression test, and an olfactory system test. In one aspect, the behavioral abnormality can be an abnormality in motor function or an abnormality in cognitive function. Further, illustratively, the central nervous system tissue examined post-mortem can be from a site selected from the group consisting of the cortex, the hippocampus, the spinal cord, and the substantia nigra. Illustratively, the sterol glycoside can cause neuronal excitotoxicity.

In yet another embodiment, an animal model of neurotoxic sterol glycoside-induced neurodegeneration is provided. The animal model comprises a non-human animal having neurodegeneration caused by administration of a neurotoxic sterol glycoside in an amount sufficient to cause the neurodegeneration in the non-human animal. Illustratively, the sterol glycoside can be any of the above-described neurotoxic compounds, or combination thereof, or the sterol glycoside can be in combination with any of the neurotoxicity modulating compounds described above, and the compounds can be isolated (e.g., greater than 90%, 95%, 96%, 97%, 98%, 98.5%, 99%, 99.5%, or 99.7% pure) and can be synthetic. In this embodiment, the neurological degeneration can be identified by a behavioral test selected from the group consisting of a leg extension test, a gait length test, a rotarod test, a wire hang test, a water maze test, a radial arm maze test, a Digigate system test, an Ethovision test, an anxiety test, a depression test, and an olfactory system test. In one aspect, the behavioral abnormality can be an abnormality in motor function or an abnormality in cognitive function. Further, illustratively, the central nervous system tissue examined post-mortem can be a site selected from the group consisting of the cortex, the hippocampus, the spinal cord, and the substantia nigra. Illustratively, the sterol glycoside can cause neuronal excitotoxicity.

In any of the embodiments described herein, a glycosidic bond in the sterol glycoside can be hydrolyzed prior to administration of the compound to the animal, for example, to determine if hydrolysis of the bond inhibits the neurotoxicity of the sterol glycoside. In these embodiments, the sterol glycoside can be treated with an enzyme that degrades the neurotoxic sterol glycoside prior to administration of the sterol glycoside to the animal. In any of the embodiments described in the application, the sterol glycoside can be non-acylated.

In another embodiment the purity of any of the above-described compounds the compound is greater than 90%, 95%, 96%, 97%, 98%, 98.5%, 99%, 99.5%, or 99.7% pure. Such pure compounds are isolated compounds. In any of the embodiments described herein, the compounds can be synthetic.

In another embodiment, a compound for use in a model of a neurodegenerative disease is provided. The compound has the formula 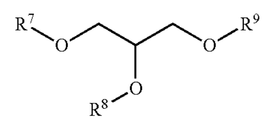 wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxy, keto, methoxy, or alkoxyl; $R^9$ is glycosyl.

In another embodiment, the purity of the compound described in the preceding paragraph is greater than 90%, 95%, 96%, 97%, 98%, 98.5%, 99%, 99.5%, or 99.7% pure. Such pure compounds are isolated compounds. In any of the embodiments described herein, the compounds can be synthetic.

In another embodiment, a neurotoxicity modulating compound is provided. The neurotoxicity modulating compound has the formula 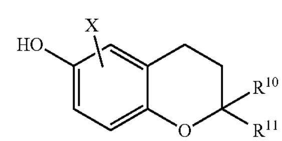 wherein $R^{10}$ and $R^{11}$ are each independently selected from the group consisting of alkyl and alkenyl, each of which is optionally substituted; X is from 0 to 3 substituents selected from the group consisting of halogen, alkyl, and alkoxyl.

In another embodiment, the purity of the compound described in the preceding paragraph is greater than 90%, 95%, 96%, 97%, 98%, 98.5%, 99%, 99.5%, or 99.7% pure. Such pure compounds are isolated compounds. In any of the embodiments described herein, the compounds can be synthetic.

In another embodiment, a neurotoxic composition for use in a fetal exposure model of a neurodegenerative disease is described. The neurotoxic composition comprises a compound of formula

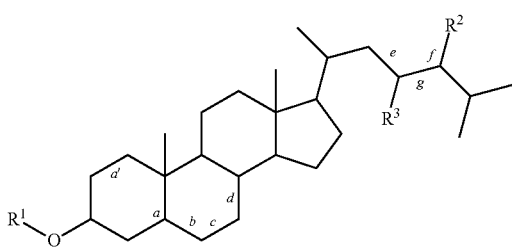

wherein $R^1$ is optionally substituted glycosyl;

$R^2$ is hydrogen, alkyl, alkenyl, alkynyl, heteroalkyl, haloalkyl, or $OR^4$;

$R^3$ is hydrogen, alkyl, alkenyl, heteroalkyl, haloalkyl, or $OR^4$;

$R^4$ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; wherein the non-human animal is a fetal animal; and a pharmaceutically acceptable carrier therefore.

In another embodiment, a neurotoxic composition for use in a model of a neurodegenerative disease is described. The neurotoxic composition comprises a compound of formula

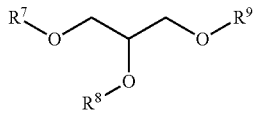

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxy, keto, methoxy, or alkoxyl; $R^9$ is glycosyl; and a pharmaceutically acceptable carrier therefore.

DETAILED DESCRIPTION OF ILLUSTRATIVE EMBODIMENTS

Figure 1:
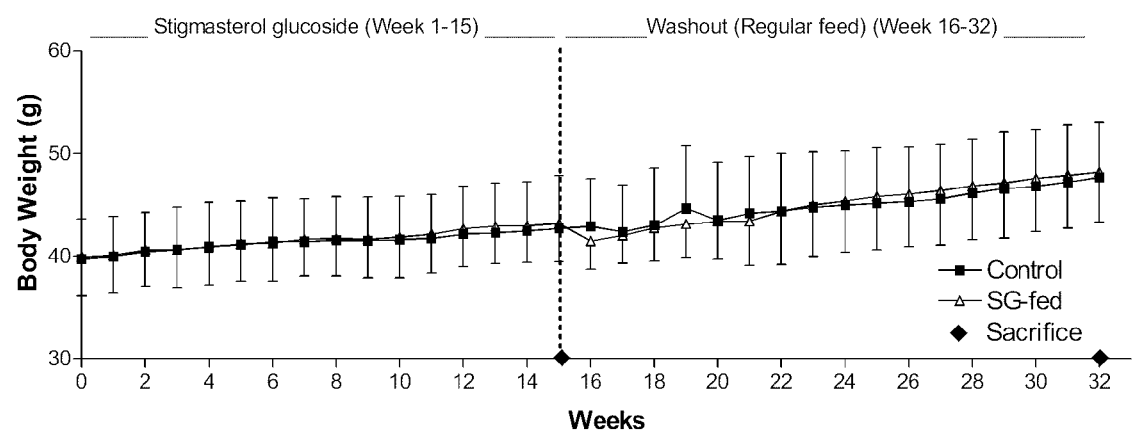
FIG. 1. Body weights of SG-fed animals and their age-matched controls. A comparison of weight values between control and SG-fed animals revealed that body weights are not significantly different between groups and increase steadily over-time.

Each of the publications cited herein is incorporated herein by reference in its entirety.

In one embodiment, described herein is an animal model of a neurodegenerative disease comprising a non-human animal in contact with a neurotoxic compound of formula

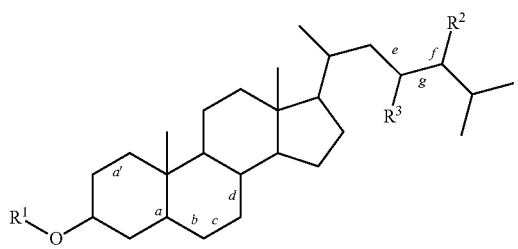

wherein
$R^1$ is optionally substituted glycosyl;
$R^2$ is hydrogen, alkyl, alkenyl, alkynyl, heteroalkyl, haloalkyl, or $OR^4$;
$R^3$ is hydrogen, alkyl, alkenyl, heteroalkyl, haloalkyl, or $OR^4$;
$R^4$ is in each instance independently selected from the group consisting of hydrogen, alkyl, heteroalkyl, haloalkyl, alkenyl, alkynyl, and acyl;
the bonds labeled a, a', b, c, d, e, f, and g are each independently selected from the group consisting of a single bond and a double bond, with the proviso that for the bonds labeled b, c, and d, adjacent bonds are not both double bonds; and wherein the neurotoxic compound is not a compound selected from the group consisting of β-sitosterol-β-D-glucoside and cholesterol glucoside.

In another embodiment, described herein is an animal model of a neurodegenerative disease comprising a non-human animal in contact with a neurotoxic compound of formula

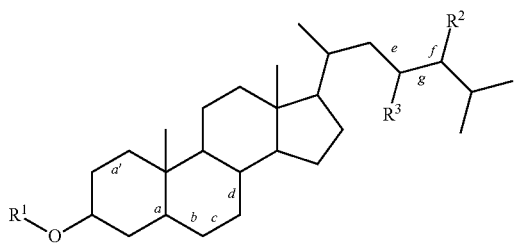

and a neurotoxicity modulating compound of formula

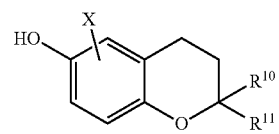

wherein
$R^1$ is optionally substituted glycosyl;
$R^2$ is hydrogen, alkyl, alkenyl, alkynyl, heteroalkyl, haloalkyl, or $OR^4$;
$R^3$ is hydrogen, alkyl, alkenyl, heteroalkyl, haloalkyl, or $OR^4$;
$R^4$ is in each instance independently selected from the group consisting of hydrogen, alkyl, heteroalkyl, haloalkyl, alkenyl, alkynyl, and acyl;
the bonds labeled a, a', b, c, d, e, f, and g are each independently selected from the group consisting of a single bond and a double bond, with the proviso that for the bonds labeled b, c, and d, adjacent bonds are not both double bonds;
$R^{10}$ and $R^{11}$ are each independently selected from the group consisting of alkyl and alkenyl, each of which is optionally substituted;
X is from 0 to 3 substituents selected from the group consisting of halogen, alkyl, and alkoxyl; and wherein the neurotoxic compound is not a compound selected from the group consisting of β-sitosterol-β-D-glucoside and cholesterol glucoside.

In another embodiment, described herein is an animal model of a neurodegenerative disease comprising a non-human animal in contact with a neurotoxic compound of formula

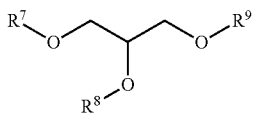

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; and $R^9$ is glycosyl.

In another embodiment, described herein is an animal model of a neurodegenerative disease comprising a non-human animal in contact with a neurotoxic compound of formula

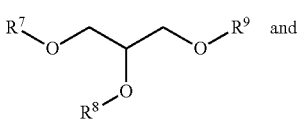 and a neurotoxicity modulating compound of formula

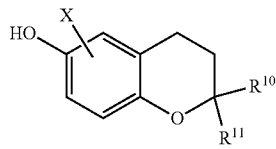

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; $R^9$ is glycosyl;

$R^{10}$ and $R^{11}$ are each independently selected from the group consisting of alkyl and alkenyl, each of which is optionally substituted; and X is from 0 to 3 substituents selected from the group consisting of halogen, alkyl, and alkoxyl.

In another embodiment, the animal model of a neurodegenerative disease of any of the preceding embodiments wherein the neurotoxic compound has the formula

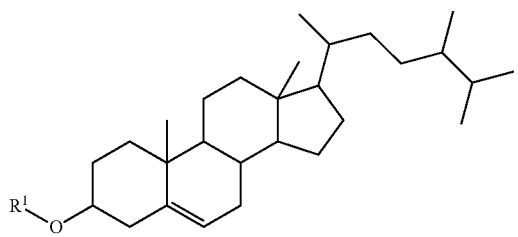

is described.

In another embodiment, the model of any of the preceding embodiments wherein the neurotoxic compound has the formula

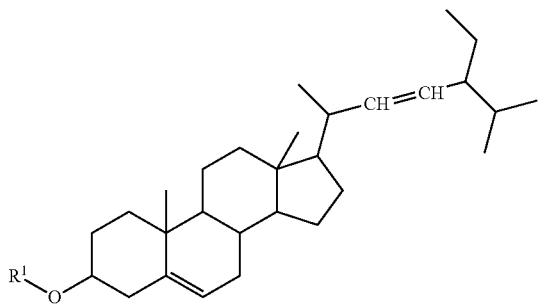

is described.

In another embodiment, the model of any of the preceding embodiments wherein the neurotoxic compound has the formula

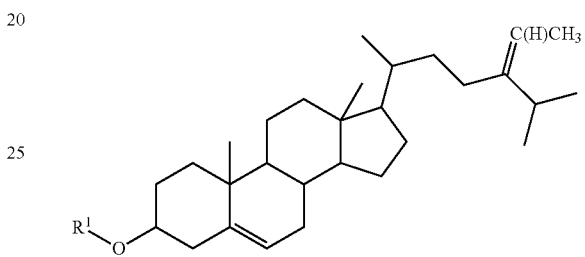

is described.

In another embodiment, the model of any of the preceding embodiments wherein the neurotoxic compound has the formula

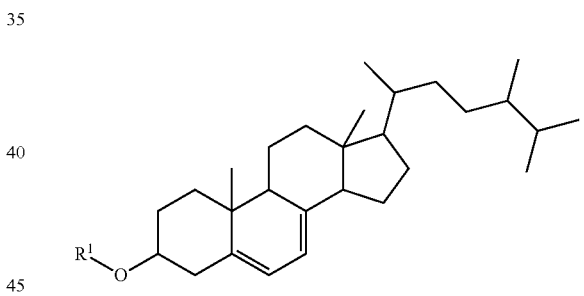

is described.

In another embodiment, described herein is the model of any one of the preceding embodiments wherein $R^1$ is selected from the group consisting of hexosyl and pentosyl, each of which is optionally substituted.

In another embodiment, described herein is the model of any one of the preceding embodiments wherein $R^1$ is selected from the group consisting of hexosyl and pentosyl, each of which is optionally substituted; $R^2$ is methyl or ethyl; and $R^3$ is hydrogen.

In another embodiment, described herein is the model of any one of the preceding embodiments wherein $R^1$ is selected from the group consisting of hexosyl and pentosyl, each of which is optionally substituted; $R^2$ is methyl or ethyl; $R^3$ is hydrogen; and the bond labeled b is a double bond.

In another embodiment, described herein is the model of any one of the preceding embodiments wherein the bond labeled g is a double bond.

In another embodiment, described herein is the model of any one of the preceding embodiments wherein $R^1$ has formula

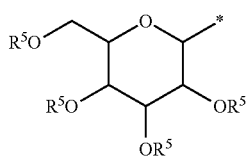

wherein $R^5$ is in each instance independently selected from the group consisting of hydrogen, methyl and $C(O)R^6$, where $R^6$ is alkyl, haloalkyl, or heteroalkyl.

In another embodiment, described herein is the model of any one of the preceding embodiments wherein the $R^1$ is β-D-glucosyl. In another embodiment, described herein is the model of any one of the preceding embodiments wherein the neurotoxic compound is selected from the group consisting of campesterol glucoside, dihydrobrassicasterol glucoside, ergosterol glucoside, and avenasterol glucoside. In another embodiment, described herein is the model of any one of the preceding embodiments wherein the neurotoxic compound is a mixture of two or more of campesterol glucoside, dihydrobrassicasterol glucoside, stigmasterol glucoside, ergosterol glucoside, avenasterol glucoside, or sitosterol glucoside.

In another embodiment, described herein is the model of any one of the preceding embodiments wherein the neurotoxic compound is stigmasterol glucoside. In another embodiment, described herein is the model of any one of the preceding embodiments wherein the neurotoxic compound is campesterol glucoside. In another embodiment, described herein is the model of any one of the preceding embodiments wherein the neurotoxic compound is dihydrobrassicasterol glucoside.

In another embodiment, described herein is a model wherein the animal is contacted with any of the neurotoxic compounds described herein in combination with a neurotoxicity modulating compound. In accordance with the invention, the phrases "in contact with" and the terms "contacting" and "contacted" in reference to the animal mean administering one of the compounds described herein to the animal.

In another embodiment, described herein is the model of any one of the preceding embodiments wherein the $R^9$ is a mono saccharide, a disaccharide, or a trisaccharide. In another embodiment, described herein is the model of any one of the preceding embodiments wherein the $R^9$ is a monosaccharide. In another embodiment, described herein is the model of any one of the preceding embodiments wherein the $R^9$ is a disaccharide.

In another embodiment, described herein is the model of any one of the preceding embodiments wherein one of $R^7$ or $R^8$ is an optionally substituted monounsaturated fatty acid acyl, and the other of $R^7$ or $R^8$ is an optionally substituted polyunsaturated fatty acid acyl.

In another embodiment, described herein is the model of any one of the preceding embodiments wherein the neurotoxicity modulating compound is a tocopherol or a tocotrienol. In another embodiment, described herein is the model of any one of the preceding embodiments wherein the neurotoxicity modulating compound is beta-tocopherol.

In illustrative embodiments, the non-human animal used in the animal model of neurodegenerative disease can be any suitable laboratory animal. For example, the non-human animal can be a rodent, such as a mouse, a rat, a hamster, a guinea pig, a gerbil, and the like. In other embodiments, the non-human animal can be a primate, for example, a monkey, a chimpanzee, a macaque, a squirrel monkey, an ape, or any other primate useful in an animal model of neurodegenerative disease. In other illustrative embodiments, the non-human animal can be a rabbit, a dog, a cat, or any other suitable laboratory animal. In another embodiment, the non-human animal can be a mammal. In another embodiment, the animal can be a pig.

In any one of the preceding embodiments, the neurodegenerative disease can be selected from a variety of disease states. The neurodegenerative disease can be selected from the group consisting of progressive supranuclear palsy, Alzheimer's disease, frontotemporal dementia (e.g., Pick's disease, frontotemporal lobar degeneration, progressive aphasia, and semantic dementia), motor neuron disease (e.g., amyotrophic lateral sclerosis, primary lateral sclerosis, progressive bulbar palsy, pseudobulbar palsy, progressive muscular atrophy, and spinal muscular atrophy), neuropathy, peripheral neuropathy, early onset Parkinson's disease, and late onset Parkinson's disease. In another embodiment of the model described herein, the neurodegenerative disease can be selected from the group consisting of amyotrophic lateral sclerosis, early onset Parkinson's disease, late onset Parkinson's disease, and Alzheimer's disease. In yet another embodiment, the neurodegenerative disease is Alzheimer's disease or Parkinson's disease. Alternatively, in any one of the preceding embodiments the neurodegenerative disease can be amyotrophic lateral sclerosis. In another embodiment, neurodegeneration in general can be studied.

In yet another illustrative embodiment, a method of monitoring a neurodegenerative disease in a non-human animal is provided. The method comprises the steps of administering to the non-human animal a composition comprising a neurotoxic compound of formula

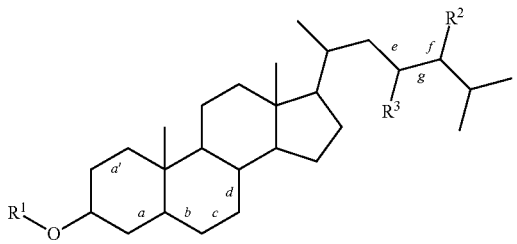

wherein
$R^1$ is optionally substituted glycosyl;
$R^2$ is hydrogen, alkyl, alkenyl, alkynyl, heteroalkyl, haloalkyl, or $OR^4$;
$R^3$ is hydrogen, alkyl, alkenyl, heteroalkyl, haloalkyl, or $OR^4$;
$R^4$ is in each instance independently selected from the group consisting of hydrogen, alkyl, heteroalkyl, haloalkyl, alkenyl, alkynyl, and acyl;
the bonds labeled a, a', b, c, d, e, f, and g are each independently selected from the group consisting of a single bond and a double bond, with the proviso that for the bonds labeled b, c, and d, adjacent bonds are not both double bonds; and wherein the compound is not a compound selected from the group consisting of β-sitosterol-β-D-glucoside and cholesterol glucoside; and monitoring the neurodegenerative disease in the non-human animal.

In another embodiment, a method of monitoring a neurodegenerative disease in a non-human animal is provided. The method comprises the steps of administering to the non-human animal a composition comprising a neurotoxic compound of formula

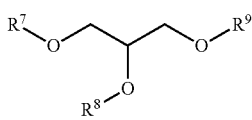

wherein $R^7$ and $R^8$ are each independently selected from the group consisting of saturated fatty acid acyl, monounsaturated fatty acid acyl and polyunsaturated fatty acid acyl, each of which is optionally substituted with halogen, methyl, alkyl, hydroxyl, keto, methoxy, or alkoxyl; $R^9$ is glycosyl; and monitoring the neurodegenerative disease in the non-human animal.

In any one of the preceding embodiments, the neurotoxic composition can further comprise a neurotoxicity modulating compound of formula

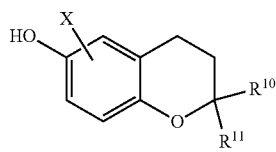

wherein $R^{10}$ and $R^{11}$ are each independently selected from the group consisting of alkyl and alkenyl, each of which is optionally substituted; and X is from 0 to 3 substituents selected from the group consisting of halogen, alkyl, and alkoxyl.

In another embodiment, described herein is the method of any one of the preceding embodiments wherein $R^1$ is selected from the group consisting of hexosyl and pentosyl, each of which is optionally substituted.

In still another embodiment, described herein is the method of any one of the preceding embodiments wherein $R^1$ is selected from the group consisting of hexosyl and pentosyl, each of which is optionally substituted; $R^2$ is methyl or ethyl; and $R^3$ is hydrogen.

In yet another embodiment, described herein is the method of any one of the preceding embodiments wherein $R^1$ is selected from the group consisting of hexosyl and pentosyl, each of which is optionally substituted; $R^2$ is methyl or ethyl; $R^3$ is hydrogen; and the bond labeled b is a double bond.

In another illustrative embodiment, described herein is the method of any one of the preceding embodiments wherein the bond labeled g is a double bond.

In another embodiment, described herein is the method of any one of the preceding embodiments wherein $R^1$ has formula wherein $R^5$ is in each instance independently selected from the group consisting of hydrogen, methyl and $C(O)R^6$, where $R^6$ is alkyl, haloalkyl, or heteroalkyl.

In still another embodiment, described herein is the method of any one of the preceding embodiments wherein the $R^1$ is β-D-glucosyl. In an alternate embodiment, described herein is the method of any one of the preceding embodiments wherein the neurotoxic compound is selected from the group consisting of campesterol glucoside, dihydrobrassicasterol glucoside, ergosterol glucoside, and avenasterol glucoside. Further illustratively, in the method of any one of the preceding embodiments the neurotoxic compound can be a mixture of two or more of campesterol glucoside, dihydrobrassicasterol glucoside, stigmasterol glucoside, ergosterol glucoside, avenasterol glucoside, or sitosterol glucoside. In another embodiment the neurotoxic compound can be selected from the group consisting of stigmasterol glucoside, campesterol glucoside, dihydrobrassicasterol glucoside, ergosterol glucoside, and avenasterol glucoside.

In another illustrative method embodiment, the neurotoxic compound can be stigmasterol glucoside. In another embodiment, described herein is the method of any one of the preceding embodiments wherein the neurotoxic compound is campesterol glucoside. In another method embodiment, the neurotoxic compound can be dihydrobrassicasterol glucoside.

In another embodiment, described herein is the method of any one of the preceding embodiments wherein the $R^9$ is a mono saccharide, a disaccharide, or a trisaccharide. In another embodiment, described herein is the method of any one of the preceding embodiments wherein the $R^9$ is a monosaccharide. In another embodiment, described herein is the method of any one of the preceding embodiments wherein the $R^9$ is a disaccharide.

In any one of the preceding method embodiments one of $R^7$ or $R^8$ can illustratively be an optionally substituted monounsaturated fatty acid acyl, and the other of $R^7$ or $R^8$ is an optionally substituted polyunsaturated fatty acid acyl.

In another embodiment, described herein is the method of any one of the preceding embodiments wherein the neurotoxicity modulating compound is a tocopherol or a tocotrienol. In yet another method embodiment the neurotoxicity modulating compound can be beta-tocopherol.

In illustrative embodiments, the non-human animal used in the method of monitoring a neurodegenerative disease can be any suitable laboratory animal. For example, the non-human animal can be a rodent, such as a mouse (e.g. CD-1 mice, Charles River), a rat (e.g., Sprague-Dawley rats, Charles River), a hamster, a guinea pig, a gerbil, and the like. In other embodiments, the non-human animal can be a primate, for example, a monkey, a chimpanzee, a macaque, a squirrel monkey, an ape, or any other primate useful in the method of monitoring a neurodegenerative disease. In other illustrative embodiments, the non-human animal can be a rabbit, a dog, a cat, or any other suitable laboratory animal. In another embodiment, the non-human animal can be a mammal. In another embodiment, the animal can be a pig.

In any one of the preceding method embodiments, the neurodegenerative disease can be selected from a variety of disease states. The neurodegenerative disease in the methods described herein can be selected from the group consisting of progressive supranuclear palsy, Alzheimer's disease, frontotemporal dementia (e.g., Pick's disease, frontotemporal lobar degeneration, progressive aphasia, and semantic dementia), motor neuron disease (e.g., amyotrophic lateral sclerosis, primary lateral sclerosis, progressive bulbar palsy, pseudobulbar palsy, progressive muscular atrophy, and spinal muscular atrophy), neuropathy, peripheral neuropathy, early onset Parkinson's disease, and late onset Parkinson's disease. In another embodiment of the method described herein, the neurodegenerative disease can be selected from the group consisting of amyotrophic lateral sclerosis, early onset Parkinson's disease, late onset Parkinson's disease, and Alzheimer's disease. In yet another embodiment, the neurodegenerative disease is Alzheimer's disease or Parkinson's disease. Alternatively, in any one of the preceding method embodiments the neurodegenerative disease can be amyotrophic lateral sclerosis. In another embodiment, neurodegeneration in general can be studied.

In any of the preceding embodiments, the non-human animal can be put in contact with the neurotoxic compound or the neurotoxicity modulating compound or the neurotoxic compound or the neurotoxicity modulating compound can be administered to the non-human animal by methods well-known to those skilled in the art. For example, in any one of the preceding embodiments, the composition comprising the neurotoxic compound or the neurotoxicity modulating compound can be administered to the non-human animal or the non-human animal can be put in contact with the neurotoxic compound or the neurotoxicity modulating compound by modifying the non-human animal's daily diet by adding the neurotoxicity compound or the neurotoxicity modulating compound or the composition comprising the neurotoxic compound or the neurotoxicity modulating compound to the diet and feeding the diet to the non-human animal. In addition to the neurotoxic compound or the neurotoxicity modulating compound or the composition comprising the neurotoxic compound or the neurotoxicity modulating compound, other additives can be used to further modify any standard diet for the non-human animal. An illustrative non-limiting list of additives is vitamins, minerals (e.g., calcium and phosphorus), amino acids, emulsifying agents, flavorings, flavor-masking agents, fragrances, antibiotics, anti-parasiticides, anti-nausea agents, protein, fat, fiber, and combinations thereof.

Standard diets for laboratory animals are well-known in the art and, illustratively, any standard pelleted, grain-based diet can be used (e.g., Rodent Diet 20, PicoLab; Teklad Rodent Diet #8064, Harlan Teklad, Madison, Wis.; Mouse Diet™, Purina, St. Louis Mo.; Prolab Rat, Mouse, Hamster 3000, St. Louis Mo.). The animals are typically allowed free access to water.

In other embodiments, the non-human animal can be put in contact with the neurotoxic compound or the neurotoxicity modulating compound or the neurotoxic compound or the neurotoxicity modulating compound can be administered by gavage feeding or parenteral injection in any acceptable carriers such as liquid alcohols, glycols (e.g., polyethylene glycols), glucose solutions (e.g., 5%), esters, amides, sterile water, or buffered saline (including buffers like phosphate or acetate; e.g., isotonic saline). The neurotoxic compound or the neurotoxicity modulating compound can also be administered or the animal can be put in contact with these compounds in the form of a pill, a paste, or a tablet, for example. Additional exemplary components that can be included in the composition along with the neurotoxic compound or the neurotoxicity modulating compound are vegetable oils, gelatin, lactose, amylose, magnesium stearate, solubilizing agents, local anaesthetics (e.g., lidocaine), excipients, preservatives, stabilizers, wetting agents, emulsifiers, salts, and lubricants, depending on the dosage form of the neurotoxic compound or the neurotoxicity modulating compound.

In another embodiment, the composition comprising the neurotoxic compound or the neurotoxicity modulating compound can be administered parenterally and such injections can illustratively be intraperitoneal injections, subcutaneous injections, intramuscular injections, or intravenous injections. In another embodiment, the composition comprising the neurotoxic compound or the neurotoxicity modulating compound can be delivered or administered using a slow pump. Examples of parenteral dosage forms include aqueous solutions of the active agent in well-known pharmaceutically acceptable liquid carriers such as liquid alcohols, glycols (e.g., polyethylene glycols), glucose solutions (e.g., 5%), esters, amides, sterile water, or buffered saline (including buffers like phosphate or acetate; e.g., isotonic saline). In another illustrative aspect, the parenteral dosage form can be in the form of a reconstitutable lyophilizate comprising the dose of the neurotoxic compound. In various aspects, solubilizing agents, local anaesthetics (e.g., lidocaine), excipients, preservatives, stabilizers, wetting agents, emulsifiers, salts, and lubricants can be used.

In various embodiments, the dose of the neurotoxic compound for any of the preceding embodiments can be in the range of about 0.1 mg/kg of animal body weight per day to about 500 mg/kg of animal body weight per day. In another embodiment, the dose of the neurotoxic compound or the neurotoxicity modulating compound can be in the range of about 1.0 mg/kg of animal body weight per day to about 400 mg/kg of animal body weight per day. In other embodiments, the dose of the neurotoxic compound or the neurotoxicity modulating compound can be in the range of about 10 mg/kg of animal body weight per day to about 300 mg/kg of animal body weight per day, about 10 mg/kg of animal body weight per day to about 200 mg/kg of animal body weight per day, about 10 mg/kg of animal body weight per day to about 100 mg/kg of animal body weight per day, or about 10 mg/kg of animal body weight per day to about 50 mg/kg of animal body weight per day.

In any of the preceding embodiments, the composition comprising the neurotoxic compound or the neurotoxicity modulating compound can be administered as single doses, or the doses can be divided and administered as a multiple-dose daily regimen. Further, a staggered regimen, for example, one to six days per week, once per week, or one to three times per month can be used as an alternative to daily administration. Also, daily administration is suitable.

In another embodiment, described herein is the animal model or method of any one of the embodiments described herein wherein the neurodegenerative disease is monitored or studied or examined using any one or more of the behavioral abnormality tests selected from the group consisting of a leg extension test, a gait length test, a rotarod test, a wire hang test, a water maze test, a radial arm maze test, a Digigate system test, an Ethovision test, an anxiety test, a depression test, and an olfactory system test. The procedures for conducting these tests for monitoring and studying neurodegeneration and neurodegenerative diseases are described herein in the EXAMPLES and are well-known to those skilled in the art.

In one aspect, the behavioral abnormality can be an abnormality in motor function or an abnormality in cognitive function. Further, illustratively, the neurodegeneration can be monitored or examined by examining central nervous system tissue post-mortem and the tissue can be from a site selected from the group consisting of the cortex, the hippocampus, the spinal cord, and the substantia nigra. Methods for examining central nervous system tissue post-mortem are well-known in the art and are described in detail in the EXAMPLES section of the application.

Methods for determining and measuring in vivo and in vitro neurotoxic effects on cells and tissues of the nervous system of non-human animals and for studying the behavior of non-human animals exposed to the neurotoxic compounds or the neurotoxicity modulating compounds and compositions described herein are also detailed in WO 2002/37122, the disclosure of which is incorporated by reference herein in its entirety.

In another embodiment, herein described is a neurotoxic composition for use in a model of a neurodegenerative disease comprising a compound of formula

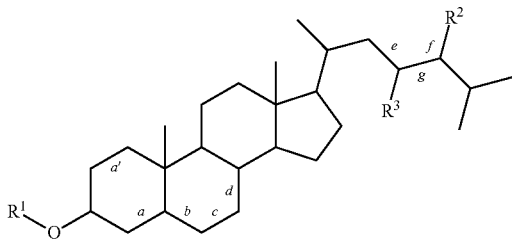

wherein

R$^1$ is optionally substituted glycosyl;

R$^2$ is hydrogen, alkyl, alkenyl, alkynyl, heteroalkyl, haloalkyl, or OR$^4$;

R$^3$ is hydrogen, alkyl, alkenyl, heteroalkyl, haloalkyl, or OR$^4$;

R$^4$ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds; and wherein the compound is not a compound selected from the group consisting of β-sitosterol-β-D-glucoside and cholesterol glucoside; and a pharmaceutically acceptable carrier therefore.

In another embodiment, herein described is a neurotoxic composition for use in a model of a neurodegenerative disease comprising a compound of formula

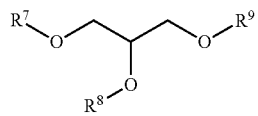

wherein

R$^7$ and R$^8$ are each independently selected from the group consisting of saturated fatty acid acyl, monounsaturated fatty acid acyl and polyunsaturated fatty acid acyl, each of which is optionally substituted with halogen, methyl, alkyl, hydroxy, keto, methoxy, or alkoxyl; R$^9$ is glycosyl; and a pharmaceutically acceptable carrier therefore.

In another embodiment, herein described is a neurotoxic composition of any one of the preceding claims further comprising a neurotoxicity modulating compound of formula

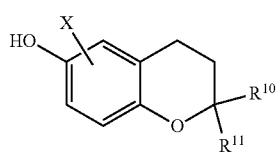

wherein

R$^{10}$ and R$^{11}$ are each independently selected from the group consisting of alkyl and alkenyl, each of which is optionally substituted; and X is from 0 to 3 substituents selected from the group consisting of halogen, alkyl, and alkoxyl.

In another embodiment, described herein is the neurotoxic composition of any one of the preceding embodiments wherein R$^1$ is selected from the group consisting of hexosyl and pentosyl, each of which is optionally substituted.

In another embodiment, described herein is the neurotoxic composition of any one of the preceding embodiments wherein R$^1$ is selected from the group consisting of hexosyl and pentosyl, each of which is optionally substituted; R$^2$ is methyl or ethyl; and R$^3$ is hydrogen.

In another embodiment, described herein is the neurotoxic composition of any one of the preceding embodiments wherein R$^1$ is selected from the group consisting of hexosyl and pentosyl, each of which is optionally substituted; R$^2$ is methyl or ethyl; R$^3$ is hydrogen; and the bond labeled b is a double bond.

In another embodiment, described herein is the neurotoxic composition of any one of the preceding embodiments wherein the bond labeled g is a double bond.

In another embodiment, described herein is the neurotoxic composition of any one of the preceding embodiments wherein R$^1$ has formula

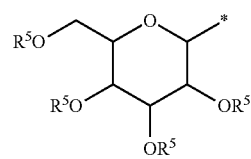

wherein R$^5$ is in each instance independently selected from the group consisting of hydrogen, methyl and C(O)R$^6$, where R$^6$ is alkyl, haloalkyl, or heteroalkyl.

In another embodiment, described herein is the neurotoxic composition of any one of the preceding embodiments wherein the $R^1$ is β-D-glucosyl. In another embodiment, described herein is the neurotoxic composition of any one of the preceding embodiments wherein the neurotoxic compound is selected from the group consisting of campesterol glucoside, dihydrobrassicasterol glucoside, ergosterol glucoside, and avenasterol glucoside. In another embodiment, described herein is the neurotoxic composition of any one of the preceding embodiments wherein the neurotoxic compound is a mixture of two or more of campesterol glucoside, dihydrobrassicasterol glucoside, stigmasterol glucoside, ergosterol glucoside, avenasterol glucoside, or sitosterol glucoside. In another embodiment the neurotoxic compound can be selected from the group consisting of stigmasterol glucoside, campesterol glucoside, dihydrobrassicasterol glucoside, ergosterol glucoside, and avenasterol glucoside.

In another embodiment, described herein is the neurotoxic composition of any one of the preceding embodiments wherein the neurotoxic compound is stigmasterol glucoside. In another embodiment, described herein is the neurotoxic composition of any one of the preceding embodiments wherein the neurotoxic compound is campesterol glucoside. In another embodiment, described herein is the neurotoxic composition of any one of the preceding embodiments wherein the neurotoxic compound is dihydrobrassicasterol glucoside.

In another embodiment, described herein is the neurotoxic composition of any one of the preceding embodiments wherein the $R^9$ is a mono saccharide, a disaccharide, or a trisaccharide. In another embodiment, described herein is the neurotoxic composition of any one of the preceding embodiments wherein the $R^9$ is a monosaccharide. In another embodiment, described herein is the neurotoxic composition of any one of the preceding embodiments wherein the $R^9$ is a disaccharide.

In another embodiment, described herein is the neurotoxic composition of any one of the preceding embodiments wherein one of $R^7$ or $R^8$ is an optionally substituted monounsaturated fatty acid acyl, and the other of $R^7$ or $R^8$ is an optionally substituted polyunsaturated fatty acid acyl.

In another embodiment, described herein is the neurotoxic composition of any one of the preceding embodiments where the neurotoxicity modulating compound is a tocopherol or a tocotrienol. In another embodiment, described herein is the neurotoxic composition of any one of the preceding embodiments wherein the neurotoxicity modulating compound is beta-tocopherol.

In any one of the preceding composition embodiments, the neurodegenerative disease can be selected from a variety of disease states. The neurodegenerative disease can be selected from the group consisting of progressive supranuclear palsy, Alzheimer's disease, frontotemporal dementia (e.g., Pick's disease, frontotemporal lobar degeneration, progressive aphasia, and semantic dementia), motor neuron disease (e.g., amyotrophic lateral sclerosis, primary lateral sclerosis, progressive bulbar palsy, pseudobulbar palsy, progressive muscular atrophy, and spinal muscular atrophy), neuropathy, peripheral neuropathy, early onset Parkinson's disease, and late onset Parkinson's disease. In another embodiment of the compositions described herein, the neurodegenerative disease can be selected from the group consisting of amyotrophic lateral sclerosis, early onset Parkinson's disease, late onset Parkinson's disease, and Alzheimer's disease. In yet another embodiment, the neurodegenerative disease is Alzheimer's disease or Parkinson's disease. Alternatively, in any one of the preceding composition embodiments the neurodegenerative disease can be amyotrophic lateral sclerosis.

In other embodiments, the neurotoxic composition can be in a form for gavage feeding or parenteral injection in any acceptable carriers such as liquid alcohols, glycols (e.g., polyethylene glycols), glucose solutions (e.g., 5%), esters, amides, sterile water, or buffered saline (including buffers like phosphate or acetate; e.g., isotonic saline). Gauage feeding or parenteral injection is considered administration. The neurotoxic composition can also administered be in the form of a pill, a paste, or a tablet, for example. Additional exemplary components that can be included in the composition along with the neurotoxic compound or the neurotoxicity modulating compound are vegetable oils, gelatin, lactose, amylose, magnesium stearate, solubilizing agents, local anaesthetics (e.g., lidocaine), excipients, preservatives, stabilizers, wetting agents, emulsifiers, salts, and lubricants, depending on the dosage form of the neurotoxic composition. In accordance with this invention, the phrase "pharmaceutically acceptable carrier" means any of these carriers or components or any other pharmaceutically acceptable carriers known in the art.

In another embodiment, the composition comprising the neurotoxic compound or the neurotoxicity modulating compound can be injected parenterally and such injections can illustratively be intraperitoneal injections, subcutaneous injections, intramuscular injections, or intravenous injections. In another embodiment, the composition comprising the neurotoxic compound or the neurotoxicity modulating compound can be delivered or administered using a slow pump. Examples of parenteral dosage forms include aqueous solutions of the active agent in well-known pharmaceutically acceptable liquid carriers such as liquid alcohols, glycols (e.g., polyethylene glycols), glucose solutions (e.g., 5%), esters, amides, sterile water, or buffered saline (including buffers like phosphate or acetate; e.g., isotonic saline). In another illustrative aspect, the parenteral dosage form can be in the form of a reconstitutable lyophilizate comprising the dose of the neurotoxic compound or the neurotoxicity modulating compound. In various aspects, solubilizing agents, local anaesthetics (e.g., lidocaine), excipients, preservatives, stabilizers, wetting agents, emulsifiers, salts, and lubricants can be used.

In various embodiments, the dose of the neurotoxic compound or the neurotoxicity modulating compound in the compositions of any of the preceding embodiments can be in the range of about 0.1 mg/kg of animal body weight per day to about 500 mg/kg of animal body weight per day. In another embodiment, the dose of the neurotoxic compound or the neurotoxicity modulating compound can be in the range of about 1.0 mg/kg of animal body weight per day to about 400 mg/kg of animal body weight per day. In other embodiments, the dose of the neurotoxic compound or the neurotoxicity modulating compound can be in the range of about 10 mg/kg of animal body weight per day to about 300 mg/kg of animal body weight per day, about 10 mg/kg of animal body weight per day to about 200 mg/kg of animal body weight per day, about 10 mg/kg of animal body weight per day to about 100 mg/kg of animal body weight per day, or about 10 mg/kg of animal body weight per day to about 50 mg/kg of animal body weight per day.

In any of the preceding embodiments, the composition comprising the neurotoxic compound or the neurotoxicity modulating compound can be administered as single doses, or the doses can be divided and administered as a multiple-dose daily regimen. Further, a staggered regimen, for example, one to six days per week, once per week, or one to three times per month can be used as an alternative to daily administration. Also, daily administration is suitable.

In one illustrative embodiment, the neurotoxic compound or the neurotoxicity modulating compound is synthetic. In one aspect of the invention, the neurotoxic compounds or the neurotoxicity modulating compound described herein can be prepared by methods known in the art from commercially available sterols. An illustrative example is disclosed in US 2006/0252705A1, the disclosure of which is incorporated by reference herein in its entirety. In another aspect, the compounds can be prepared by total or partial synthesis according to methods well-known in the art. Illustrative examples are disclosed by Nagatsu et al., Bioorg. and Medicinal Chem. Vol. 4, 1619-1622, 1994; Ohta et al., Chem. Pharm., Vol 39, 1337-1339, 1991; Shibuya et al. Chem. Pharm., Vol. 40, 1166-1169, 1992, each of which is incorporated by reference herein in its entirety. Exemplary synthesis methods are also described in the EXAMPLES section of the application.

In another embodiment, herein described is any one of the preceding embodiments where the neurotoxic compound or the neurotoxicity modulating compound is purified. Purification of the neurotoxic compound or the neurotoxicity modulating compound can be carried out by any conventional techniques known to those skilled in the art, such as, gel filtration, ion exchange chromatography, column chromatography, affinity chromatography, solvent-solvent extraction, molecular distillation, crystallization, ultrafiltration, and HPLC. Illustratively, the purification of β-sitosterol β-D-glucoside, campesterol β-D-glucoside, dihydrobrassicasterol β-D-glucoside, stigmasterol β-D-glucoside, and b-sitosterol β-D-glucoside is described in Khabazian, I., et al, Journal of Neurochemistry, 2002, 82, 516-528; the disclosure of which is incorporated by reference herein in its entirety. The neurotoxic compound or the neurotoxicity modulating compound can be greater than 90%, 95%, 96%, 97%, 98%, 98.5%, 99%, 99.5%, or 99.7% pure, for example. Such pure compounds are isolated compounds. In any of the embodiments described herein, the compound can be synthetic.

In any of the above-described embodiments, the non-human animal in contact with the neurotoxic compound or the neurotoxicity modulating compound can be a fetal animal. In this aspect of the invention, the administration of the neurotoxic compound or the neurotoxicity modulating compound to the fetal animal in contact with the neurotoxic compound or the neurotoxicity modulating compound can occur through administration of the neurotoxic compound or the neurotoxicity modulating compound to a pregnant female animal, and through the consequent "administration" to the fetal animal by fetal exposure to the body fluids of the pregnant female animal. In this embodiment, post-natal neurodegeneration can be monitored in the young animal (i.e., the neurotoxic compound or the neurotoxicity modulating compound is administered to the fetus by administration to the pregnant female animal and neurodegeneration can be monitored in the post-natal animal (e.g., a pup)). In this fetal exposure embodiment, the young animal that is monitored for neurodegeneration can be a male animal or a female animal.

In this embodiment, the purity of the neurotoxic compound or the neurotoxicity modulating compound used for fetal exposure can be greater than 90%, 95%, 96%, 97%, 98%, 98.5%, 99%, 99.5%, or 99.7% pure. Such compounds are isolated compounds. In this embodiment, the compound can be synthetic. In this illustrative embodiment for fetal exposure, the neurotoxic compound or the neurotoxicity modulating compound can be any of the compounds described herein including any compound selected from the group consisting of stigmasterol glucoside, campesterol glucoside, dihydrobrassicasterol glucoside, ergosterol glucoside, avenasterol glucoside, and combinations thereof. In this fetal exposure embodiment, the neurotoxic compound can also be selected from the group consisting of β-sitosterol-β-D-glucoside and cholesterol glucoside, or these compounds in combination with any one of stigmasterol glucoside, campesterol glucoside, dihydrobrassicasterol glucoside, ergosterol glucoside, avenasterol glucoside, and combinations thereof.

In another embodiment, a method for examining neurodegeneration in a non-human animal is provided. The method comprises the step of administering a synthetic neurotoxic sterol glycoside to the animal, wherein the neurotoxic sterol glycoside causes the neurodegeneration in the animal, and wherein the neurodegeneration in the animal is examined by observing behavioral abnormalities in the animal or is examined post-mortem in a central nervous system tissue of the animal. Illustratively, the sterol glycoside can be any of the above-described sterol glycoside neurotoxic compounds, or combination thereof, or any of these compounds in combination with any of the neurotoxicity modulating compounds described above, and the compounds can be isolated (e.g., greater than 90%, 95%, 96%, 97%, 98%, 98.5%, 99%, 99.5%, or 99.7% pure). In all of the above-described embodiments, the neurological degeneration can be identified by a behavioral test selected from the group consisting of a leg extension test, a gait length test, a rotarod test, a wire hang test, a water maze test, a radial arm maze test, a Digigate system test, an Ethovision test, an anxiety test, a depression test, and an olfactory system test. In one aspect, the behavioral abnormality can be an abnormality in motor function or an abnormality in cognitive function. Further, illustratively, the central nervous system tissue examined post-mortem can be from a site selected from the group consisting of the cortex, the hippocampus, the spinal cord, and the substantia nigra. Illustratively, the sterol glycoside can cause neuronal excitotoxicity.

In yet another embodiment, an animal model of neurotoxic sterol glycoside-induced neurodegeneration is provided. The animal model comprises a non-human animal having neurodegeneration caused by administration of a neurotoxic sterol glycoside in an amount sufficient to cause the neurodegeneration in the non-human animal. Illustratively, the sterol glycoside can be any of the above-described neurotoxic compounds, or combination thereof, or the sterol glycoside can be in combination with any of the neurotoxicity modulating compounds described above, and the compounds can be isolated (e.g., greater than 90%, 95%, 96%, 97%, 98%, 98.5%, 99%, 99.5%, or 99.7% pure) and can be synthetic. In this embodiment, the neurological degeneration can be identified by a behavioral test selected from the group consisting of a leg extension test, a gait length test, a rotarod test, a wire hang test, a water maze test, a radial arm maze test, a Digigate system test, an Ethovision test, an anxiety test, a depression test, and an olfactory system test. In one aspect, the behavioral abnormality can be an abnormality in motor function or an abnormality in cognitive function. Further, illustratively, the central nervous system tissue examined post-mortem can be a site selected from the group consisting of the cortex, the hippocampus, the spinal cord, and the substantia nigra. Illustratively, the sterol glycoside can cause neuronal excitotoxicity.

In any of the embodiments described herein, a glycosidic bond in the sterol glycoside can be hydrolyzed prior to administration of the compound to the animal, for example, to determine if hydrolysis of the bond inhibits the neurotoxicity of the sterol glycoside. In these embodiments, the sterol glycoside can be treated with an enzyme that degrades the neurotoxic sterol glycoside prior to administration of the sterol glycoside to the animal. In any of the embodiments described in the application, the sterol glycoside can be non-acylated.

In an illustrative embodiment, a process for forming neurotoxic compounds described herein of the formula I is described,

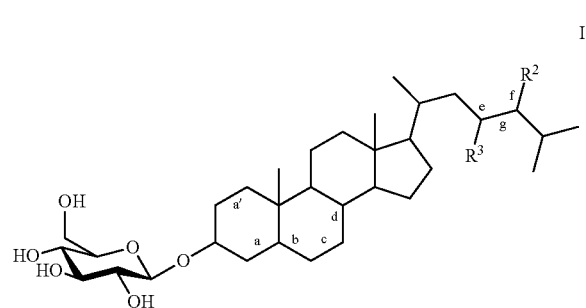

the process comprising the step of contacting D-glucose with pivaloyl chloride, wherein $R^2$ is hydrogen, alkyl, alkenyl, alkynyl, heteroalkyl, haloalkyl, or $OR^4$;

$R^3$ is hydrogen, alkyl, alkenyl, heteroalkyl, haloalkyl, or $OR^4$;

$R^4$ is in each instance independently selected from the group consisting of hydrogen, alkyl, heteroalkyl, haloalkyl, alkenyl, alkynyl, and acyl;

the bonds labeled a, a', b, c, d, e, f, and g are each independently selected from the group consisting of a single bond and a double bond, with the proviso that for the bonds labeled b, c, and d, adjacent bonds are not both double bonds;

In another illustrative embodiment, a process is described for forming neurotoxic compounds described herein of the formula I, the process comprising the step of contacting β-D-glucose pentapivaloate with a mixture of HBr/HOAc to form a first intermediate, and contacting the first intermediate with $Ag_2CO_3$ in an mixture of water and a solvent to form 2,3,4,6-tetra-O-pivaloyl-β-D-glucopyranose.

In another illustrative embodiment, a process is described for forming neurotoxic compounds described herein of the formula I, the process comprising the step of contacting 2,3,4,6-tetra-O-pivaloyl-β-D-glucose with trichloroacetonitrile and a base to form 2,3,4,6-tetra-O-pivaloyl-α-D-glucopyranosyl trichloroacetimidate.

In another illustrative embodiment, a process is described for forming neurotoxic compounds described herein of the formula I, the process comprising the step of contacting the a sterol of formula II with 2,3,4,6-tetra-O-pivaloyl-α-D-glucopyranosyl trichloroacetimidate in the presence of boron trifluoride etherate in a dry solvent to form a compound of formula III wherein P is pivaloyl.

In another illustrative embodiment, a process is described for forming neurotoxic compounds described herein of the formula I, the process comprising the step of contacting the a sterol of formula III with sodium methoxide in methanol.

In yet another embodiment, a process is described for forming neurotoxic compounds described herein of the formula I, the process comprising two or more of the preceding process embodiments in any combination.

Certain of the compounds described herein contain one or more chiral centers, or may otherwise be capable of existing as multiple stereoisomers. The scope of the present invention includes pure stereoisomers as well as mixtures of stereoisomers, such as enantiomers, diastereomers, and enantiomerically or diastereomerically enriched mixtures. Certain of the compounds described herein may be capable of existing as geometric isomers. The scope of the present invention includes pure geometric isomers or mixtures of geometric isomers.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also encompasses the explicit exclusion of one or more of any of the group members.

Additional features of the present invention will become apparent to those skilled in the art upon consideration of the following detailed description of illustrative embodiments.

EXAMPLE 1

Animals

Mice:
Five-month old male CD-1 mice (30.1-35.7 g, 7.5 cm-8.8 cm) were purchased from Charles River (Wilmington, Mass.). Adult mice were chosen to mimic the mean age of onset of ALS-PDC (Kurland, L. T. (1988a) Trends Neurosci. 11, 51-4; Kurland, L. T., et al. (1994) Amyotrophic lateral sclerosis-parkinsonism-dementia complex on Guam: epidemiologic and etiological perspectives. 109-131). Thirty mice for the SG study were randomly divided into 2 groups (14 control and 16 experimental animals). All animals were housed singly in a virus-free barrier facility in a room maintained at 22° C. under a 12 hour light/dark cycle. The mice were provided ad libitum access to food and water.

EXAMPLE 2

Feeding Protocols

Feeding:
The synthetic SG was mixed with finely ground Purina Chow mouse pellets (Mouse Diet™, Purina) to create the experimental pellets with a SG content of 1000 µg per pellet. Dry materials were blended with a sterile silicon spatula. For every 5 g of standard feed, 2.5 mL of doubly-distilled water (dd)H2O was added and the dough was kneaded and round up into pellets. A single sterol glucoside containing pellet was placed in the feeding tray each morning before the addition of regular mouse chow (ad libitum). All experimental pellets were entirely consumed by the mice each day. Control mice were fed standard mouse chow pellets of identical weight with no additives. SG feeding was conducted daily for 15 weeks and mice were behaviorally monitored until sacrifice at 35 weeks (time point 1) or 52 weeks (time point 2). The animals in both groups showed normal weight gain. See FIG. 1

EXAMPLE 3

Behavioral Tests

Behavioral Monitoring:
General conditions: The mice were tested singly in each of the behavioral experiments between 10 a.m. and 5 p.m. under standard light conditions (Crawley, J. N. (2000) What's Wrong With My Mouse?: Behavioral Phenotyping of Trangenic and Knockout Mice. 65-69) in the virus-free facility. The testing sequence of mice was randomized across groups at every session. The experimental group to which each animal belonged was unknown to the observer at the time of behavioral recording.

Figure 2:
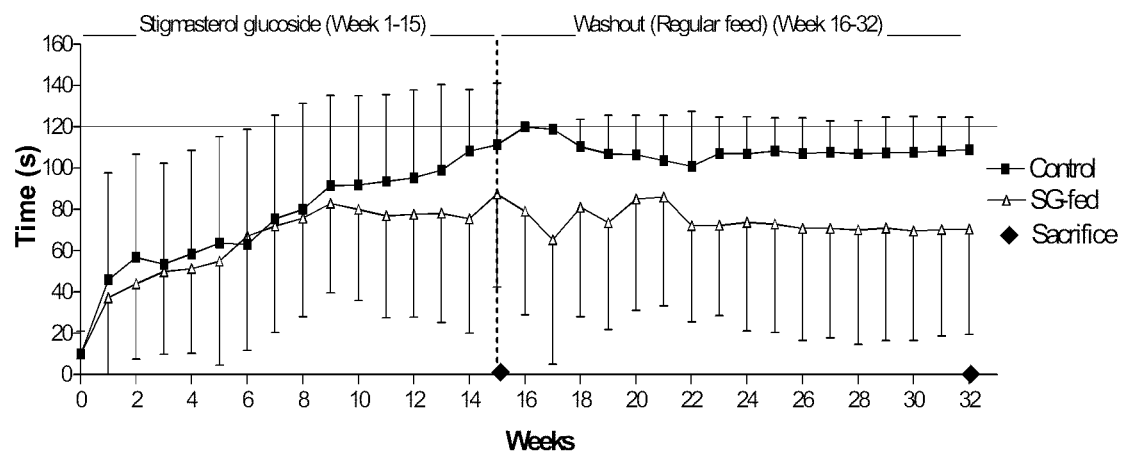
FIG. 2. SG-feeding reduces rotarod performance. The rotarod test was used for the duration of the study to monitor motor coordination of the animals. SG-exposed animals demonstrated a trend of diminished performance on the rotarod but numbers did not reach statistical significance.
Figure 15:
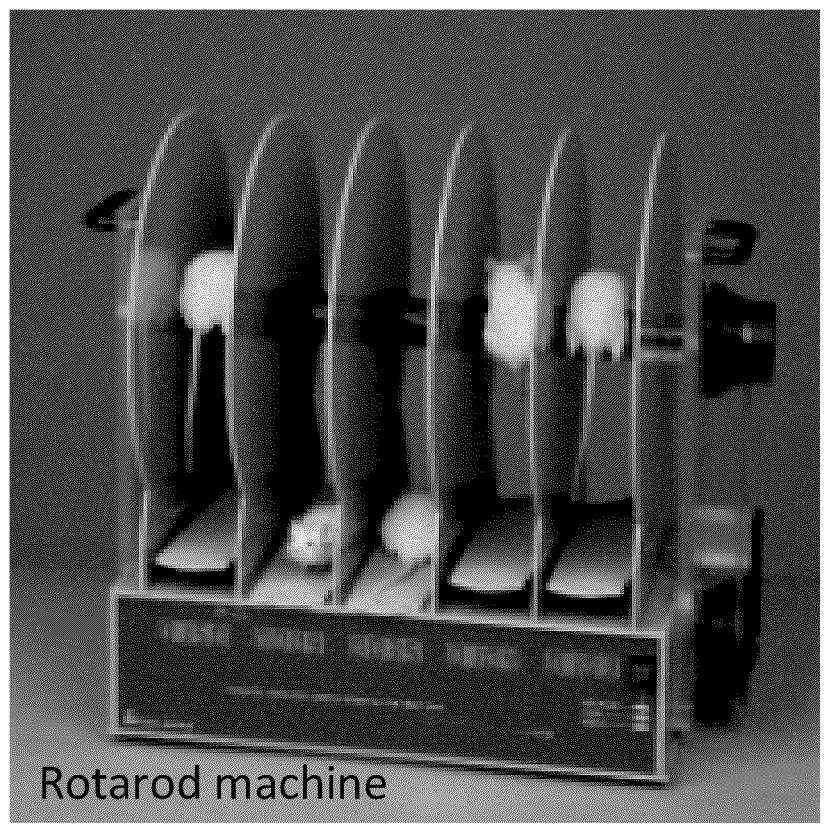
FIG. 15. A rotorod apparatus is used to measure the time mice can remain walking on a horizontal, rotating axle (3.6 cm diameter; 16 rpm) elevated above an area of padding without falling, clenching on, or jumping off the axle.
Figure 16:
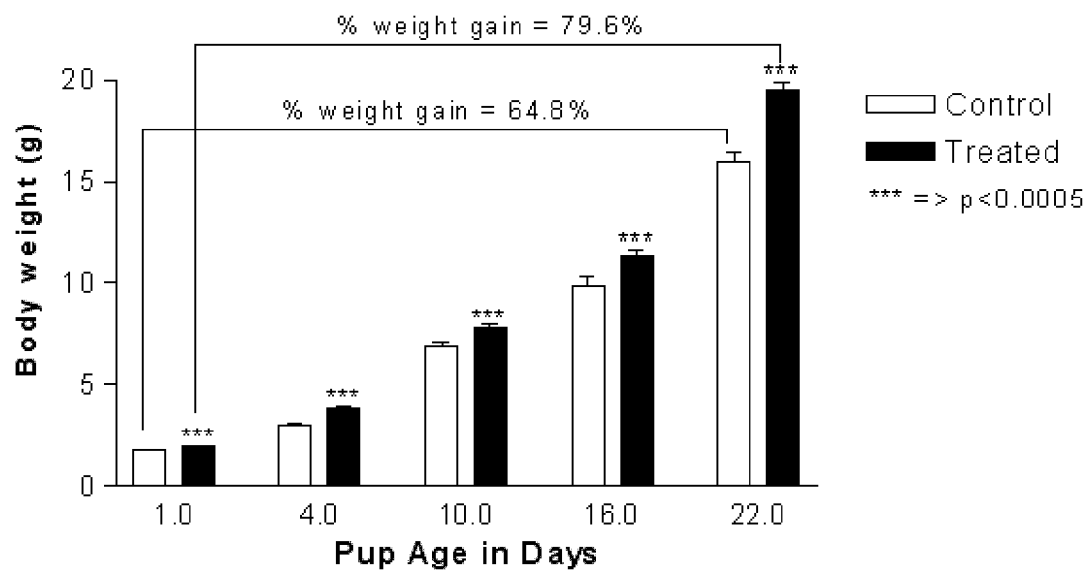
FIGS. 16-18. Body weights of animals exposed to SG and BSSG during gestation and their age matched controls. Pregnant mice were fed food pellets each containing substantially 0.4 mg of SG and 0.6 mg of BSSG, and their pups were weighed at various time intervals after birth. Body weight differences were observed in the SG and BSSG-fed pups (the "treated animals") and the control group, as well as between male treated animals and female treated animals. Treated animals maintained significantly higher body weights than control animals during the period beginning on day 1 through to day 22 following birth (Student's t-test: ***p<0.0005) (FIG. 16), and male treated animals maintained significantly higher body weights than male control animals during the period beginning on week 5 through week 17 post weaning (Student's t-test: *p<0.05, p<0.005, *p<0.0005) (FIG. 17). Treated animals gained 79.6% of their body weight, compared to control animals which gained 64.8% of their body weight, during the period beginning on day 1 through to day 22 following birth (Student's t-test: ***p<0.0005) (FIG. 16). Further, male treated animals gained 139.4% of their body weight, compared to male control animals which gained 109.8% of their body weight, during the period beginning on week 5 through to week 17 post weaning (Student's t-test: *p<0.05, p<0.005, *p<0.0005) (FIG. 17). In comparison, female treated animals gained 101.8% of their body weight (compared to female control animals which gained 83% of their body weight) during the period beginning on week 5 through to week 17 post weaning ((Student's t-test: *p<0.05, **p<0.005) (FIG. 18). Following week 17 after birth, the treated animals and control animals were separated into individual cages ("S" denotes age (in weeks) when the animals were separated into single cages): following separation, body weight losses were observed in female treated animals, female control animals (FIG. 18) and male control animals, but not in male treated animals (FIG. 17).
Figure 17:
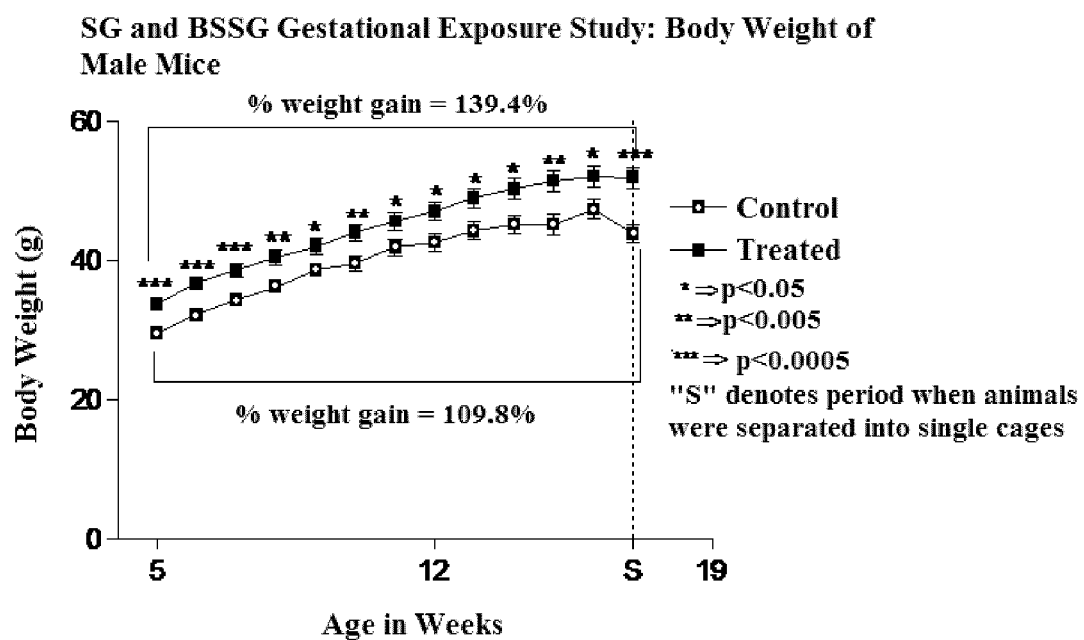
Figure 18:
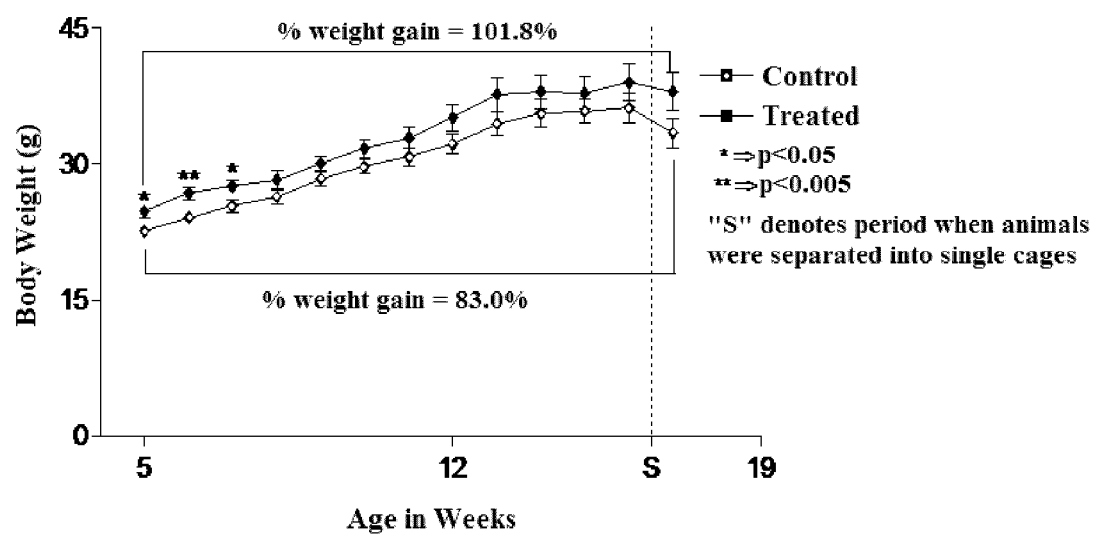
Figure 19:
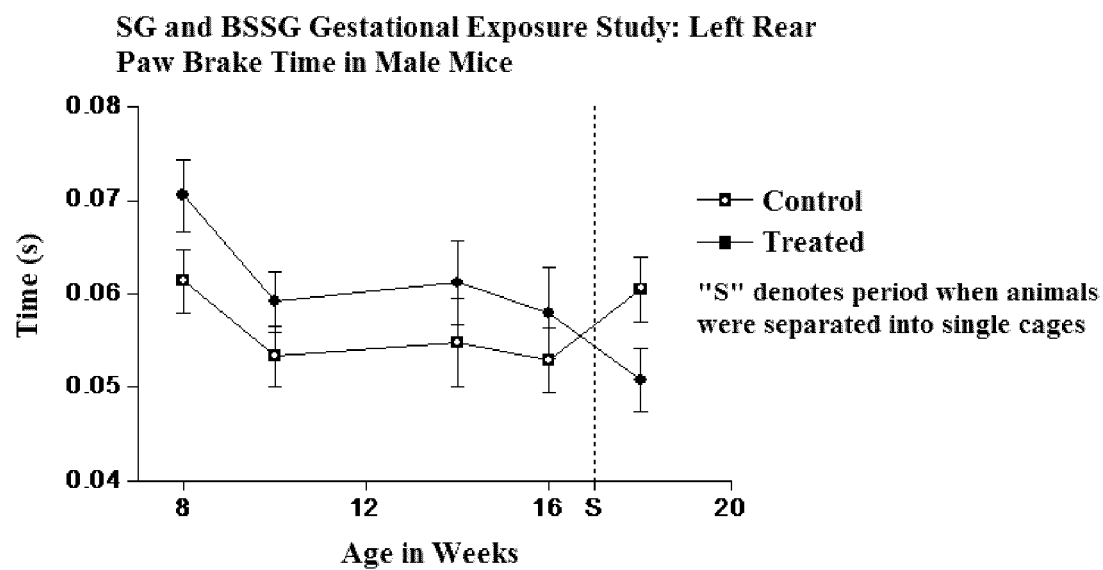
FIGS. 19-26. Male animals exposed to SG and BSSG during gestation demonstrated reduced performance in gait analysis tests compared to male age matched controls. Pregnant mice were fed food pellets each containing substantially 0.4 mg of SG and 0.6 mg of BSSG. Their male pups were tested, at various time intervals during the period beginning on 8 weeks through to 18 weeks following birth, for left and right fore paw and rear paw brake time, and left and right fore paw and rear paw stance duration. As compared to male control animals, the male treated animals demonstrated increased brake times in the left rear paw (FIG. 19) and right rear paw (FIG. 20), and significantly increased brake times in the left fore paw (Student's t-test: *p<0.05) (FIG. 21) and the right fore paw (Student's t-test: *p<0.05) (FIG. 22). Further, male treated animals compared to male control animals demonstrated increased stance duration in the right fore paw (FIG. 24) and significantly increased stance duration in the left fore paw (Student's t-test: *p<0.05) (FIG. 23), left rear paw (Student's t-test: *p<0.05, **p<0.005) (FIG. 25), and right rear paw (Student's t-test: *p<0.05, **p<0.005)(FIG. 26).
Figure 20:
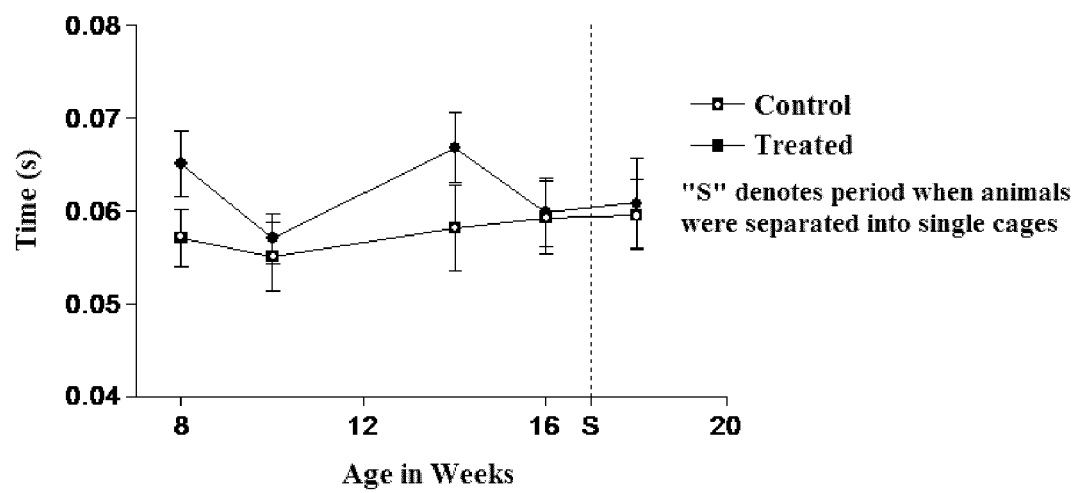
Figure 21:
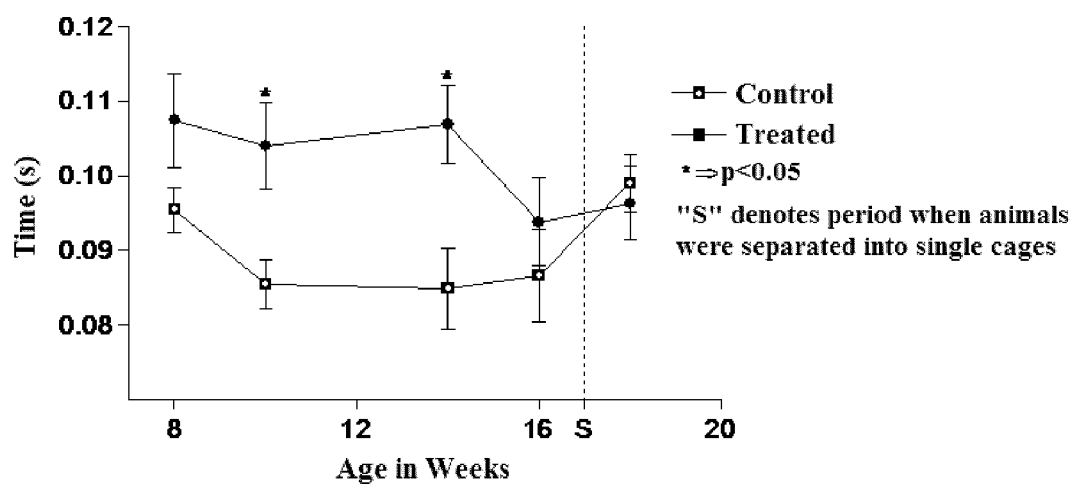
Figure 22:
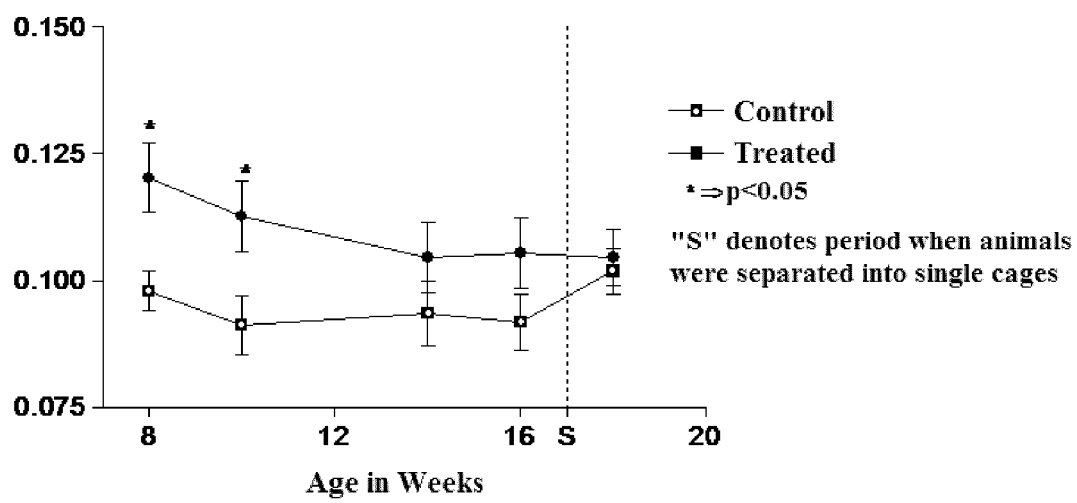
Figure 23:
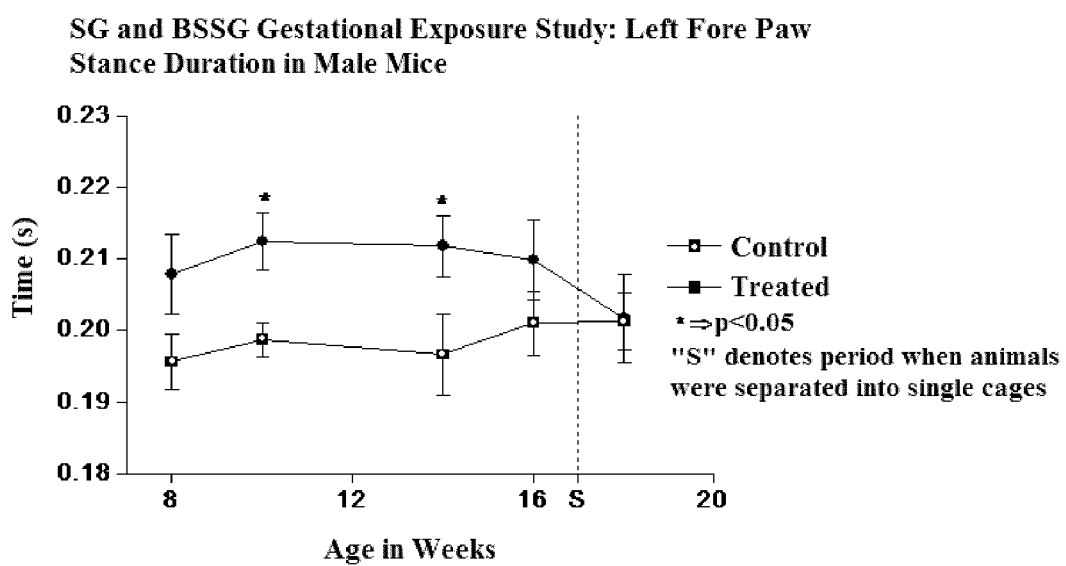
Figure 24:
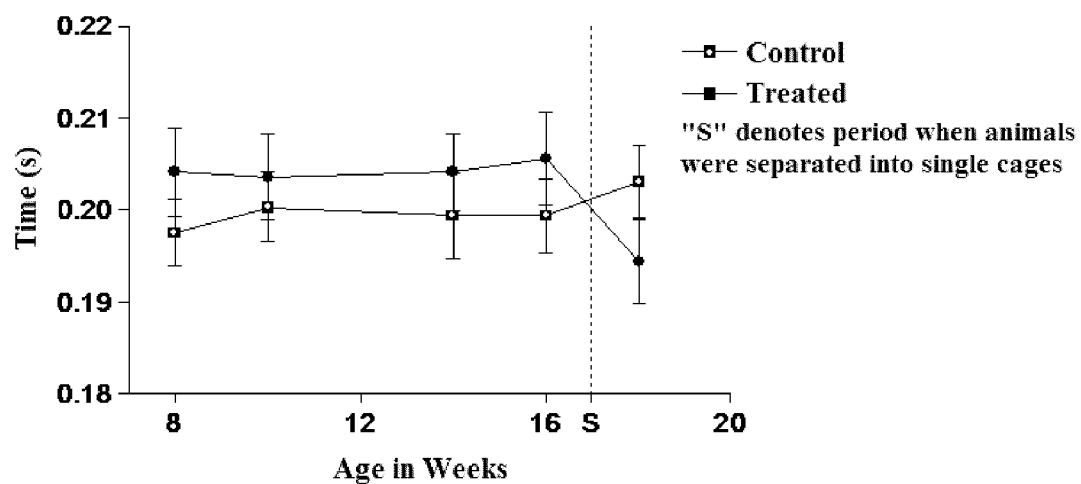
Figure 25:
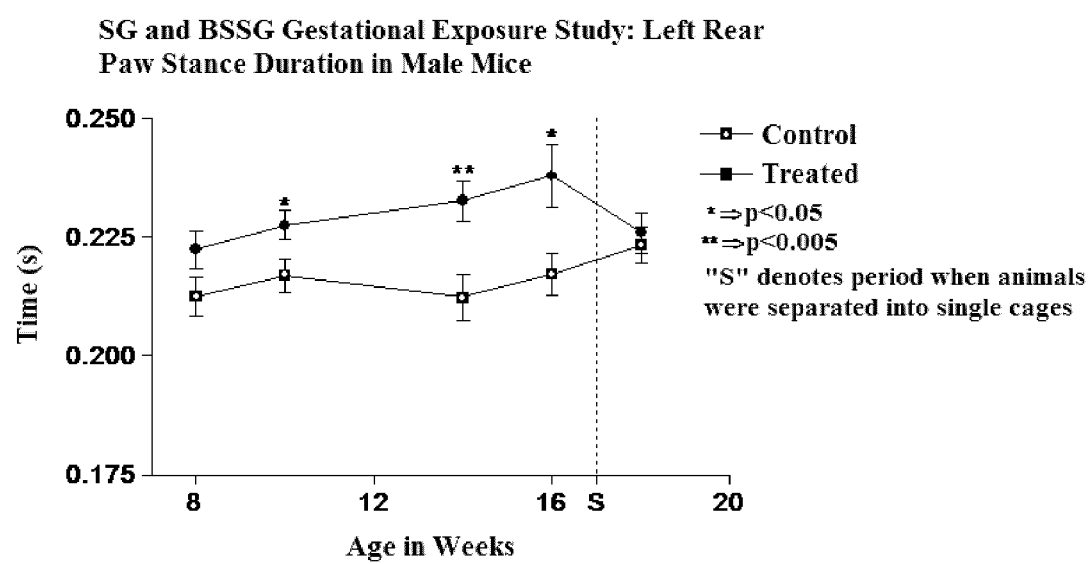
Figure 26:
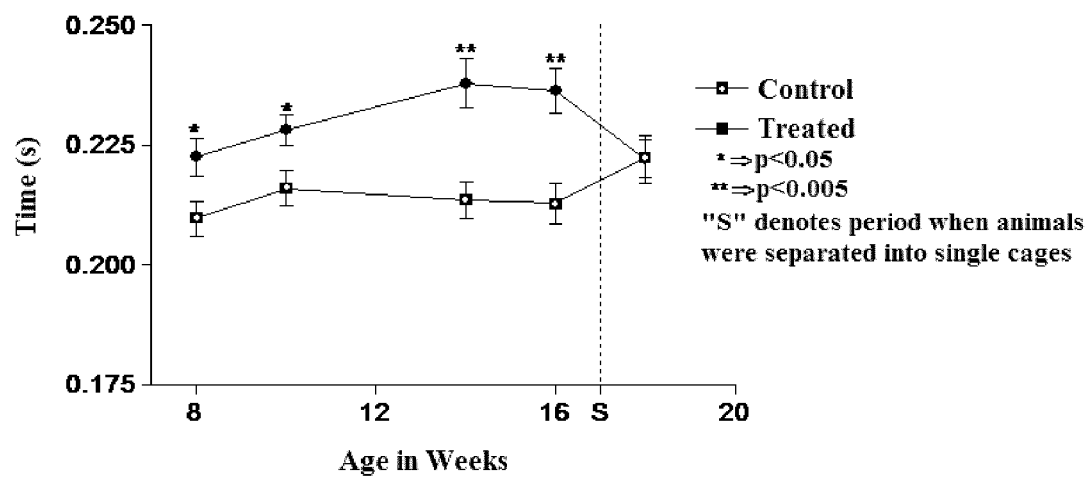

Rotorod: The rotarod was used to evaluate motor function, coordination and balance (Jones, B. J., et al. (1968) Naunyn Schmiedebergs Arch Exp Pathol Pharmakol. 259, 211; Sango, K., et al. (1995) Nat Genet. 11, 170-6; Gerlai, R., et al. (1996) Neurobiol Learn Mem. 66, 143-54; Sango, K., et al. (1996) Nat Genet. 14, 348-52; Chapillon, P., et al. (1998) Behav Brain Res. 93, 77-81; Carter, R. J., et al. (1999) J Neurosci. 19, 3248-57; Crawley, J. N. (1999) Brain Res. 835, 18-26; Gerlai et al., 1996). The time that a mouse could remain walking on a horizontal (Norflus, F., et al. (1998) J Clin Invest. 101, 1881-8), rotating axle (3.6 cm diameter; 16 rpm) elevated above an area of padding without falling, clenching on, or jumping off the axle was measured (Crawley, 1999), see FIG. 15. Each mouse was placed in the center of the rod (Chen, C., et al. (1995) Cell. 83, 1233-42) and tested for a maximum of 160 seconds (Barneoud, P., et al. (1999) Exp Neurol. 155, 243-51; Crawley, 1999) twice per week. The SG fed mice showed a decrease in the time without fall, see FIG. 2.

Figure 4:
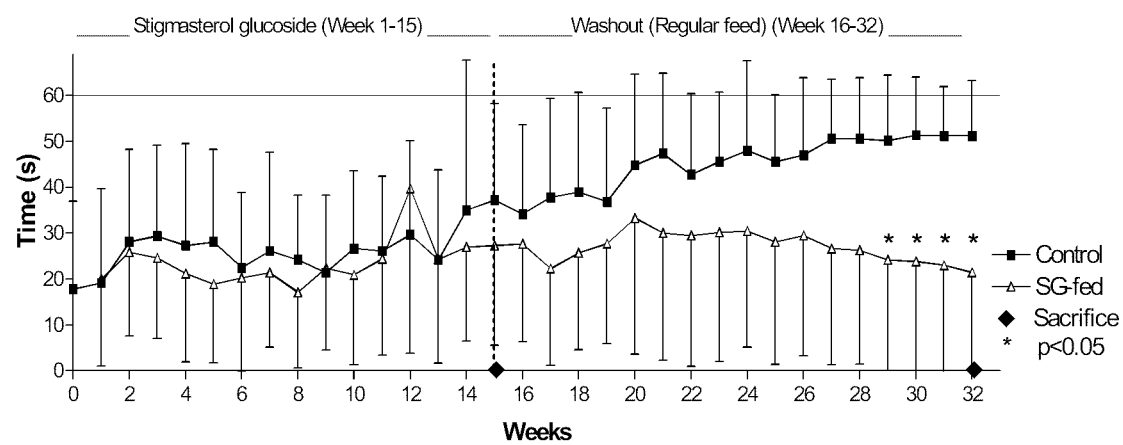
FIG. 4. SG-feeding reduces performance in a forelimb strength analysis test. The wirehang test was used to monitor muscle strength in SG-fed animals and their age-matched controls for the duration of the study. A decline in performance was evident prior to the first animal sacrifice (35 weeks) and by fourteen weeks post-feeding, the difference in performance was statistically significant (t-test: *p<0.05) and remained so until the time the remaining mice were sacrificed.

Wire hang: Neuromuscular strength was tested by the wire hang (or hanging wire) test (Wilson, J., et al. (2003d) Neuromolecular Med. 3, 105-18; Wilson, J. M., et al. (2004c) Neuroimage. 23, 336-43; Wilson, J. M., et al. (2005) Soc Neurosci. Abstr. online; Tabata, R. C., et al. (2008) Neuromolecular Med. 10, 24-39). Both balance and grip strength are required for a mouse to keep its body suspended (Crawley, 2000). Mice were placed on a wire cage lid elevated 50 cm above a soft landing surface. The latency to fall off the wire (maximum 60 seconds) (Sango et al., 1996) was measured from the moment the wire apparatus was inverted (180°). Wire hang testing was conducted biweekly. The control group showed an increase in the time between inversion of the apparatus and falling, while the SG fed mice did not. See FIG. 4.

Figure 3:
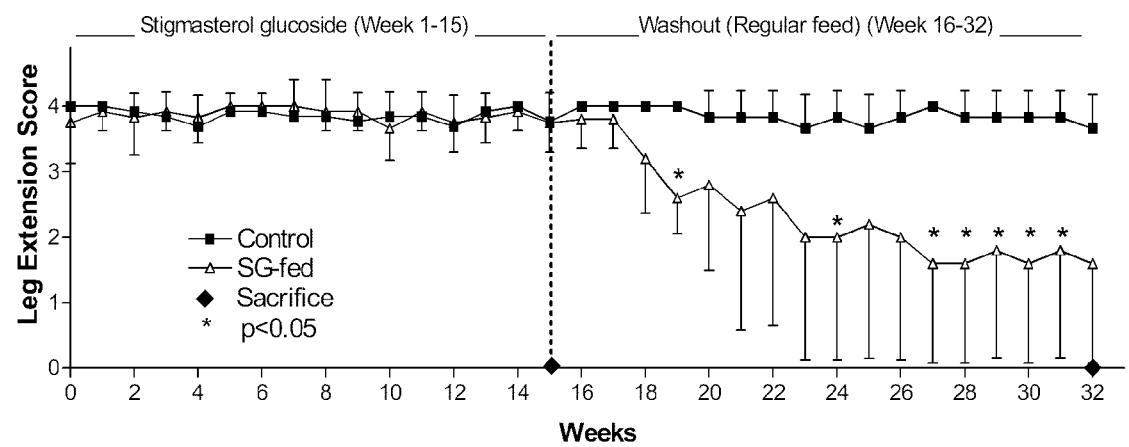
FIG. 3. SG-feeding induces a decline in performance on the leg extension reflex test. The leg extension reflex test was used to monitor hind limb reflex in SG-exposed animals and their age-matched controls for the duration of the study. A steady decline in performance was evident amongst SG-fed animals soon after the first animal sacrifice (35 weeks). Time points at which the performance was found to be significant are marked with an asterisk (t-test: *p<0.05). In contrast, control animals showed no disturbance in hind limb reflex for the duration of the study.

Leg extension reflex test: The leg extension reflex test was used as a measure of motor neuron dysfunction (Barneoud et al., 1999). An altered form of this was used to discriminate more subtle behavioral changes. A 0-4 scale developed with consideration of possible animal responses was utilized (Wilson, J. M., et al. (2002a) Neuromolecular Med. 1, 207-21): A score of 4 was assigned to an animal that exhibited complete extension of both legs. Such a response was considered a normal response. A score of 3 was assigned when an animal extended both legs with some tremors and/or punching of one leg. A score of 2 indicated that the animal extended one leg and retracted the other, or that the animal exhibited tremors in both legs. A score of 1 indicated that the animal retracted one leg and exhibited tremors in the other leg. A score of 0 was assigned when both legs were retracted. The leg extension reflex was measured three times per week in each animal. This scaled test was designed to show the progressive loss of function as the normal reflex has been found to deteriorate progressively to tremor and then to total retraction in previous cycad and sterol glucoside studies (Wilson, J. M., et al. (2002b) Neuromolecular Med. 1, 207-21; Tabata et al., 2008). The leg extension score decreased for the SG-fed mice during the study, see FIG. 3.

Open field monitoring: Spontaneous activity in an open field is considered one of the most standardized general measures of motor function (Crawley, 2000). The open field test can also reveal stress response in animals (i.e. defensive burying or thigmotaxis) (Karl et al., Exp Toxicol Pathol., 2003, 55(1):69-83). Open field testing of each animal was conducted every two weeks. A single mouse was placed in one of four round open field arena/tubs (approximately 1 m diameter) to permit the testing of four animals per 5 minute trial. Five minutes has been shown to be sufficient for evaluation of gross abnormalities in locomotion and highly significant hyperactivity or behavioral sedation (Crawley, 2000). Large arenas were employed since they have better defined "regions" (i.e. center and perimeter) and permit mice to cover longer distances and demonstrate a wider variation in movement. This in turn, increases the likelihood of detection of fear-based behavior (Crawley, 2000) and minimizes habituation of the animal to the open field (Crawley, 2000). Testing arenas were cleaned with 70% ethanol before the testing of each animal and with quatricide at the end of each testing session. Movements were recorded using a video camera mounted on the ceiling. Video clips were reviewed and were manually scored or automatically analysed on an automated video tracking software (Ethovision® 3.1, Noldus Information Technologies Inc., Leesburg, Va., USA). Scoring was done on videotaped sessions, rather than in-person at the time of testing to avoid the introduction of confounding variables by the presence of an observer in close proximity to the mice (Crawley, 2000).

Gait analysis: In order to examine spatial and temporal indices of front and hind limb stepping patterns during forward locomotion, mice were required to run on a colorless (PVC and polycarbonate), straight, level, walled motorized belt (Digigait™, treadmill motor: DC, HP; torque 451b-in, Mouse Specifics, Inc., Boston, Mass., USA) set at 30 rpm with a no-flicker light source (90-250 VAC; 25 kHZ, Mouse Specifics, Inc., Boston, Mass., USA) and camera mounted ventrally (relative to the animal) to facilitate continuous ventral plane videography (up to 150 frames per second) of activity. Gait indices were analyzed with the complementary digital imaging software (Digigait™, Mouse Specifics, Inc., Boston, Mass., USA) as per manufacturer's instructions. Briefly, the software converts "paw prints" into a digital signal and generates a temporal record of paw placement and breaks down the digital file into three main parameters: stride duration, swing duration, and stance duration. The stance duration is the period during which the paw of a limb is in contact with the belt surface. The software further subdivides the stance duration into two components: braking duration (the increase in paw contact area over a discrete time interval) and propulsion duration (the decrease in paw contact area over a discrete time interval). The swing duration is the period of time that a paw is not in contact with the belt surface. In addition to these factors, over a dozen additional characteristics, including stance factor, step-sequence pattern, propulsion, and cadence are generated to provide a spreadsheet format report of twenty-five gait indices.

EXAMPLE 4

Organ Harvesting and Cryosectioning

Mice were sacrificed for histological analysis at 35 weeks (35.9-48.6 g) and 52 weeks (41.2-51.4 g) of age. Age-matched control mice from each time point were included for comparison. The mice were deeply anaesthetized in a chamber with 4% isoflurane and perfused intracardially with filtered PBS (pH 7.4) until the effluent was cleared of blood (2 minutes), followed by perfusion with cold (4° C.) 4% paraformaldehyde (PFA) in 0.1 M phosphate buffer (pH 7.4) for 5 minutes (30 mL). The PBS and the PFA were delivered through separate sterile platinum-cured silicon tubing (Cole-Parmer Canada Inc., Montreal, Canada) and peristaltic pumps (MasterFlex peristaltic pump, Cole-Parmer Canada Inc., Montreal, Canada). The brains and spinal cords were dissected out and fixed overnight at 4° C. and equilibrated in increasing concentrations of sucrose in phosphate-buffered saline, pH 7.4 (10, 20, and 25%) over a 3-day period. Complete equilibration of the tissues was taken as the moment the tissues sank to the bottom of the scintillation tubes filled with 25% sucrose. After equilibration, the spinal cord and brain specimens were set in molds (Tissue-tek Cryomold, Sakura Finetek, USA, Torrance, Calif.) with an optimum cutting temperature (OCT) gel-sucrose mixture frozen by immersion in an isopentane (BDH Laboratory Supplies, UK) bath on dry ice and stored at −80° C. until processing.

Cryosectioning of tissue: Frozen, coronal sections (spinal cord: 20 µm, brain: 30 µm) were cut with a Hacker-Bright cryostat (Hacker Instruments and Industries Inc., Winnsboro, S.C.) and mounted on charged glass slides (Superfrost Plus; Fisher Scientific, Pittsburgh, Pa.) so that adjacent CNS sections on each slide represented regions 100 µm and 150 µm apart for spinal cord and brain, respectively (Tabata et al., 2008). The slides were stored at −80° C. until histological processing. To ensure CNS sections were matched between animals, anatomical landmarks were verified using a mouse brain atlas (Paxinos and Franklin, The mouse brain in stereotaxic coordinates: Second Edition, K.B.J., Academic Press, New York, 2001).

EXAMPLE 5

Histology

Figure 5:
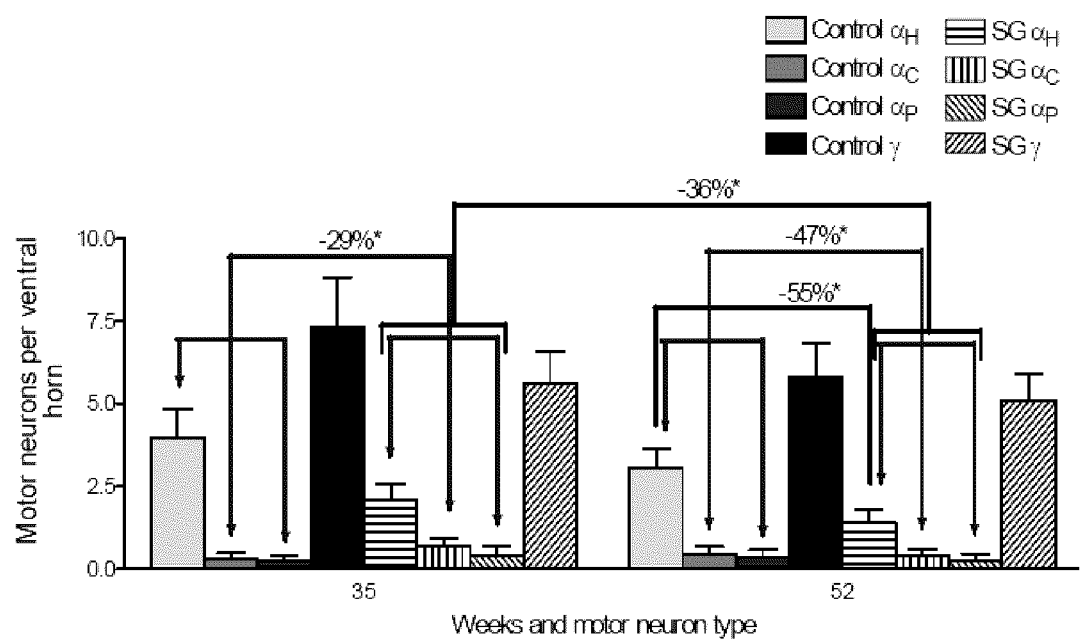
FIG. 5. Motor neuron counts following SG-feeding. Motor neurons were differentiated with cresyl violet for Nissl bodies. Lumbar spinal cord α- and γ-motor neuron counts were conducted at 35 and 52 weeks (A). Motor neurons were sub-grouped into those with a normal, healthy appearance (subscript "H"), those that were chromatolytic (subscript "C") and those that were pyknotic (subscript "p"). At both 35 and 52 weeks, the control group was observed to have numerous healthy α- and γ-motor neurons in the ventral horn of the lumbar spinal cord. With the detailed motor neuron counts, statistical significance was detected between the number of "healthy" α-motor neurons between the control and SG-fed group at 52 weeks (t-test: −55%, p<0.05) only (A). When a statistical analysis was conducted between the total number of α-motor neurons between groups, a significant difference was detected at each of the time points (t-test at 35 weeks: −29%, *p<0.05; t-test at 52 weeks: −47%, *p<0.05; red lines indicate subcategories that were grouped to obtain a α-motor neuron "total"). Further, the SG-fed group was found to undergo a significant decline in the total number of α-motor neurons between 35 and 52 weeks (t-test: −36%, *p<0.05; blue lines indicate the summation of subgroups in the graph).
Figure 8:
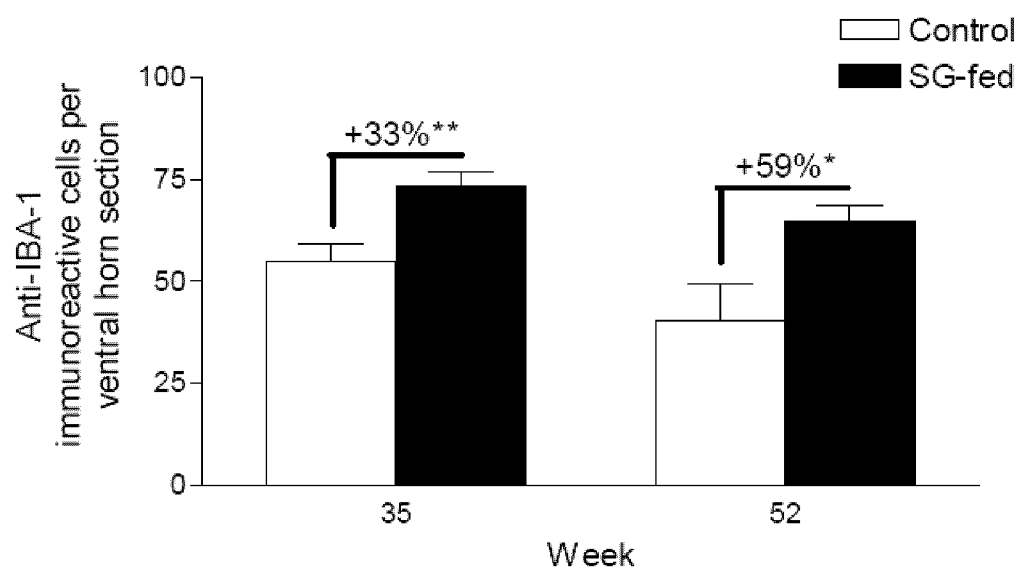
FIG. 8. Microglial proliferation in the lumbar spinal cord of SG-fed mice. Cells immunoreactive to ionized calcium binding receptor-1 (IBA-1) were counted as microglia. (A) Quantification of microglia in the ventral horn of the lumbar spinal cord of control and SG-fed mice at 35 and 52 weeks. SG-fed mice had significantly more microglia compared to the controls at both the pre-symptomatic (t-test: +33%, **p<0.01) and symptomatic (t-test: +59%, *p<0.05) time-points (Student's t-test, *p<0.05).

Histology and quantification of motor neurons: Spinal cord and brain sections from each animal were stained for Nissl body substance. At room temperature (RT), sections were rinsed in a graded ethanol series (95%:15 min; 70%:1 min; 50%:1 min) to rehydrate and remove lipids and fixation chemicals from the tissue. The tissue were then rinsed for 2 min in two exchanges of distilled water, stained with twice-filtered cresyl violet stain (1.25 g cresyl violet acetate, 0.75 mL glacial acetic acid to 250 mL distilled water), rinsed in distilled water (1 minute), and then dehydrated (50% ethanol: 1 minute; 1% glacial acetic acid-70% ethanol: 2 minutes; 95% ethanol: 2 minutes; 95% ethanol: 3 dips; 100% ethanol: 1 minute) and cleared in xylene. The slides were then cover-slipped in Entellen mountant (Merck, Darmstadt, Germany). The tissue mounted slides were selected with a randomized start and sampled starting from the lumbar 2 region to the $6^{th}$. The superior-inferior boundaries of the lumbar and thoracic spinal cord were initially determined by a ventral and dorsal root count and verified by comparison to a stereotaxic mouse atlas (Sidman, et al., Atlas of the mouse brain and spinal cord, Harvard University Press, Cambridge, Mass. (1971)). The boundaries for the ventral horn was determined by the margins of the gray matter for the lateral, medial and ventral boundaries as well as with the aid of an artificial line drawn laterally through the central canal. Both the left and right ventral horns from 12 sections from each animal were counted. Alpha-motor neurons and γ-motor neurons with and without apoptotic structural changes were counted using strict morphological and size criteria. Non-apoptotic α-neurons were considered as the following: Large, multipolar cells with a round, pale nucleus; visible nucleolus; globular Nissl body staining of the cytoplasm; and a diameter of 30-45 µm. In doing so, astrocytes, oligodendrocytes and microglia were excluded from the "α-motor neuron" counts (Martin, L. J. (1999) J Neuropathol Exp Neurol. 58, 459-71; Sepkuty, J. P., et al. (2002) J Neurosci. 22, 6372-9; Tabata et al., 2008). Pyknotic or karyopyknotic α-neurons undergoing apoptosis were considered as those with a diameter of 30 µm and greater with a condensed and darkly stained nucleus, with or without vacuolization outside of the cell. Chromatolytic α-neurons undergoing apoptosis were considered as those with a diameter of 30 µm and greater with no discernable nucleus, with or without shifting of the nucleus from its central position to the periphery, disintegration of the Nissl bodies (chromophil substance), with or without vacuolization outside of the cell. Healthy γ-motor neurons were considered as those cells between 18 µm and 30 µm in size (Szumanska, G., et al. (1977) Neuropatol Pol. 15, 523-35). Apoptotic γ-motor neurons were considered as those between 18 µm and 30 µm in size with a condensed and darkly stained nucleus with or without vacuolization outside of the cell. Those motor neurons with the nucleus (in the count for "healthy" α- and γ-motor neurons), nucleolus, and cytosol intact were included in the counts. Counts performed on non-treated animal sections served as controls. For results see FIGS. 5 and 8.

EXAMPLE 6

Immunofluoresence

Figure 6:
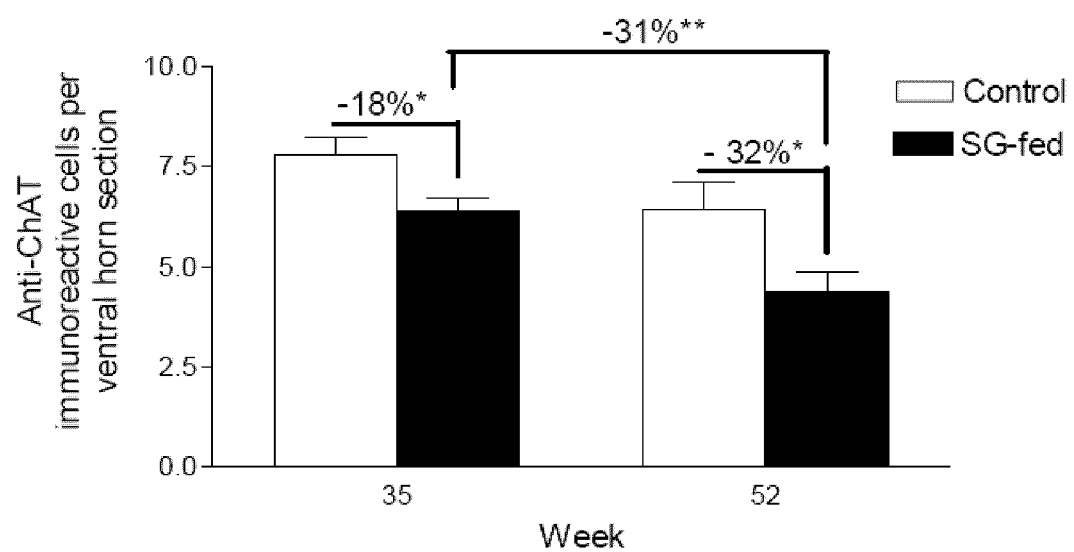
FIG. 6. Cholinergic motor neurons in the spinal cord of SG-fed mice. Anti-choline acetyl transferase (ChAT) immunoreactive cells were counted as cholinergic cells. Quantification anti-ChAT labelling in the ventral horn of the lumbar spinal cord revealed a significant difference between the control and SG-fed groups at 35 and 52 weeks. SG-fed animals had 18% (t-test: *p<0.05) and 32% (t-test: *p<0.05) fewer cholinergic neurons at 35 and 52 weeks, respectively (A). Further, the SG-fed animals experienced a significant decrease in the number of cholinergic neurons between 35 and 52 weeks (t-test: −31%, *p<0.05).
Figure 7:
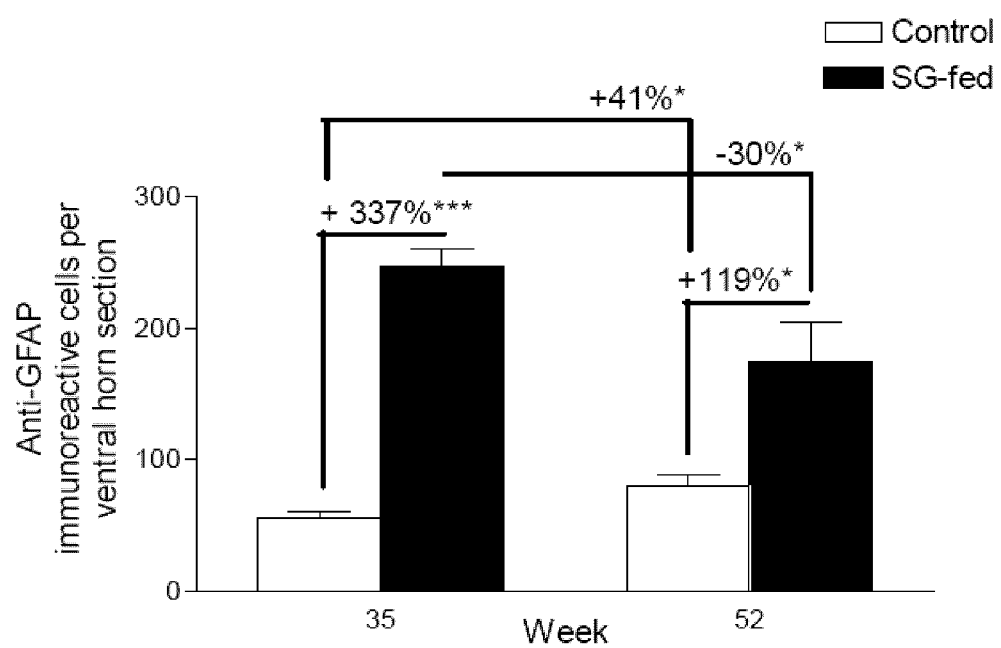
FIG. 7. Activated astrocytes in the lumbar spinal cord of SG-fed mice. Anti-glial fibrillary acidic protein (GFAP) immunoreactive, stellate (both compact and elongated) cells were counted as astrocytes. Quantification of anti-GFAP labelling in the ventral horn of the lumbar spinal cord of control and SG-fed mice at 35 weeks and 52 weeks (A). SG-fed mice had a significantly greater number of astrocytic cells compared to the controls at both the pre-symptomatic (t-test: +337%, ***p<0.001) and symptomatic time-points (t-test: +119%, *p<0.05). Further, while the control animals experienced a significant increase in the number of astrocytes over time (t-test: +41%, *p<0.05), SG-fed animals were found to undergo a significant reduction in GFAP positive astrocytes (t-test: −30%, *p<0.05) over the same 17 week period.
Figure 9:
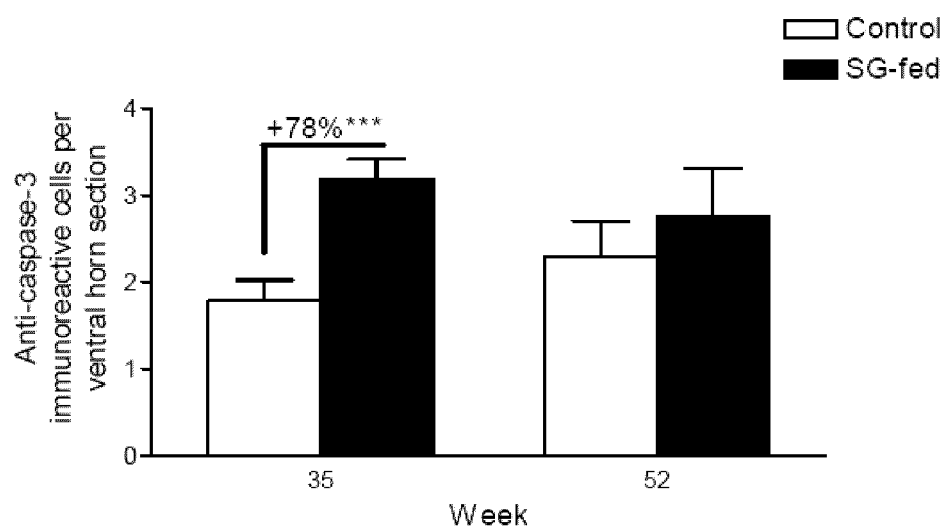
FIG. 9. Caspase-3 labelling in the spinal cord of SG-fed mice. Quantification of anti-caspase-3 immunoreactive cells in the ventral horn of the lumbar spinal cord at 35 and 52 weeks revealed that SG-feeding induced cells to undergo apoptosis at pre-symptomatic and symptomatic time points. At 35 weeks, a significantly greater number of apoptotic neurons were observed in SG-fed animals (t-test, +78%, ***p<0.001) (A). A greater number of apoptotic cells were also observed in SG-fed animals at 52 weeks, but numbers did not reach significance (A).

Tissue-mounted slides were processed for fluorescence microscopy as follows: Sections were rinsed in coplin jars for 45 minutes at room temperature (RT) in three changes of PBS. Sections were then incubated at RT for 30 minutes in a blocking permeabilization solution made of 5% normal goat serum (NGS), 5% normal rabbit serum (NRS) or 5% BlokHen II (Ayes Labs, Inc., Tigard, Oreg.), 0.05% Triton X-100 and PBS. Subsequently, the blocking solution was tipped off and the slides were rinsed in PBS for 2 minutes. Sections were then incubated overnight in a humidified chamber at 4° C. with a PBS buffered solution that contained 1% NGS or 1% NRS, 1% bovine serum albumin (BSA) and one of the following primary antibodies: (a) rabbit anti-human/mouse ATF-3 (H-90) IgG (polyclonal, 1:500; Santa Cruz Biotechnology, Inc., Santa Cruz, Calif.), (b) anti-activated caspase-3 IgG (monoclonal, 1:250; Chemicon International, Temecula, Calif.) (see FIG. 9), (c) goat anti-human/mouse choline acetyl transferase (ChAT) IgG (polyclonal, 1:100; Chemicon International, Temecula, Calif.) (see FIG. 6), (d) rabbit anti-mouse glial fibrillary acidic protein IgG (polyclonal, 1:250; GeneTex Inc., San Antonio, Tex.) (see FIG. 7), (e) rabbit antihuman/mouse ionized calcium binding adaptor molecule 1 (IBA-1) IgG (polyclonal, 1:500; Wako Pure Chemical Industries, Ltd, Richmond, Va.), (f) mouse anti-human/mouse clone AT8 PHF-1

Figure 10:
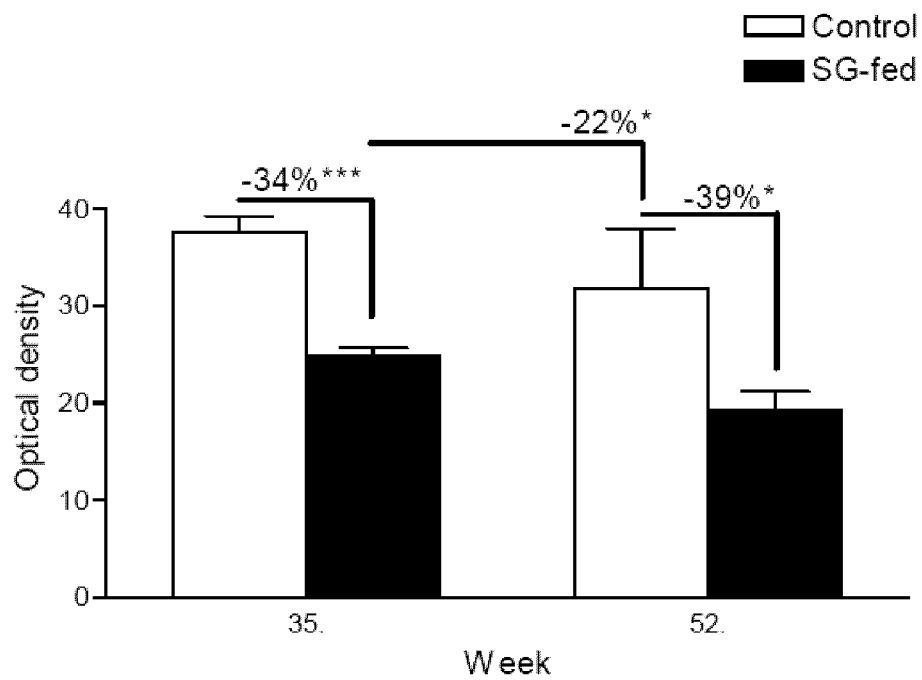
FIG. 10. Dopaminergic cell labelling is lost in the striatum of SG-fed mice. SG-fed mice showed significantly decreased tyrosine hydroxylase labelling (optical density) compared to controls in the substantia nigra pars compacta (SNpc) at 35 weeks (t-test: −34%, ***p<0.001) and at 52 weeks (t-test: −39%, *p<0.05). TH optical density was found to decrease among SG-fed animals over time (ttest: −22%, *p<0.05) in the SNpc (A). A decrease in optical density was not found among the striata of the SG-fed animals' at either time-point (t test: not significant p=0.0846) (F). The toxicity to motor and niagral striata caused in SG-fed mice indicates that SG can be used in models of motor neuron disease and in Parkinson's disease models, among other neurodegenerative disease states.
Figure 14:
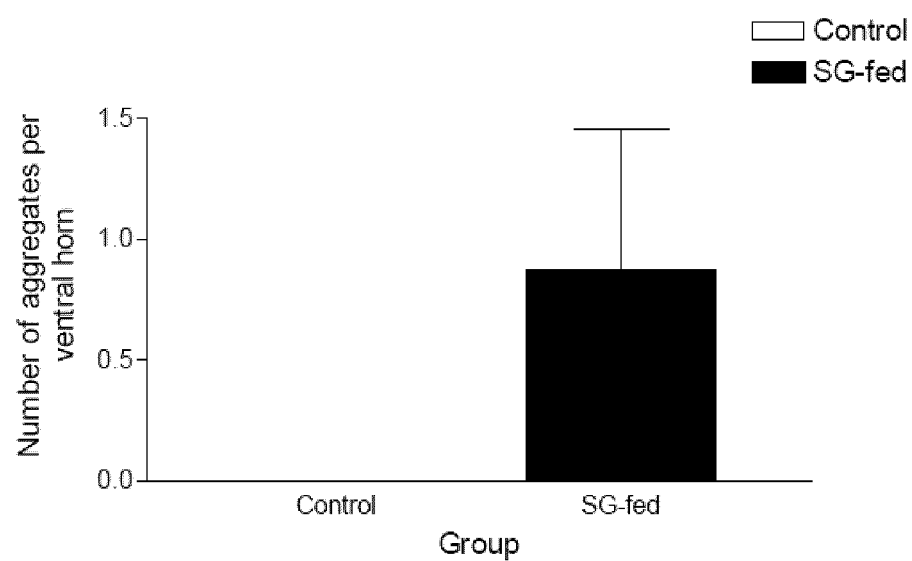
FIG. 14. TDP-43 pathology occurs in the lumbar spinal cord of a subset of mice fed SG. Two of eight mice fed SG, that survived to 52 weeks exhibited TAR DNA binding protein (TDP) 43 pathology. In healthy cells, TDP-43 is found in the nucleus, but redistributes and accumulates in the cytosol in neurological conditions, such as in sporadic ALS. No abnormal translocation of TDP-43 was observed in control animals, SG-fed animals at 35 weeks, and in the majority of SG-fed animals at 52 weeks. The frontal cortex, hippocampus, and motor cortex were also negative in control animals at both time-points. Panel A depicts quantification of pathologic phosphorylated TDP-43-containing aggregates in the lumbar spinal cord. These aggregates increased in the SG-fed animals.

Tau (monoclonal, 1:200; Pierce Biotechnology Inc., Rockford, Ill.), (g) rabbit anti-human/mouse TAR DNA-binding protein 43 (TDP43) (1:100; ProteinTech Group Inc., Chicago, Ill.) (See FIG. 14), (h) chicken anti-human/mouse β-tubulin 3 (TuJ1 antigen) (polyclonal, 1:100, Ayes Labs, Inc., Tigard, Oreg.), (i) rabbit anti-mouse tyrosine hydroxylase (polyclonal, 1:500, Chemicon International, Temecula, Calif. or polyclonal 1:1000, Affinity BioReagents, Golden, Colo.) (FIG. 10), (j) rabbit anti human/mouse anti-pJun$_{scr73}$ IgG (polyclonal, 1:200; Chemicon International, Temecula, Calif.), (k) rabbit anti human/mouse anti-HSP-70 IgG (polyclonal, 1:200; Chemicon International, Temecula, Calif.), or (l) rabbit anti human/mouse anti-HSP-25 IgG (polyclonal, 1:100; Chemicon International, Temecula, Calif.). In each experiment, additional slides were incubated with the primary antibody and the secondary antibody omitted or with secondary antibody and primary antibody omitted to test for nonspecific staining. Where appropriate, positive control slides (Alzheimer's disease patient entorhinal cortex, obtained from Drs. Claudia Schwab and Patrick McGeer of the Kinsmen Laboratory, University of British Columbia, Vancouver, BC, Canada) were also processed as above for comparison. Following overnight incubation with the primary antibody, slides were rinsed for 45 minutes at RT in three changes of PBS. Immediately after, the slides were incubated in black chambers that excluded light for 1 hour at RT with the secondary antibody solutions containing 5% NGS or 5% NRS and fluorophore conjugated antibodies: AlexaFluor 568 goat anti-rabbit or rabbit anti-goat IgG (monoclonal, 1:250, absorption: 578 nm, emission 603 nm; Molecular Probes, Eugene, Oreg.), AlexaFluor 546 goat antirabbit or rabbit anti-goat IgG (monoclonal; 1:250, absorption 556 nm, emission 573 nm; Molecular Probes, Eugene, Oreg.) or fluorescein isothiocyanate (FITC) goat anti-rabbit IgG (polyclonal, 1:500, absorption: 494 nm, emission: 518 nm; Sigma, Saint Louis, Mo.). The secondary antibody solution was tipped off and slides were rinsed for 15 minutes in three changes of PBS. Tissue sections were cover-slipped with a 4'6 diamidino-2-phenylindole (DAPI) fluorescent mounting media (Vectashield, absorption: 360 nm, emission: 460 nm, Vector Laboratories, Burlington, ON, Canada) in order to label the nuclei and stored at 4° C. in dark slide boxes to retard bleaching of the fluorescent labels.

EXAMPLE 7

Tau Immunohistochemistry

Figure 13:
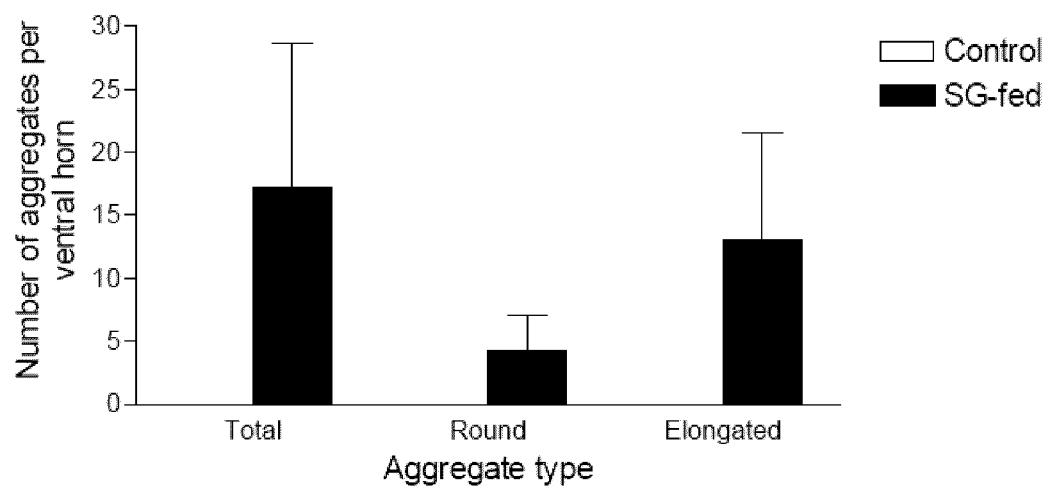
FIG. 13. Select SG-fed mice accumulated phosphorylated tau in the ventral horn of the lumbar spinal cord and a subset of these phosphorylated tau-containing cells underwent apoptosis. Dietary SG-feeding induced accumulation of phosphorylated tau. The majority of the phosphorylated-tau containing cells were actively undergoing apoptosis in animals at 52 weeks. (A) The numbers of elongated and round aggregates were quantified separately (A).

Slide-mounted lumbar and thoracic spinal cord and brain sections were first rinsed for 45 minutes in 3 changes of PBS then quenched in 3% $H_2O_2$ in PBST (PBS+0.5% Triton X-100) for 10 minutes. The slides were rinsed for 4 minutes in 2 changes of PBST. The MOM mouse Ig blocking reagent was prepared as per the manufacturer's instructions. Two drops of mouse Ig stock solution was added to 2.5 mL of PBS. The sections were incubated with this solution for 1 hour at RT. Following this step, sections were rinsed for 4 minutes in 2 changes of PBST and incubated (5 minutes) with the MOM diluent solution prepared by adding 600 V1 of MOM protein concentrate to 7.5 mL of PBS. The diluent was tipped off the slides and replaced by a solution comprised of primary phospho-Tau antibody diluted at 1:100 in the diluent solution prepared in the same manner as discussed above. The sections were incubated for 60 minutes at RT. Subsequently, sections were rinsed for 4 minutes in 2 changes of PBST and incubated for 10 minutes in the MOM biotinylated anti-mouse IgG reagent (10 V1 of MOM biotinylated anti-mouse IgG diluted in 2.5 mL of the MOM diluents). The sections were then rinsed in PBST and incubated (1 hour at RT) with the secondary antibody prepared by combining one drop of secondary antibody (biotinylated goat-anti-rabbit IgG) from the Vectastain ABC Elite kit (Vector Laboratories, Burlingame, Calif., USA) was combined with 3 drops of serum stock to 10 mL of PBST. At 30 minutes after start of slide incubation with the secondary antibody, an immunoperoxidase solution was prepared by adding 2 drops of reagent A and 2 drops of reagent B (Vectastain Elite ABC kit, Vector Laboratories, Burlingame, Calif., USA) to 2.5 mL of PBST. After one hour incubation of the slides with the secondary antibody solution, the slides were rinsed for 4 minutes in two changes of PBST and incubated for 30 minutes in the working immunoperoxidase solution. Next, the sections were rinsed for 4 minutes in 2 changes of PBST. During the rinses, the DAB liquid substrate was prepared for the next step. As per manufacturer's instructions, 2 drops of buffer stock solution, 5 mL of $ddH_2O$, 4 drops of DAB stock solution, and 2 drops of hydrogen peroxide solution were combined. The slides were incubated for 3 minutes at RT with this DAB solution and monitored for color development. The sections were rinsed for 5 minutes in $ddH_2O$ to stop the reaction and rid slides of DAB substrate. A methyl green nuclear counterstain was used to elucidate nuclei and motor neuron somata. The 0.5% methyl green counterstain was prepared in the following manner: First, the sodium acetate buffer was prepared with 1.36 g of sodium acetate trihydrate to 100 mL of distilled water adjusted to pH 4.2 using glacial acetic acid. For every 100 mL of buffer, 0.5 g of methyl green (ethyl violet, Sigma-Aldrich, Oakville, ON, Canada) was added to make a 0.5% methyl green solution. Slide-mounted sections were stained in the above methyl green solution for 5 minutes at RT. Sections were rinsed in distilled water, until the water became clear. Next, sections were dehydrated quickly with 95% ethanol (5 dips) and 2 changes of 100% ethanol (5 dips in each change), then cleared by 10 dips of xylene. Finally, the slides were dried under a fume hood and cover-slipped with a resinous mounting media (Entellen, Merck, Darmstadt, Germany). No phosphorylated Tau aggregates were observed in the non-treated mice. Phosphorylated Tau aggregates were observed in the SG-fed mice (see FIG. 13).

EXAMPLE 8

Tyrosine Hydroxylase Immunohistochemistry

Labelling of dopaminergic neurons in brain sections was identified by antibodies for tyrosine hydroxylase (Morrow, C. E., Bandstra, et al., (2001) Neurotoxicol Teratol. 23, 533-44) and indirect immunoperoxidase staining. Sections were incubated in blocking serum for 2 hours then with the primary antibody (rabbit anti-tyrosine hydroxylase, 1:500, Affinity Bioreagents, Golden, Colo., USA) for 3 hours at RT. Sections were rinsed and incubated in biotinylated goat anti-rabbit IgG (1:100; Vector laboratories Inc., Burlingame, USA) for 30 minutes at RT, then visualized using the ABC method (Vectastain Elite ABC kit, Vector Laboratories Inc.). See FIG. 10.

EXAMPLE 9

Cytochrome C Oxidase Histochemistry

Figure 11:
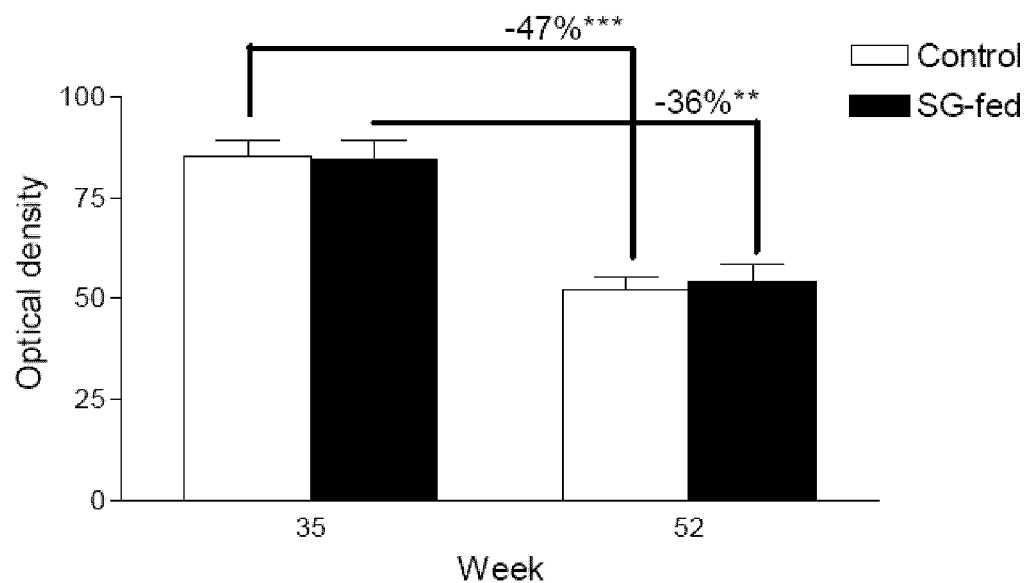
FIG. 11. Cytochrome c oxidase activity is unaffected in SG-fed animals. Cytochrome c oxidase activity was analyzed in SG-fed animals and age-matched controls. No significant differences were observed between groups at 35 or 52 weeks (A). A decline in cytochrome c oxidase activity was observed to occur over time in each of the groups (A).

Tissue-mounted slides were processed for fluorescence immunohistochemistry in a manner adapted from (Seligman et al., J. Cell. Biol. 1968; 38: 1-14) and Wong-Riley, (1979), Brain Res. 171, 11-28. Sections were rinsed in coplin jars for 15 minutes at RT in three changes of PBS and subsequently incubated with a media comprised of 50 mg of 3,3'-diaminobenzidine tetrahydrochloride (DAB) (DAB substrate system, Vector Laboratories, Burlingame, Calif., USA), 90 mL 0.1M phosphate buffer, 20 mg cytochrome c (type III, Sigma-Aldrich Co., Oakville, ON, Canada), and 4 g of sucrose in a dish submerged in a water bath maintained at 37° C. in the dark for 2 hours. The sections were monitored closely for the brown reaction product to appear within the tissue. Once a medium-brown color was achieved, slides were removed from the incubation media and rinsed for 15 minutes in three changes of PBS to stop the reaction. This was followed with a 2 minutes rinse in distilled water to remove residue from the slides. The slides were dried under a fume hood and cover-slipped with Entellen (Merck, Darmstadt, Germany). The results show no significant differences between the control mice and the SG-fed mice, although both groups showed a decline in cytochrome c oxidase over time, see FIG. 11.

EXAMPLE 10

Oil Red O Histochemistry

Figure 12:
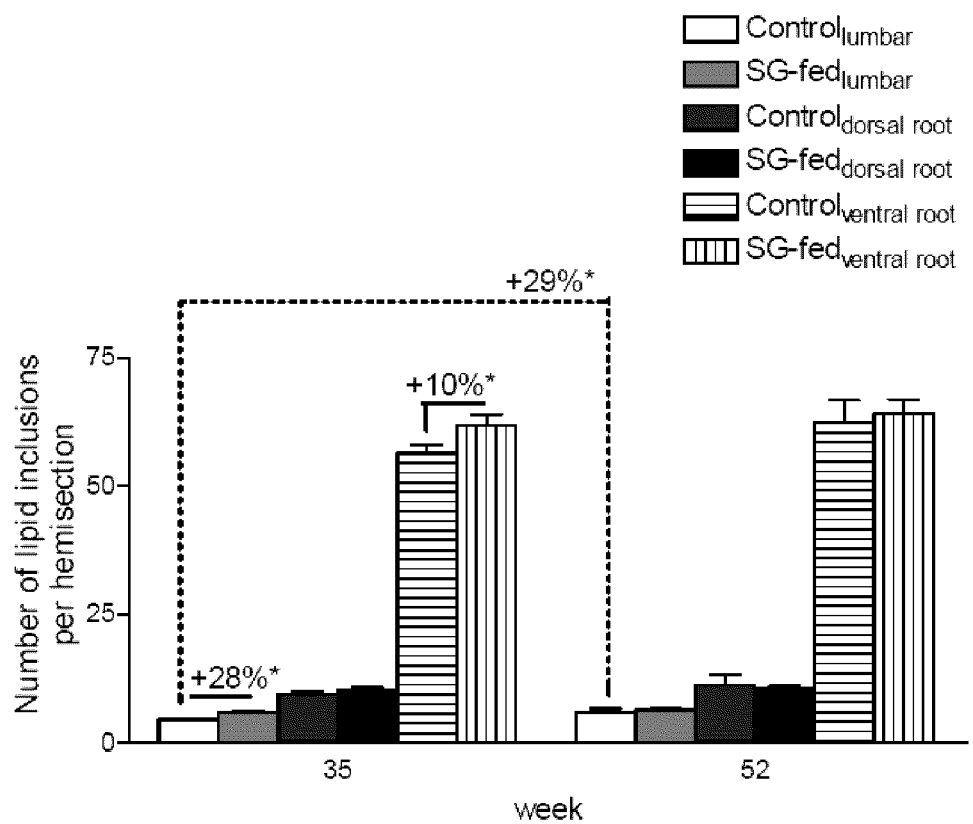
FIG. 12. Oil red O staining of lipids in the lumbar spinal cord and dorsal and ventral spinal roots. Lipid deposits in various CNS regions were revealed by oil red O (red colored stain). Nuclei were stained with haematoxylin (blue/purple coloured stain). Lipid deposits were observed in the motor neurons of control and SG-fed mice, but the number and size of the deposits were greater in lumbar spinal cord and ventral roots of SG-fed animals. Panel A shows a quantification of lipid deposits in control and SG-fed animals at 35 and 52 weeks. An inter-group assessment of the ventral horn of the lumbar cord revealed that at 35 weeks, SG-fed animals had significantly more lipid deposits in the ventral horn of the lumbar spinal cord (Student's t-test, +28%, *p<0.05). SG-fed animals also had significantly more lipids in the ventral spinal roots compared to control animals at 35 weeks (Student's t-test: +10%, *p<0.05). A similar comparison of the dorsal roots did not show a statistically significant difference (Student's t-test: not significant, p=0.3778). At 52 weeks, statistically significant inter-group differences were not found in the three CNS regions that were assessed (lumbar spinal cord: Student's t-test, p=0.6406; dorsal root: Student's t-test, p=0.6958; ventral root: Student's t-test, p=0.7422). Time-dependent effect assessment of lipid accumulation in SG-fed animals and age-matched controls was also performed. Control animals showed a statistically significant increase in the total number of lipid deposits over time (Student's t-test: +29%, p<0.05). SG-fed animals did not experience an accumulation of deposits over time (Student's t-test, p=0.4864). Both SG-fed animals and controls did not show time-dependent effects in the dorsal (Student's t-tests-control: p=0.4864; SG-fed: p=0.5478) or ventral roots (Control: p=0.1301; SG-fed: p=0.5478).

Tissue-mounted slides were processed to evaluate lipid distribution with light microscopy with a protocol adapted from Dr. Roy Ellis (IMVS Division of Pathology, The Queen Elizabeth Hospital, Woodville, South Australia). First, an oil red O stock solution was prepared 2 hours prior to execution of the histochemical procedures. The oil red O stock stain solution was made by mixing oil red O (0.5 g, Sigma-Aldrich, Oakville, ON, Canada) and isopropanol (100 mL, Fisher Scientific, Nepean, ON, Canada) over a 40° C. water bath. Immediately prior to beginning the oil red O histochemical procedures, the oil red O working solution was made by combining 20 mL of distilled water for every 30 mL of oil red O stock stain solution. This working solution was filtered five times to remove any oil red O that did not dissolve in the solvent. Slide-mounted sections were rinsed in coplin jars for 15 minutes at RT in three changes of PBS. Sections were then rinsed at RT with 60% isopropanol for 5 minutes. The spinal cord sections were then stained with a freshly prepared working solution of oil red O for 20 minutes and then rinsed with 60% isopropanol. Nuclear counterstaining was achieved by staining the sections with haematoxylin (haematoxylin, 7211, Richard Allan Scientific, Kalamazoo, Mich., USA) for 1 minute. Finally, the sections were rinsed with distilled water, dried under a fume hood and cover-slipped with Entellen (Merck, Darmstadt, Germany). See FIG. 12.

EXAMPLE 11

Tissue Visualization and Image Capture

Immunofluorescence protocol processed tissue sections were examined and captured using a Zeiss Axiovert 200M (Carl Zeiss Canada Limited, Toronto, ON). DAPI (blue fluorescence) visualization required a 359/461 nm absorption/emission filter. FITC required a 490,494/520 nm filter. Alexa Fluor 546™ (red fluorescence) utilized a 556,557/572,573 nm filter. During quantification at 40× magnification, two images were captured per lumbar and thoracic spinal cord section (i.e. left ventral horn and right ventral horn). Similarly, two images were captured per brain region and per dorsal or ventral root section. 40× images were 350×275 Vm in dimension. Images were captured using AxioVision 4.3 software. Data processed through immunofluorescence was analyzed using Zeiss Axiovert Zoom Axiovision 3.1 with AxioCam HRM. Non-fluorescent protocol processed tissue sections were examined and captured using the Motic B5 Professional Series 3.0 microscope (Motic Instruments Inc., Richmond, ON) and data were analyzed using Motic B5 Professional, Motic Images Advanced 3.0 (Motic Instruments Inc., Richmond, ON).

EXAMPLE 12

Quantification of Immunoreactive Cell Somata or Inclusions

The numbers of immunoreactive somata or inclusions were counted across the ventral horn of the spinal cord, across brain hemispheres, or per dorsal or ventral root with the 40× objective lens in a 600 μm/600 μm area within region perimeters defined by a mouse brain atlas (2001). For each animal, eight cross-sections per spinal cord or brain region were studied. An average of both the right and left ventral horn for each of the eight cross sections was generated giving a final averaged number for each animal in each of the spinal cord areas. For quantification of the level of mitochondrial activity (cytochrome c oxidase labelling) in the lumbar spinal cord or tyrosine hydroxylase immunoreactivity in the substantia nigra pars compacta and striatal sections, images captured using the Motic B5 Professional Series 3.0 microscope (Motic Instruments Inc., Richmond, ON) and analyzed using Motic B5 Professional, Motic Images Advanced 3.0 (Motic Instruments Inc., Richmond, ON) were scanned into a TIFF format file and analysed using the NIH Image J 1.37 software to measure density levels of antibody labelling. Eight to 12 sections from each mouse per region of interest were included.

EXAMPLE 13

Statistical Analyses

Quantitative data obtained from each hemisphere of each spinal cord or brain section was averaged to generate a hemispherical average, then data averages for each animal was averaged prior to statistical analyses. Differences between the control and SG-fed mice were statistically evaluated using the Student's t-test with a $p<0.05$ being required for significance. All data are expressed as mean+/− standard error of the mean (SEM). Statistical significance was established using either an unpaired two-tailed t-test, one-way or two-way ANOVA followed by a Tukey's posthoc or Fisher's LSD (GraphPad Prism v3.0, GraphPad Software Inc., San Diego, Calif.; Statistica for Windows v. 6.1 statistical software package, Statsoft, Tulsa, Okla.). Statistical analyses were reviewed independently by several reviewers from the Department of Statistics, University of British Columbia.

EXAMPLE 14

Neurotoxicity Modulator Chemistry

One lot of cycad flour (PL-flour) caused a Parkinson-like syndrome in rats that were fed the flour. When one fraction (fraction PL) of the extract of the flour is compared by HPLC to the same fraction from extracts of three other lots of flour which did not cause the same Parkinson-like syndrome, it was observed that one fraction is present in a greater amount in the extract from the PL-flour than in the other extracts. HPLC conditions, column SB-C18, 80% MeCN, 20% MeOH, 0.2 mL/min, 30° C.; unresolved, one peak of interest at 7.37 min. Observed at 210 nm, 300 nm, and by fluorescence (observed at 330 nm, excitation at 295 nm). At higher temperature the peak is further resolved into three peaks, 3.50 min, 3.73 min, 4.05 min detector set at 210 nm; The 4.05 min peak only appears when the detector is set at 300 nm. HPLC conditions SB-C18, 80% MeCN, 20% MeOH, 0.2 mL/min, 60° C.

The proton NMR of fraction PL indicated that the majority of all protons in this molecule are derived from fatty acids which included mono, di and/or poly-unsaturated fatty acids. Peaks at 0.9, methyl; 1.3, methylene; 1.6, beta-CO methylene; 2.1, allylic methylene; 2.3, alpha-CO; a 2.8, double allylic peak; 5.2, glyceride; and 5.3, double bonds. These signals all had 2D NMR correlations consistent with the proposed structure fragments and make up 85% of all protons in this fraction. Also, a glyceride methylene (probably C1) at 4.1 and 4.3 ppm each peak a doublet of doubles can be identified. All other glyceride and sugar peaks that fall in the region of 3.5-4.5 ppm are broadened. Heating to 80° Celsius in pyridine-D5 helps somewhat with broadness of the sugar region including the resolution of an anomeric carbon at 105 ppm but full resolution of the gylceride and sugar region was not observed. In NMR terms, the TOCSY correlations were incomplete and one it was not possible to determine an intact sugar spin system. Also, broadening resulted in loss of signal to noise. Consequently, not all of the carbons were detectable via HSQC.

MS data show the presence of related glycolipids comprising primarily mono- and di-C6-saccharides attached to diacylglycerol in two of the three HPLC peaks. The third peak contains a compound that is identified by NMR, LCMS (M+H$^+$417) and the UV and fluorescence data as β-tocopherol. The higher abundance of this material in the flour yielding the Parkinson-like syndrome suggests that it is modulating the neurotoxicity effects of the other components in the cycad flour.

For one component of the mixture, the MS signal at M+H=417 with a fragment at 151 matches the structure of beta and gamma tocopherol which are regioisomers. The UV and fluorescence emission spectra are also consistent with a tocopherol structure. The proton and carbon NMR data clearly establish this as beta-tocopherol with peaks observed in our results (see structure below). Particularly, C7 ($^1$H at 6.46, $^{13}$C at 115.3) and C8 (methyl) ($^{13}$C at 15.8) for beta-tocopherol was observed while those peaks expected for the gamma regioisomer C5 (1H at 6.37, $^{13}$C at 112.1) and C8 (Methyl) ($^{13}$C at 11.9) were not. The terpenoid tail of this molecule was not clearly resolved in the NMR data from fraction PL as it overlaps with the signals of the fatty acid chains of the glycolipid. The methyl groups on carbons C4', C8' and C12' at 0.87 ppm did clearly show carbon signals at 19 ppm and 22 ppm consistent with the tocopherol structure (the terminal methyl group of the fatty acids overlap in this region but have carbon signals of 13 ppm. The protons on C3 and C4 of tocopherol are also observed and show coupling to each other in the COSY and TOCSY data (not shown).

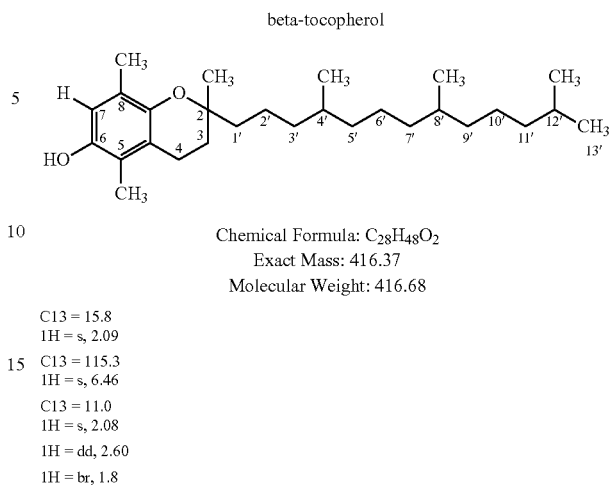

beta-tocopherol

Chemical Formula: $C_{28}H_{48}O_2$
Exact Mass: 416.37
Molecular Weight: 416.68

C13 = 15.8
1H = s, 2.09
C13 = 115.3
1H = s, 6.46
C13 = 11.0
1H = s, 2.08
1H = dd, 2.60
1H = br, 1.8

Analysis of the fraction by high resolution mass spectrometry indicates that the fraction of material that is not β-tocopherol comprises a mixture of disaccharide and monosaccharide glycolipids. The mass spectrometry data is summarized below.

Mass Spectral Data
Disaccharide Components

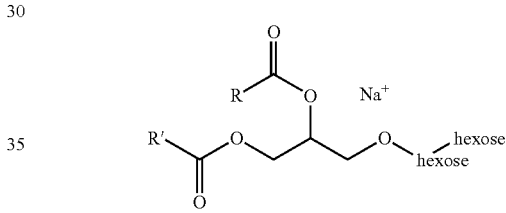

Two major mass peaks were analyzed:
939 peak
HRMS 939.5879, calculated for $C_{49}H_{88}NaO_{15}$ [18:2, 16:0, hexose, hexose, Na$^+$] 939.6021. MSMS shows peaks at 685.44, 683.41, 659.38, 657.39, and 405.17 indicating fragments derived from loss of either fatty acid (FA) or both and that the degree of unsaturation in the FAs is mixed.
965 Peak
HRMS 965.6033, calculated for $C_{51}H_{90}NaO_{15}$ [18:2, 18:1, hexose, hexose, Na$^+$] 965.6177. MSMS shows peaks at 683.41, 685.42, and 405.17 indicating fragments derived from loss of either fatty acid (FA) or both.

Monosaccharide Components

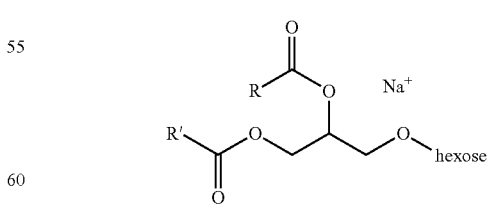

One major mass peak was analyzed:
801 Peak
HRMS 801.5357, calculated for $C_{45}H_{78}NaO_{10}$ [(18:1, 18:3) and (18:2, 18:2), hexose, Na$^+$] 801.5493. MSMS shows peaks at 519.34, 521.34, 523.38, and 243.08 indicating fragments derived from loss of one 18:1, 18:2, and 18:1 FA or both. Peaks at 335.28, 337.31, and 339.3 indicate fragments derived by further loss of a hexose fragment from the fragments derived from loss of one FA.

EXAMPLE 15

Prenatal Exposure to Steryl Glucoside

Figure 27:
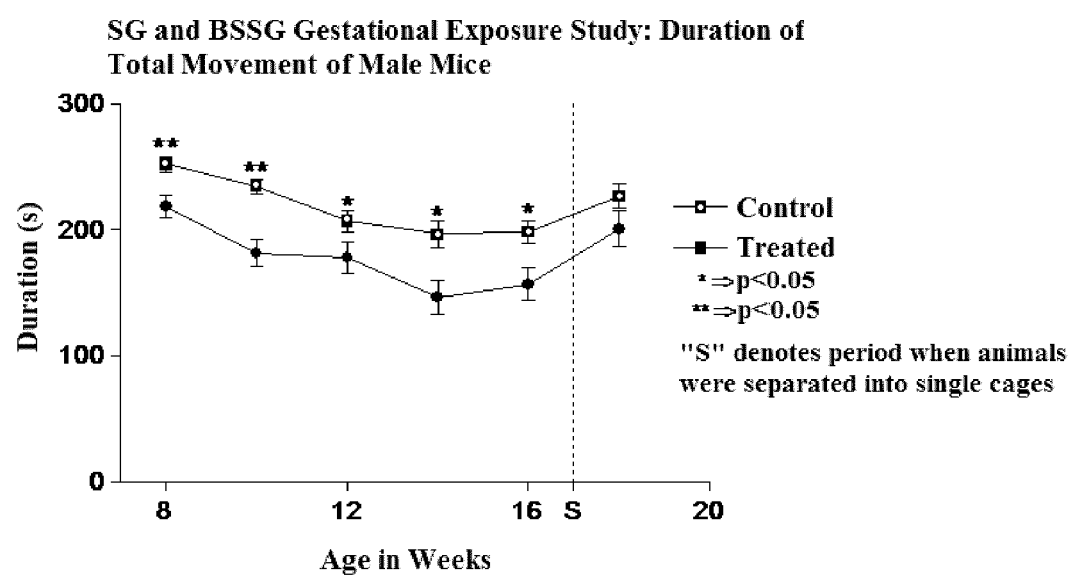
FIGS. 27-41. Animals exposed to SG and BSSG during gestation demonstrated reduced performance in open field tests compared to age matched controls. Pregnant mice were fed food pellets each containing substantially 0.4 mg of SG and 0.6 mg of BSSG. Their pups were tested for exploratory activity at various ages during the period beginning at 8 weeks through to 18 weeks following birth. Tests were conducted over 5 minute intervals: animals were placed at the centre of a test arena and several exploratory activity parameters were measured. Treated animals as compared to control animals demonstrated a significant decrease in duration of total movement [(Student's t-test: *p<0.05, **p<0.05 (FIG. 27); and (Student's t-test: *p<0.05) (FIG. 28)]; frequency of grid crossings into the centre of the arena [(Student's t-test: *p<005, p<0.005, *p<0.0005) (FIG. 29); and (Student's t-test: *p<005, p<0.005) (FIG. 30)]; mean distance to the arena border (indicating that treated mice showed a preference for the periphery of the arena rather than the center) [(Student's t-test: *p<0.0005) (FIG. 31); and (Student's t-test: *p<0.05) (FIG. 32)]; and duration of time spent in centre of arena [(Student's t-test: **p<0.005) (FIG. 33) and (Student's t-test: *p<0.05) (FIG. 34)]. Treated animals compared to control animals also demonstrated a significant increase in mean turn angle [(Student's t-test: *p<0.05, p<0.005, ***p<0.0005) (FIG. 35); and (Student's t-test: *p<0.05, *p<0.005) (FIG. 36)]; and duration of time to cross into arena centre for the first time [(Student's t-test: *p<0.05) (FIG. 37) and (Student's t-test: *p<0.05) (FIG. 38)]. Further, male treated animals as compared to male control animals demonstrated a significant decrease in velocity (Student's t-test: *p<0.05) (FIG. 39); and a significant increase in angular velocity (Student's t-test: *p<0.05, **p<0.005) (FIG. 40); and degree of meander (Student's t-test: *p<0.05, **p<0.005) (FIG. 41).
Figure 28:
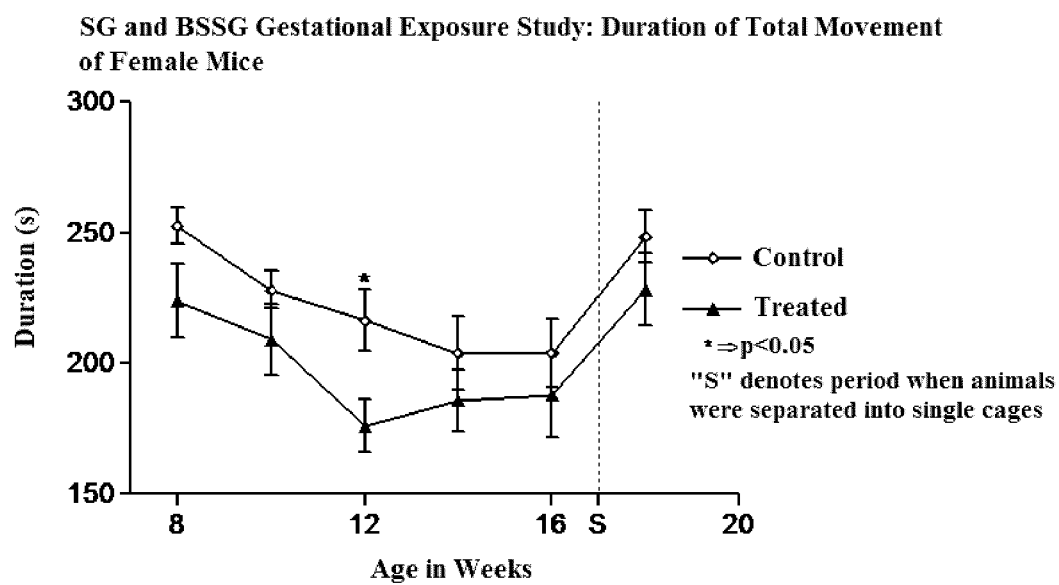
Figure 29:
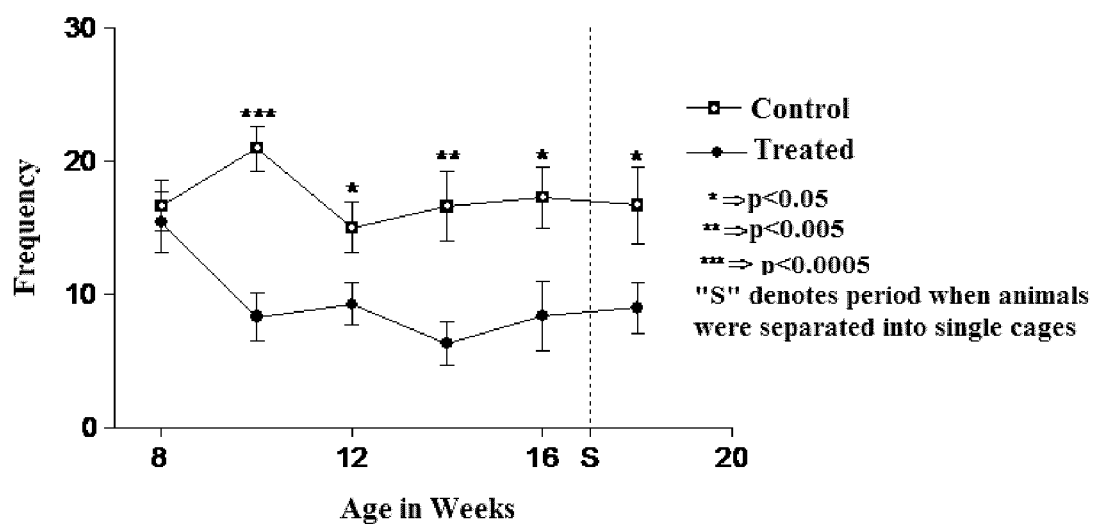
Figure 30:
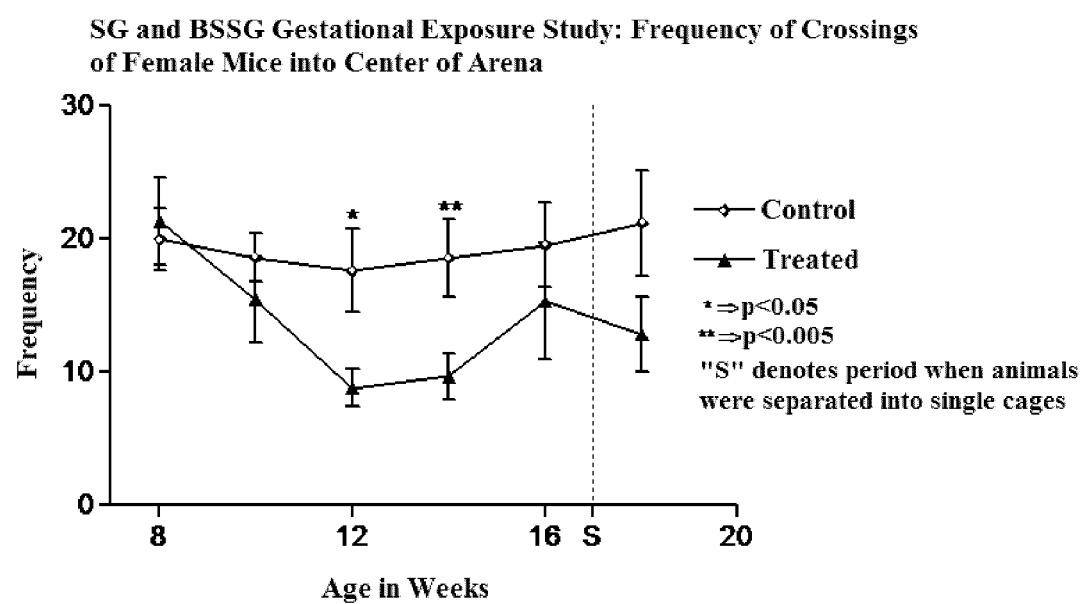
Figure 31:
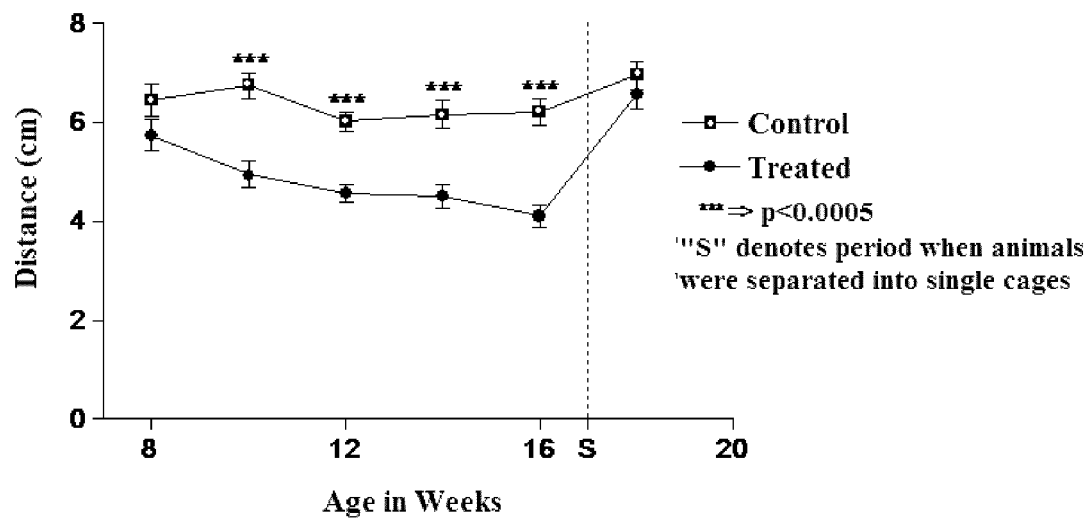
Figure 32:
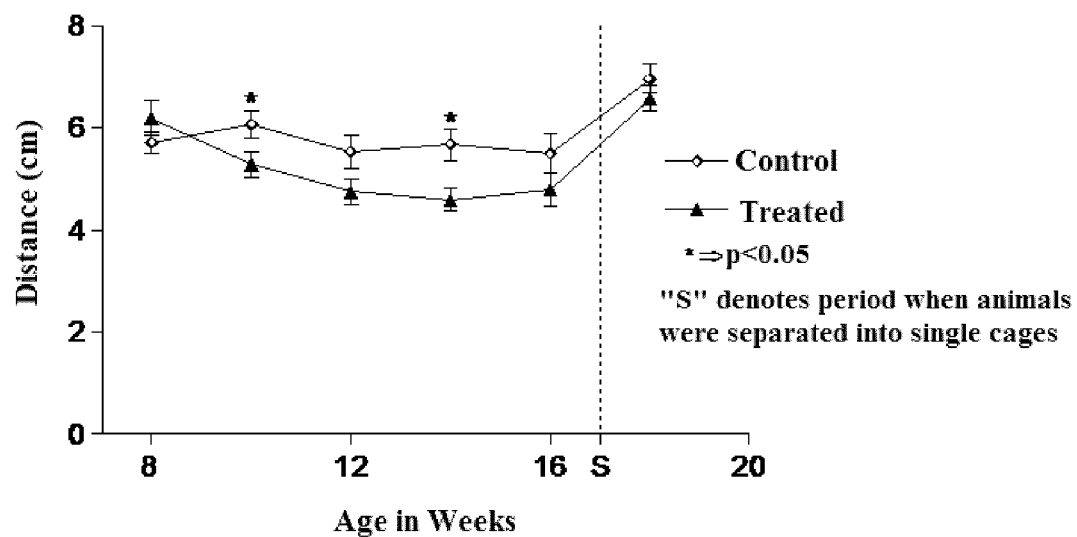
Figure 33:
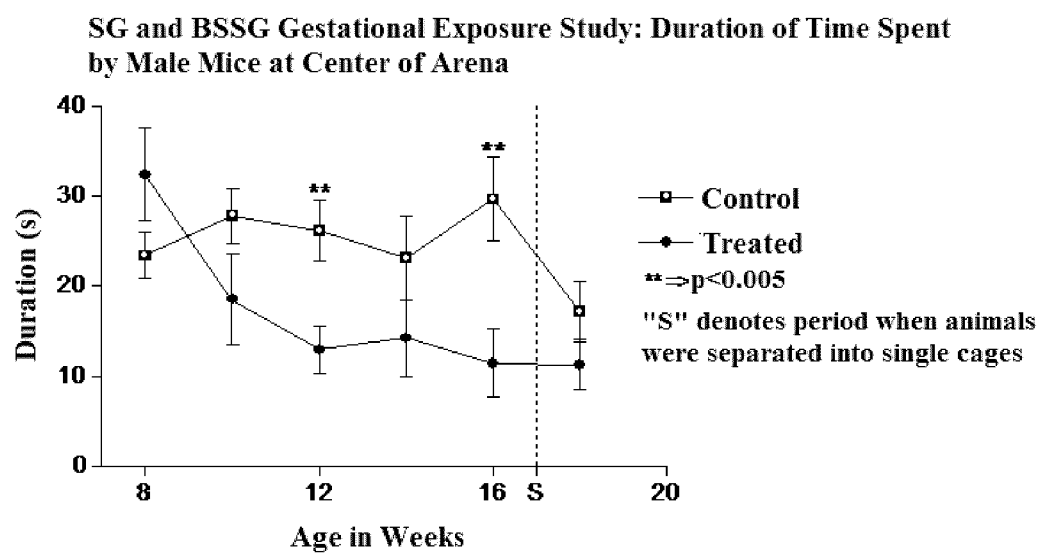
Figure 34:
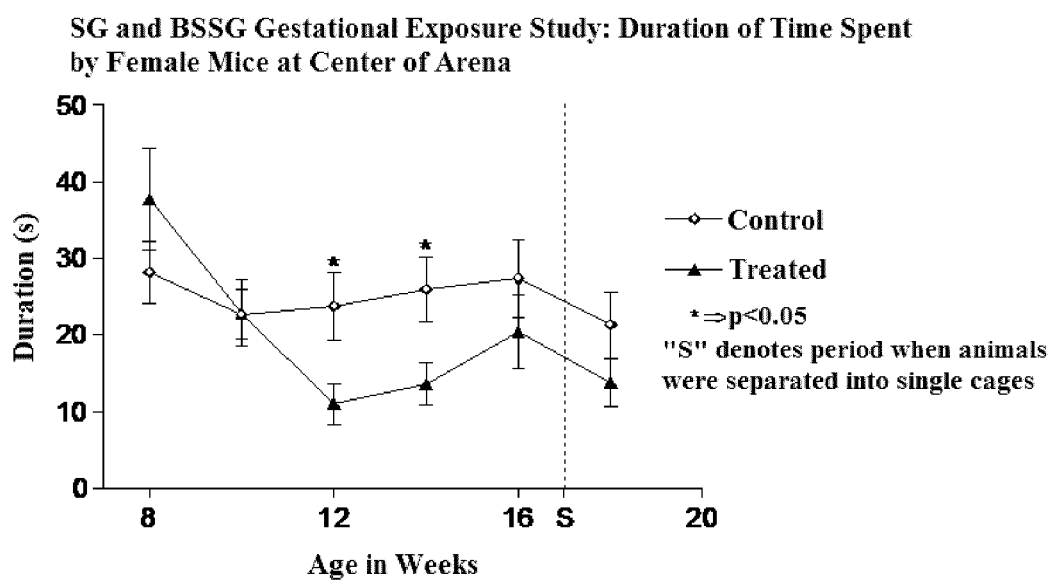
Figure 35:
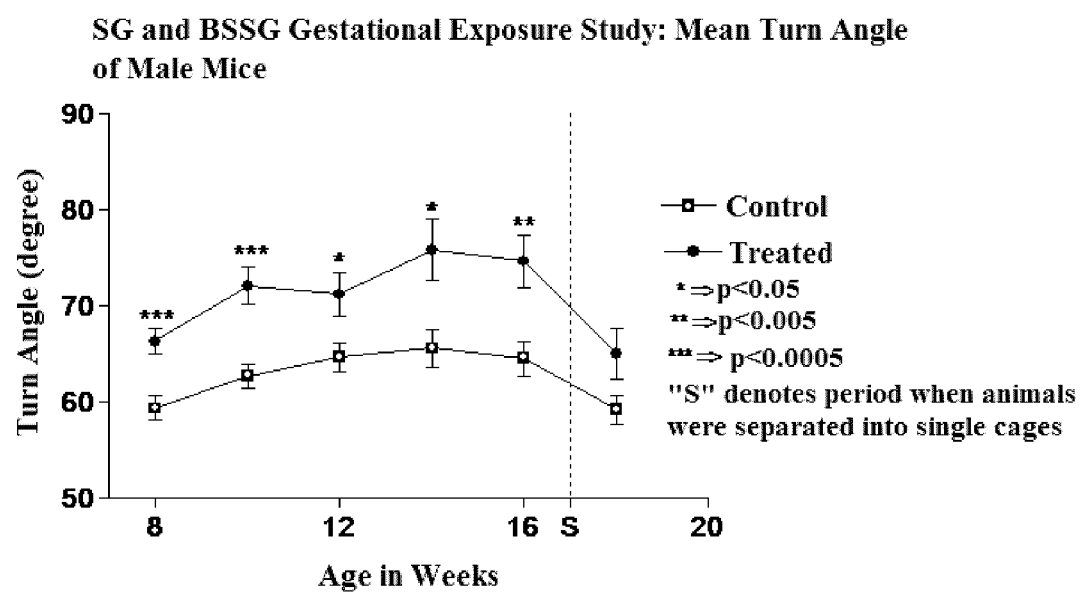
Figure 36:
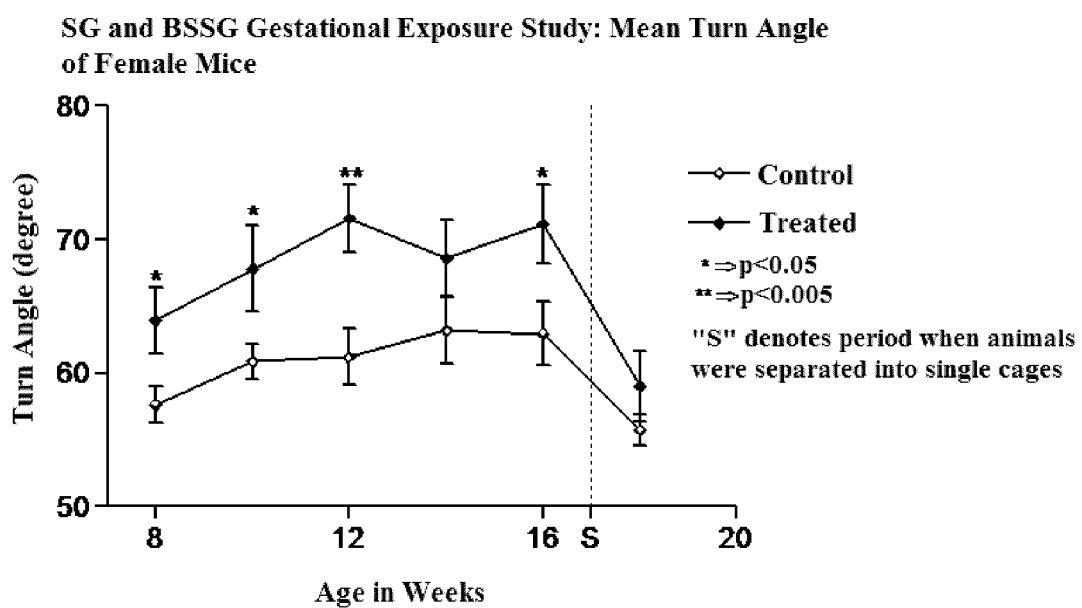
Figure 37:
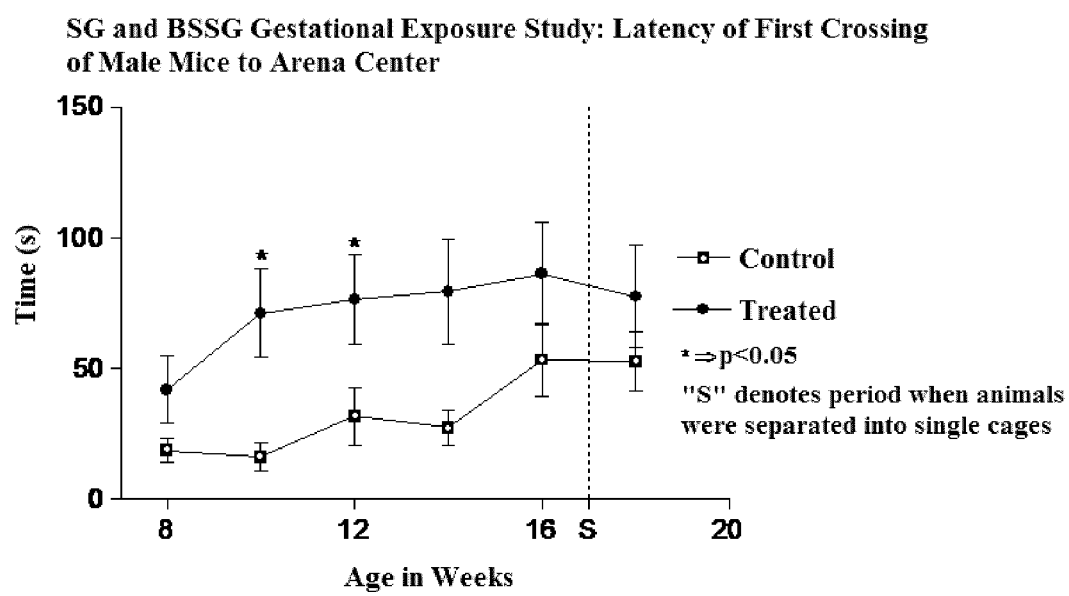
Figure 38:
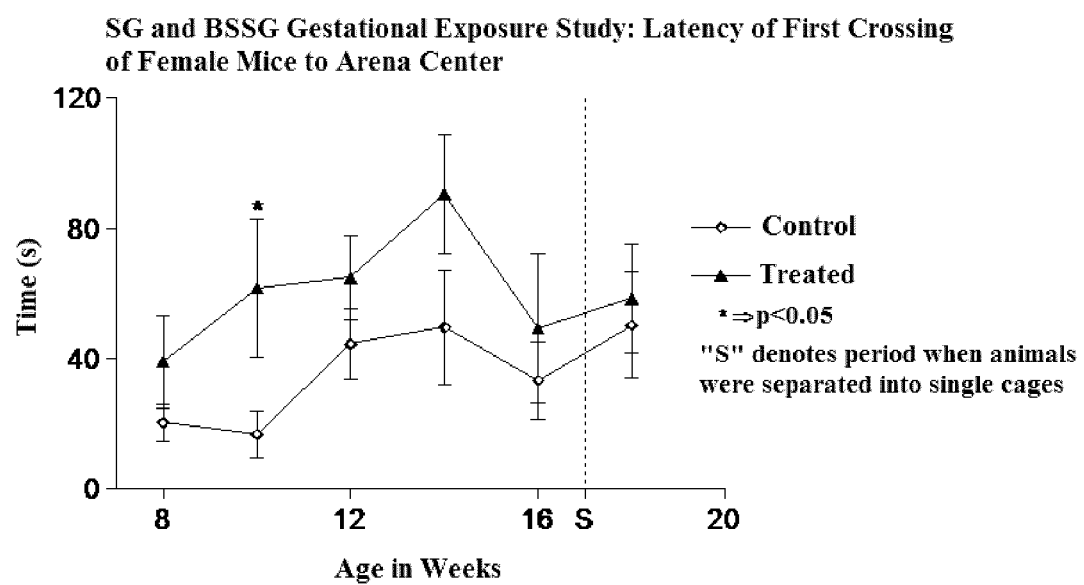
Figure 39:
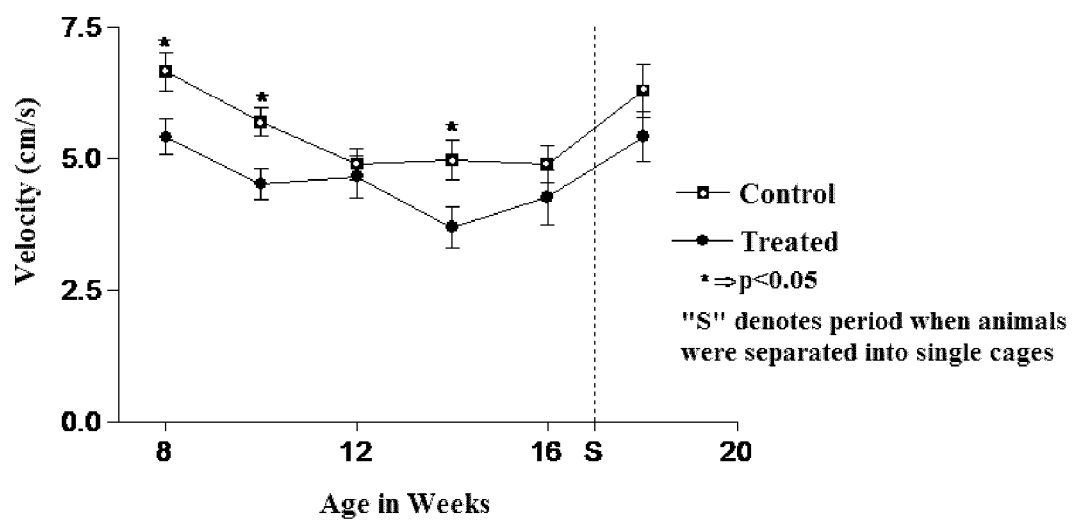
Figure 40:
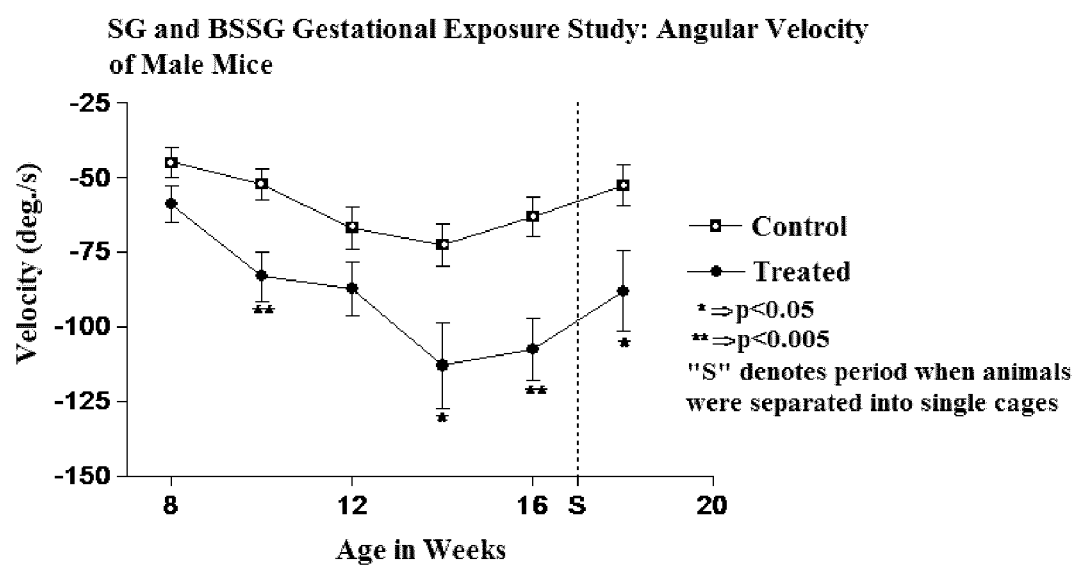
Figure 41:
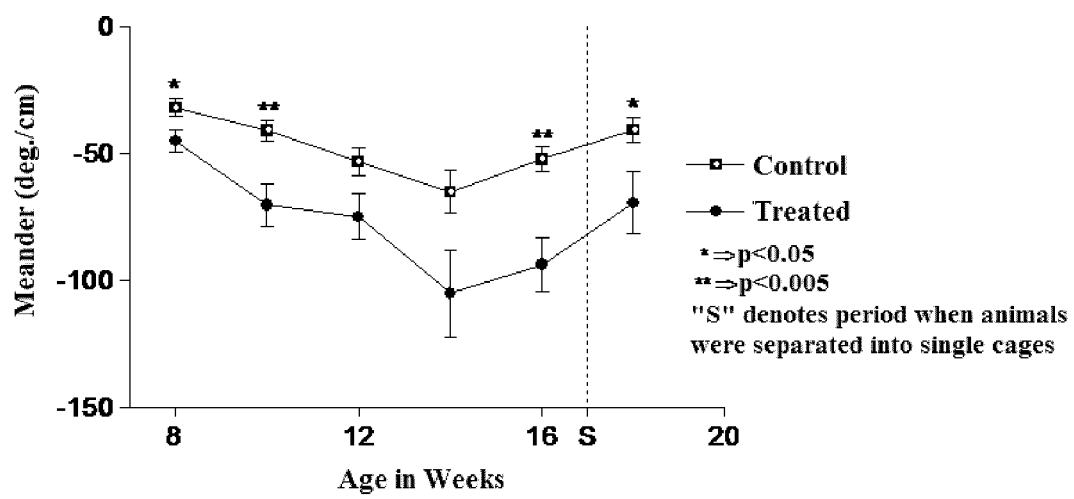

Nine (9) 5-month-old CD-1 female mice were purchased from Charles River Laboratories (Wilmington, Mass.) and allowed one week to acclimatize to the new animal holding facility. Following the period of acclimatization, the female mice were group-housed in 3 groups of 3 in cages containing soiled male bedding to induce and synchronize the estrous cycle in the females. On the third day, the females were age-matched with nine CD-1 males at the end of the daily light cycle. The females were checked for an ejaculatory plug every morning. The day a plug was found was recorded as the first day of pregnancy or as embryonic day 1 (E1). Once a plug was found, the female was separated from the male and returned to her home cage. On E10 and E11, a mouse chow pellet containing a combination of two of the identified cycad steryl glucosides (0.6 mg BSSG and 0.4 mg stigmasterol glucoside (SG)) based on the average amount found in 1 g of cycad seed used in previous cycad feeding experiments was fed to five (5) of the pregnant females, while the remaining animals received standard mouse chow pellets (Khabazian et al., 2002; Wilson et al., 2002). Days E10 and E11 were chosen to target the differentiation of the nigro-striatal pathway in the developing nervous system (Bayer et al., 1995; Rice and Barone, 2000). Pregnant females were monitored daily for any unusual behavior. Parturition typically occurred between E19 and E20, and the litter number ranged between 8-15 pups per litter, with an average of ~10 pups per litter. The control dams had an average litter size of 11.6 pups, while the dams fed the BSSG and SG had an average litter size of 9.5 pups. Although the control dams had a slightly higher average litter size, there were no significant differences in either the litter number, or the sex of pups born to the control or BSSG and SG-fed mothers. The mortality rate of the pups was 11%, as one of the control dams lost 6 pups of her litter of 8. Two of the BSSG and SG-fed mothers also lost a pup each out of a litter of 8 and 12 respectively. All surviving pups were weighed within 24 hr of birth, and then on a weekly basis. On day 22, mice were weaned, ear-punched for identification, and then group-housed by sex in a 12:12-hour light-dark cycle with food and water supplied ad libitum. Only pups that were siblings were housed in the same cage. Postnatal behavioral analysis commenced at 5 weeks of age, using different behavioral testing methods described herein. The mice were tested for exploratory activity at various ages during the period beginning at 8 weeks through to 18 weeks following birth. Tests were conducted over 5 minute intervals: animals were placed at the centre of a test arena and several exploratory activity parameters were measured. Treated animals as compared to control animals demonstrated a significant decrease in duration of total movement [(Student's t-test: *$p<0.05$, **$p<0.05$ (FIG. 27); and (Student's t-test: *$p<0.05$) (FIG. 28)]; frequency of grid crossings into the centre of the arena [(Student's t-test: *$p<0.05$, $p<0.005$, *$p<0.0005$) (FIG. 29); and (Student's t-test: *$p<0.05$, $p<0.005$) (FIG. 30)]; mean distance to the arena border (indicating that treated mice showed a preference for the periphery of the arena rather than the center) [(Student's t-test: *$p<0.0005$) (FIG. 31); and (Student's t-test: *$p<0.05$) (FIG. 32)]; and duration of time spent in centre of arena [(Student's t-test: **$p<0.005$) (FIG. 33) and (Student's t-test: *$p<0.05$) (FIG. 34)]. Treated animals compared to control animals also demonstrated a significant increase in mean turn angle [(Student's t-test: *$p<0.05$, $p<0.005$, *$p<0.0005$) (FIG. 35); and (Student's t-test: *$p<0.05$, *$p<0.005$) (FIG. 36)]; and duration of time to cross into arena centre for the first time [(Student's t-test: *$p<0.05$) (FIG. 37) and (Student's t-test: *$p<0.05$) (FIG. 38)]. Further, male treated animals as compared to male control animals demonstrated a significant decrease in velocity (Student's t-test: *$p<0.05$) (FIG. 39); and a significant increase in angular velocity (Student's t-test: *$p<0.05$, **$p<0.005$) (FIG. 40); and degree of meander (Student's t-test: *$p<0.05$, **$p<0.005$) (FIG. 41).

Behavioral tests were performed in a room adjacent to that in which the animals were housed. Animals were housed in a virus-free barrier facility in a temperature-controlled room.

TABLE 1

|  | Time-point 1 | Time-point 2 |
| --- | --- | --- |
| Mouse Strain, sex | CD1 (outbred), male | |
| Mouse age at study start | 20 wk | |
| Numbers (n) | Control = 14; SG-fed = 16 | Control = 7; SG-fed = 8 |
| SG Feeding Duration | 15 wk | 15 wk |
| Post-feeding survival duration | 0 wk | 17 wk |
| Mouse age at sacrifice | 35 wk | 52 wk |
| Behavioral Tests | Leg extension | Leg extension* |
|  | Rotarod | Rotarod |
|  | Wirehang | Wirehang* |
|  | Velocity of movement | Velocity of movement |
|  | Angular velocity | Angular velocity |
|  | Percent time spent moving | Percent time spent moving |
|  | Total distance moved (ns) | Total distance moved |
|  | Total distance to zone border (ns) | Total distance to zone border* |
|  | Total turn angle (ns) | Total turn angle |
|  | Forelimb braking (ns) | Forelimb braking* |
|  | Forelimb propulsion (ns) | Forelimb propulsion* |
|  | Forelimb stance width (ns) | Forelimb stance width |

TABLE 1-continued

| | Time-point 1 | Time-point 2 |
|---|---|---|
| | Forelimb stride length (ns) | Forelimb stride length |
| | Hind limb braking (ns) | Hind limb braking* |
| | Hind limb propulsion (ns) | Hind limb propulsion* |
| | Hind limb stance width (ns) | Hind limb stance width |
| | Hind limb stride length (ns) | Hind limb stride length |
| | Hind limb stride frequency (ns) | Hind limb stride frequency* |
| Motor Neurons per lumbar cord section | Healthy α-MN (ns) | Healthy α-MN: −55%* |
| | Chromatolytic α-MN (ns) | Chromatolytic α-MN (ns) |
| | Pyknotic α-MN (ns) | Pyknotic α-MN (ns) |
| | Total α-MN: −29%* | Total α-MN: -47* |
| | Total γ-MN (ns) | Total γ-MN (ns) |
| | Chromatolytic α-MN (control group & SG-group independently over time) (ns) | |
| | Pyknotic α-MN (control group and SG-group independently over time) (ns) | |
| | Total α-MN (control group over time (ns) | |
| | Total α-MN (SG-fed group over time): −36%* | |
| | Total γ-MN (control group and SG-group independently over time) (ns) | |
| Cholinergic cell number | Cholinergic neurons (−18%) | Cholinergic neurons (−32%) |
| Choline acetyl transferase | Total cholinergic cells (control group over time) (ns) | |
| | Total cholinergic cells (SG-fed group over time): -32%* | |
| Stress induction | Anti-Hsp-70: +1036%*** | Anti-Hsp-70: +425%* |
| Heat shock protein-70 | (VHLsc) | (VHLsc) |
| Activating transcription factor-3 | Anti-Hsp-70: (ns, p = 0.9697) | Anti-Hsp-70: (ns, p = 0.2793) |
| | (VHTsc) | (VHTsc) |
| Phosphorylated $Jun_{ser}73$ | Anti-Hsp-70 Lsc (control group over time) (ns, p = 0.7334) | |
| | Anti-Hsp-70 Lsc (SG-fed group over time) (ns, p = 0.1223) | |
| | Anti-Hsp-70 Tsc (control group over time) (ns, p = 0.2967) | |
| | Anti-Hsp-70 Tsc (SG-fed group over time) (ns, p = 0.8319) | |
| | Anti-ATF-3: +242% *** | Anti-ATF-3: +101%** |
| | Anti-ATF-3 immunoreactive cells (control group over time) (ns) | |
| | Anti-ATF-3 immunoreactive cells (SG-fed group over time): −48%*** | |
| | Anti-pJun: +199%* | Anti-pJun (ns) |
| | Anti-pJun immunoreactive cells (control group over time) (ns) | |
| | Anti-pJun immunoreactive cells (SG-fed group over time) (ns) | |
| Apoptotic activity | Anti-active caspase 3: +78%*** | (ns) |
| Active Caspase-3 | Apoptotic cells (control group over time) (ns) | |
| | Apoptotic cells (SG-fed group over time) (ns) | |
| Astrocyte proliferation | Anti-GFAP: +337%*** | Anti-GFAP: +119%* |
| Glial fibrillary acidic protein | Astrocytes (control group over time): +41%* | |
| | Astrocytes (SG-fed group over time): −30%* | |
| Microglia proliferation | Anti-IBA1: +33%** | Anti-IBA1: +59%* |
| Ionized calcium-binding adaptor molecule-1 | Anti-IBA-1 immunoreactive cells (control group over time) (ns) | |
| | Anti-IBA-1 immunoreactive cells (SG-fed group over time) (ns) | |
| Cytochrome c oxidase Activity | (ns) | (ns) |
| | Optical density (control group over time): −47%*** | |
| | Optical density (SG-fed group over time): −36%** | |
| Dopaminergic cells | −34%*** | −39%* |
| Tyrosine Hydroxylase | Optical density (control group over time) (ns) | |
| | Optical density (SG-group over time): −22%* | |
| Lipid deposits | Lipid deposits Lsc VH: +28* | Lipids deposits Lsc VH: +10%* |
| Oil red O | Control Lsc over time: +29%* | |
| | SG-fed Lsc over time: ns, p = 0.4864 | |
| | Control DR over time: ns, p = 0.4864 | |
| | SG-fed DR over time: ns, p = 0.8062 | |
| | Control VR over time: ns, p = 0.1301 | |
| | SG-fed VR over time: ns, p = 0.5478 | |
| Phosphorylated tau aggregates | − | + (in 2/8 of SG-fed group) |
| Phosphorylated TDP-43 aggregates | − | + (in 2/8 of SG-fed group) |

*p < 0.05;
**p < 0.01;
***p < 0.00
not significant = ns;
Lsc = lumbar spinal cord;
Tsc = thoracic spinal cord;
ventral horn = VH;
dorsal root = DR:
− = not present;
+ = present

EXAMPLE 16

Synthesis of Sterol Glucosides

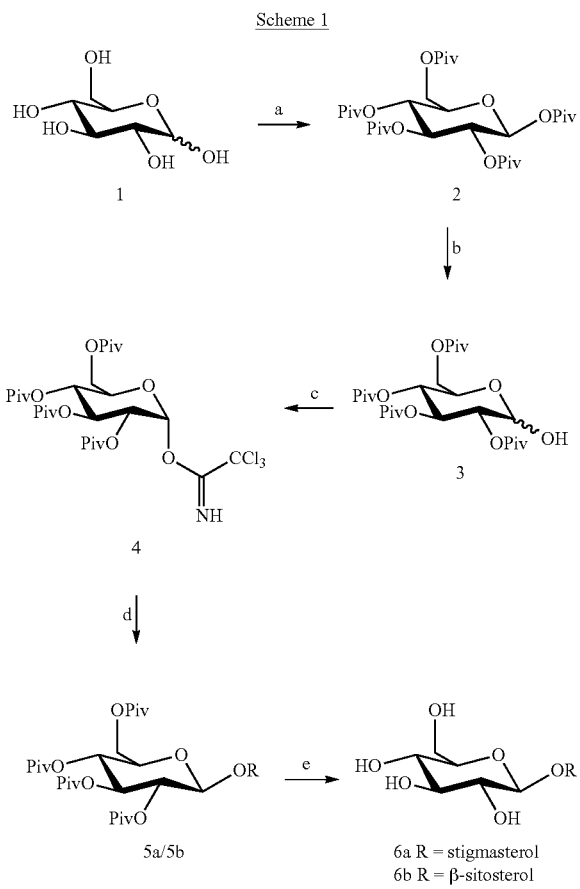

Scheme 1 a.) Pivaloyl chloride, 1:1 pyridine, CH$_2$Cl$_2$; b.) i. HBr-HOAc, CH$_2$Cl$_2$, 0° C.; ii. Ag$_2$CO$_3$, acetone, H$_2$O; c.) trichloroacetonitrile, DBU, CH$_2$Cl$_2$, -30° C.; d.) stigmasterol or b-sitosterol, BF$_3$•Et$_2$O, CH$_2$Cl$_2$, -30° C.; e.) NaOMe/MeOH β-D-Glucose pentapivaloate (2). Compound 2 was synthesized as shown in Scheme 1, a yield of 78% was obtained. Mp: 153-156° C. $^1$H NMR (CDCl$_3$, 400 MHz): δ 5.70 (d, J=8.3 Hz, 1H), 5.38 (t, J=9.2 Hz, 1H), 5.22 (t, J=9.2 Hz, 1H), 5.17 (t, J=9.6 Hz, 1H), 4.18-4.07 (m, 2H), 3.90-3.83 (m, 1H), 1.23 (s, 9H), 1.18 (s, 9H), 1.16 (s, 9H), 1.12 (s, 18H).

2,3,4,6-Tetra-O-pivaloyl-D-glucopyranose (3). Compound 3 was synthesized as shown in Scheme 1. A white foam was isolated in a 99% yield. The crude compound was used in the next reaction without further purification.

2,3,4,6-Tetra-O-pivaloyl-α-D-glycopyranosyl trichloroacetimidate (4). Compound 4 was synthesized as shown in Scheme 1. A pure white powder was isolated in an 86% yield. Spectral values match those previously reported; mp: 133° C. (decomp.); $^1$H NMR (CDCl$_3$, 400 MHz): δ 8.68 (s, 1H), 6.58 (d, J=3.5 Hz, 1H), 5.66 (t, J=10.0 Hz, 1H), 5.23 (t, J=10.0 Hz, 1H), 5.16 (dd, J=10.0, 3.9 Hz, 1H), 4.28-4.05 (m, 3H), 1.20 (s, 9H), 1.18 (s, 9H), 1.14 (s, 18H).

Stigmasterol 2,3,4,6-Tetra-O-pivaloyl-β-D-glycopyranoside (5a). A suspension of 12.45 g of stigmasterol (30.16 mmol), 21.93 g of trichloroacetimidate 4 (33.18 mmol), and 12.75 g of 4 Å molecular sieves in 550 mL of dichloromethane was stirred for 0.5 h at rt. After 0.5 h, 2.62 mL of boron trifluoride diethyl etherate (20.83 mmol) was added dropwise via syringe. The reaction mixture was stirred for 2 h at rt. A second portion of trichloroacetimidate 4 (1.01 g, 1.53 mmol) was added and the reaction mixture was stirred for another 2 h at rt. The pink solution was filtered and the molecular sieves were washed several times with dichloromethane. The solution was washed once with a saturated solution of sodium bicarbonate and then brine. The organic solution was dried over sodium sulfate, filtered, and concentrated in vacuo to afford a think, off-white solid. The solid was recrystallized from ethanol to give 22.43 g (73%) of a white solid. $^1$H NMR (CDCl$_3$, 400 MHz): δ 5.34-5.30 (m, 2H), 5.19-5.13 (m, 1H), 5.09-4.97 (m, 3H), 4.21 (dd, J=12.2, 1.7 Hz, 1H), 4.04 (q, J=6.5 Hz, 1H), 3.74 (qd, J=6.5, 1.7 Hz, 1H), 3.51-3.43 (m, 1H), 2.23-0.70 (m, 80H).

Stigmasterol β-D-Glucopyranoside (6a). To a suspension of 23.38 g of stigmasterol 2,3,4,6-tetra-O-pivaloyl-β-D-glycopyranoside (5) (25.66 mmol) in 850 mL of dry methanol was added a solution of 2.07 g of sodium metal (89.81 mmol) in 50 mL of dry methanol via cannula. The reaction mixture was heated to reflux for 24 h. The mixture was cooled to RT and the white solid was filtered. The filtrate was neutralized with Amberlite and the solvent was evaporated to give another portion of white solid. The solids were combined and suspended in 400 mL of water. The mixture was heated to reflux for 0.5 h. After cooling to rt, the solids were filtered and dried. The resulting compound was dissolved in 300 mL of pyridine. The product was then precipitated using 600 mL of water. The white solid was filtered, washed once with water, methanol, and acetone before being dried under vacuum to give 13.36 g (91% yield) of the title compound as a white powder. $^1$H NMR (DMSO, 600 MHz): 5.33-5.32 (m, 1H), 5.18-5.12 (m, 1H), 5.04-5.00 (m, 1H), 4.89 (d, J=4.8 Hz, 1H), 4.87 (dd, J=4.8, 1.7 Hz, 2H), 4.43 (t, J=5.7 1H), 4.21 (d, J=7.9 Hz, 1H), 3.64 (qd, J=5.7, 1.8 Hz, 1H), 3.49-3.43 (m, 1H), 3.40 (quint., J=5.9 Hz, 1H), 3.13-3.19 (m, 1H), 3.08-3.05 (m, 1H), 3.03-2.99 (m, 1H), 2.91-2.87 (m, 1H), 2.39-2.34 (m, 1H), 2.12 (t, J=12.1 Hz, 1H), 2.06-1.99 (m 1H), 1.95-1.90 (m, 2H), 1.82-1.78 (m, 2H), 1.67-1.61 (m, 1H), 1.53-1.36 (m, 9H), 1.26-1.10 (m, 4H), 1.07-0.67 (m, 18H). $^{13}$C NMR (DMSO, 150 MHz): δ 141.3, 138.1, 128.8, 121.2, 100.8, 76.9, 76.8, 73.5, 70.1, 61.1, 56.3, 55.3, 50.6, 49.6, 41.9, 40.0, 39.9, 39.1, 38.3, 36.8, 36.2, 31.4, 31.3, 31.2, 29.3, 28.5, 24.9, 23.9, 21.1, 20.9, 20.6, 19.11, 18.9, 12.2, 11.9. MS (ESI): 597 (M+Na$^+$).

Scheme 2

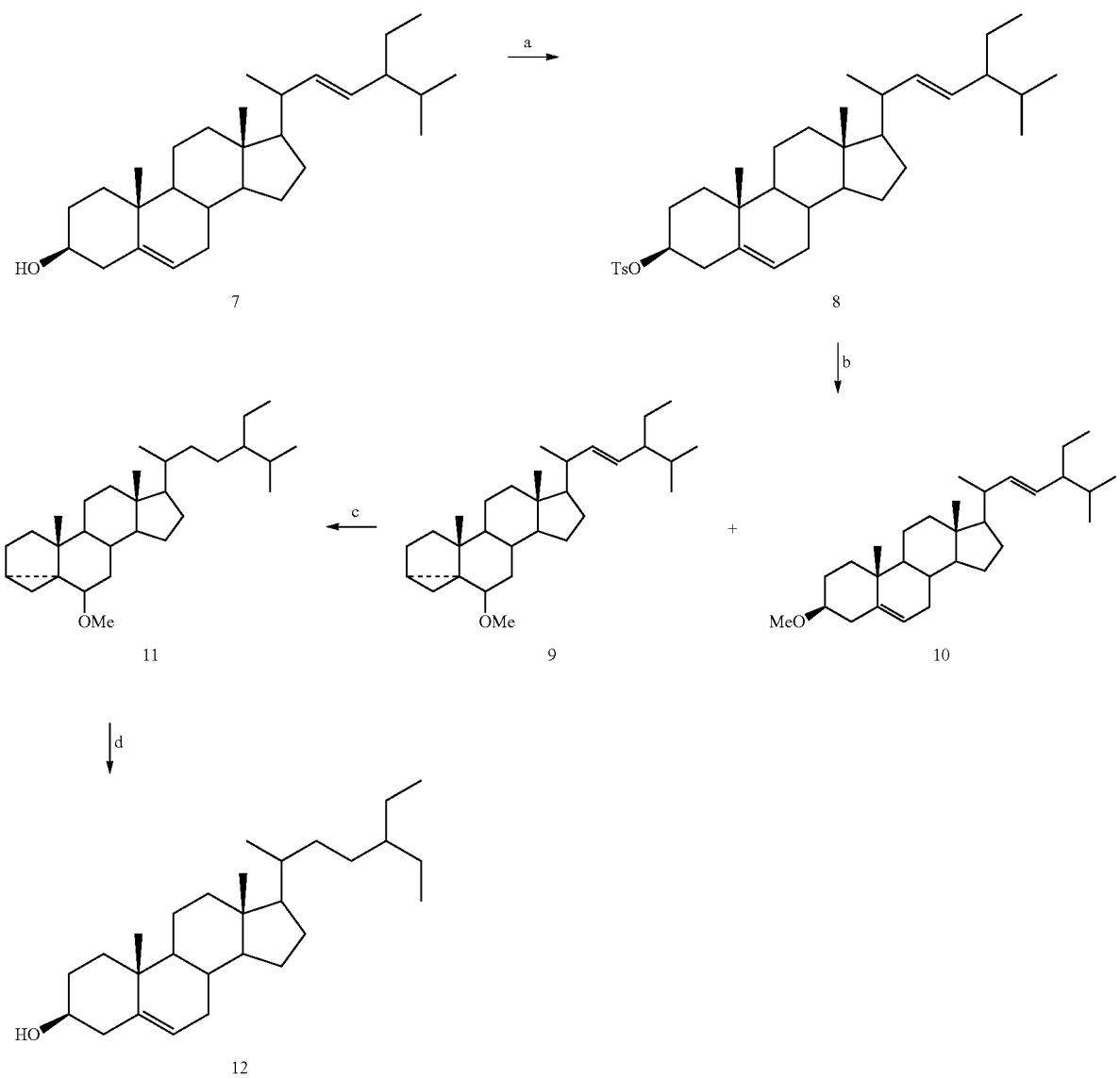

Stigmasterol tosylate (8). A solution of 28.29 g of stigmasterol (68.55 mmol), 27.44 g of tosyl chloride (143.95 mmol), and 0.838 g of 4-(dimethylamino)pyridine (6.85 mmol) in 350 mL of distilled pyridine was stirred for 24 hours at rt. The reaction mixture was then poured into a 2 L Erlenmeyer flask containing 1.2 L of a 10% solution of sodium bicarbonate. The solid was filtered and washed with water. The product was dissolved in hot acetone and filtered to remove the insoluble white solid. The acetone was evaporated to a minimum volume and the product was recrystallized to afford 34.77 g (89%) of the title compound as clear needles. $^1$H NMR (CDCl$_3$, 400 MHz): δ 7.80 (d, J=8.3 Hz, 2H) 7.33 (d, J=7.8 Hz, 2H), 5.31-5.30 (m, 1H) 5.18-5.12 (m, 1H), 5.05-4.99 (m, 1H), 4.37-4.29 (m, 1H), 2.45 (s, 3H), 2.42-0.68 (m, 43H) (McCarthy, et al., Org. Biomol. Chem. 2005, 3, 3059-3065).

Stigmasterol methyl ether (9). To a solution of 2.901 g of stigmasterol tosylate (8) (5.12 mmol) in 40 mL of dry methanol was added 1.24 mL of pyridine (15.35 mmol) via syringe. The white suspension was heated to reflux for 6 h. The reaction mixture was cooled to rt and the solvent was removed in vacuo to afford a white solid. The residue was extracted into ethyl acetate and washed twice with water and once with a saturated solution of ammonium chloride. The combined aqueous fractions were extracted once with ethyl acetate. The combined organics were dried over sodium sulfate, filtered, and concentrated in vacuo to afford a clear, foamy solid. The crude product was purified on silica gel (20:1 hexanes:ethyl acetate) to afford 1.94 g (89%) of a clear, viscous oil which contained a 5:1 mixture of compounds 9:10. The crude reaction mixture was used in the next reaction without further purification.

β-Sitosterol (12). To a solution of 10.93 g of the mixture of compounds 9 and 10 (25.61 mmol) in 50 mL of distilled ethanol was added 2.73 g of 5% palladium on carbon. The Parr shaker was filled with hydrogen gas at a pressure of 50 psi and shaken for 20 h. The completion of the reaction was verified by $^1$H NMR. The reaction mixture was filtered through Celite and concentrated to afford an oily solid. The solid was dissolved in 150 mL of dioxane and 25 mL of water before adding 0.487 g of tosic acid (2.56 mmol). The solution was heated to 80° C. for 5 h. The solution was cooled to rt and the solvent was removed in vacuo to afford a white residue. The residue was taken up in chloroform and washed twice with water and twice with brine. The organic layer was dried over sodium sulfate, filtered, and concentrated to afford a white/yellow solid. The crude compound was purified on silica gel (5:1→1:1 hexanes:ethyl acetate) to afford 5.23 g (33% over 4 steps) of the title compound as a white solid. $^1$H NMR (CDCl$_3$, 400 MHz): δ 5.36-5.34 (m, 1H), 3.56-3.48 (m, 1H), 2.32-0.68 (m, 48H).

β-Sitosterol 2,3,4,6-Tetra-O-pivaloyl-β-D-glucopyranoside (5b). The synthesis of 5b was carried as shown in Scheme 1 to afford 15.05 g (74%) of the title compound as a white powder; mp: 185-188° C. $^1$H NMR (CDCl$_3$, 400 MHz): 5.34-5.30 (m, 1H), 5.07 (t, J=9.6 Hz, 1H), 5.00 (t, J=9.6 Hz, 1H), 4.63 (d, J=7.9 Hz, 1H), 4.21 (dd, J=11.6, 1.2 Hz, 1H), 4.05-4.01 (m, 1H), 3.75-3.71 (m, 1H), 3.51-3.43 (m, 1H), 2.21-0.68 (m, 84H).

β-Sitosterol β-D-Glucopyranoside (6b). The synthesis of compound 6b was carried out as shown in Scheme 1 to afford 9.13 g (96%) of the title compound as a white powder; mp: 203° C. (decomp.); $^1$H NMR (DMSO, 400 MHz): δ 5.33-5.31 (m, 1H), 4.87-4.82 (m, 3H), 4.40 (t, J=5.7 Hz, 1H), 4.21 (d, J=7.8 Hz, 1H), 3.63 (dd, J=5.7, 1.3 Hz, 1H), 3.49-3.38 (m, 2H), 3.18-2.99 (m, 4H), 2.92-2.87 (m, 1H), 2.36 (dd, J=13.1, 3.1 Hz, 1H), 2.15-0.65 (m, 42H). $^{13}$C NMR (DMSO, 100 MHz): δ 207.9, 141.9, 122.7, 102.3, 78.4, 78.2, 74.9, 71.6, 62.6, 57.6, 56.9, 51.1, 46.6, 43.3, 39.8, 38.3, 37.7, 36.9, 34.8, 32.9, 32.8, 32.1, 30.7, 30.2, 29.2, 26.9, 25.3, 24.1, 22.1, 21.2, 20.6, 20.4, 20.1, 13.2, 13.1. MS (ESI): 599 (M+Na$^+$).

EXAMPLE 17

Synthesis of Sterol Glucosides

Synthesis of cholesterol-β-D-glucoside. Glucoside synthesis was accomplished according to the method of Kunz and Harreus [21]; 1.45 g (2.5 mmol) tetra-O-pivaloyl-α-D-glucopyranosyl bromide, 1.35 g (3.5 mmol) cholesterol, 0.83 g (3 mmol) silver carbonate, 0.05 g silver trifluoromethanesulfonate and 5 g molecular sieve (3 Å) were stirred under argon in 30 ml dry ether for 24 h. The reaction mixture was filtered, the filtrate was evaporated to dryness and the residue was purified by silica gel flash chromatography using petroleum-ether/ethyl acetate (10:1) as mobile phase. The purified cholesterol-tetra-O-pivaloyl-β-D-glucoside was suspended in 50 ml methanol and 10 ml sodium methoxide (0.1 mol/l) were added. After refluxing for 24 h, the solution was cooled and diluted with 100 ml methanol. The precipitated product was filtered off, boiled with water, filtered again and dried under reduced pressure. The crude crystals were dissolved in hot pyridine and precipitated by adding water to the hot solution. After the suspension was left overnight at ca. 4° C., the product was filtered off. The colourless crystals were washed with water and acetone, and dried over potassium hydroxide in vacuum to obtain pure cholesterol β-D-glucoside. Dihydrocholesterol and stigmasterol were processed accordingly to obtain dihydrocholesterol-β-D-glucoside and stigmasterol-β-D-glucoside. Characterisation of standard substances was carried out using NMR ($^1$H and $^{13}$C) and high resolution mass spectrometry (HRMS). Purity was also verified using HPLC in combination with ELSD and UV detection.

Cholesterol-β-D-glucoside: Yield: 1.9 g (85%), purity>99% (HPLC), MP 262-263° C. $^{13}$C NMR (100 MHz, pyridine-d$_5$): δ=12.16, 19.11, 19.60, 21.47, 22.85, 23.10, 24.31, 24.66, 28.41, 28.67, 30.45, 32.24, 32.36, 36.20, 36.66, 37.11, 37.67, 39.53, 39.90, 40.15, 42.66, 50.55, 56.54, 57.01, 63.05, 71.91, 75.53, 78.29, 78.67, 78.80, 102.78, 122.10, 141.10. HRMS calculated for C$_{33}$H$_{56}$O$_6$ (M$^+$): 548.4077, found 548.4093.

Dihydrocholesterol-β-D-glucoside: Yield: 1.0 g (70%), Purity>99% (HPLC), MP 256-258° C. $^{13}$C NMR (100 MHz, pyridine-d$_5$): δ=12.42, 12.49, 19.07, 21.63, 22.85, 23.10, 24.31, 24.61, 28.41, 28.69, 29.22, 30.20, 32.45, 35.03, 35.78, 35.91, 36.20, 36.64, 37.41, 39.90, 40.41, 42.95, 44.80, 54.66, 56.69, 56.74, 63.15, 72.01, 75.56, 77.36, 78.73, 78.85, 102.32. HRMS calculated for C$_{33}$H$_{58}$O$_6$ (M$^+$): 550.4233, found 550.4218.

Stigmasterol-β-D-glucoside: Yield: 1.1 g (73%), Purity>96% (HPLC), MP 297-298° C. $^{13}$C NMR (100 MHz, pyridine-d$_5$): δ=12.17, 12.54, 19.21, 19.44, 21.29, 21.31, 21.50, 24.57, 25.72, 29.33, 30.29, 32.09, 32.19, 36.97, 37.51, 39.38, 39.86, 40.80, 42.39, 50.39, 51.45, 56.11, 56.96, 62.89, 71.75, 75.38, 78.12, 78.51, 78.65, 102.61, 121.93, 129.50, 138.85, 140.95. HRMS calculated for C$_{35}$H$_{58}$O$_6$ (M$^+$): 574.4233, found 574.4251.

While certain embodiments of the present invention have been described and/or exemplified above, it is contemplated that considerable variation and modification thereof are possible. Accordingly, the present invention is not limited to the particular embodiments described and/or exemplified herein.

What is claimed is:

1. A method of monitoring a neurodegenerative disease in a non-human animal, the method comprising the steps of
    administering to the non-human animal a composition comprising a neurotoxic compound, wherein the compound is stigmasterol glucoside; and
    monitoring the neurodegenerative disease in the non-human animal.

2. The method of claim 1 wherein the neurotoxic compound is stigmasterol beta-D-glucoside.

3. The method of claim 1 wherein the non-human animal is a rodent.

4. The method of claim 1 wherein the non-human animal is a primate.

5. The method of claim 1 wherein the neurodegenerative disease is selected from the group consisting of amyotrophic lateral sclerosis, early onset Parkinson's disease, late onset Parkinson's disease, and Alzheimer's disease.

6. The method of claim 1 wherein the non-human animal is a fetal animal.

7. A method of monitoring a neurodegenerative disease in a non-human animal, the method comprising the steps of
    administering to the non-human animal a composition comprising a neurotoxic compound, wherein the compound is stigmasterol glucoside; wherein the non-human animal is a fetal animal; and
    monitoring the neurodegenerative disease in the non-human animal.

8. The method of claim 7 wherein the non-human animal is a male animal.

* * * * *